(12) United States Patent
Agrawal et al.

(10) Patent No.: US 10,431,325 B2
(45) Date of Patent: Oct. 1, 2019

(54) METHODS TO IDENTIFY AMINO ACID RESIDUES INVOLVED IN MACROMOLECULAR BINDING AND USES THEREFOR

(71) Applicants: Novartis AG, Basel (CH); Massachusetts Institute of Technology (MIT), Cambridge, MA (US)

(72) Inventors: Neeraj J. Agrawal, Cambridge, MA (US); Bernhard Helk, Basel (CH); Bernhardt L. Trout, Cambridge, MA (US)

(73) Assignees: NOVARTIS AG, Basel (CH); MASSACHUSETTS INSTITUTE OF TECHNOLOGY (MIT), Cambridge, MA (US)

(*) Notice: Subject to any disclaimer, the term of this patent is extended or adjusted under 35 U.S.C. 154(b) by 182 days.

(21) Appl. No.: 14/419,229

(22) PCT Filed: Aug. 2, 2013

(86) PCT No.: PCT/US2013/053499
§ 371 (c)(1),
(2) Date: Feb. 2, 2015

(87) PCT Pub. No.: WO2014/022817
PCT Pub. Date: Feb. 6, 2014

(65) Prior Publication Data
US 2015/0205912 A1  Jul. 23, 2015

Related U.S. Application Data

(60) Provisional application No. 61/679,645, filed on Aug. 3, 2012.

(51) Int. Cl.
*G16B 15/00* (2019.01)
*G16B 35/00* (2019.01)
*G16B 5/00* (2019.01)
*G16C 20/60* (2019.01)
*C07K 1/107* (2006.01)

(52) U.S. Cl.
CPC .............. *G16B 15/00* (2019.02); *C07K 1/107* (2013.01); *G16B 35/00* (2019.02); *G16C 20/60* (2019.02); *G16B 5/00* (2019.02)

(58) Field of Classification Search
None
See application file for complete search history.

(56) References Cited

U.S. PATENT DOCUMENTS

| 6,277,375 | B1 | 8/2001 | Ward |
| 8,747,848 | B2 | 6/2014 | Chennamsetty et al. |
| 9,676,841 | B2 | 6/2017 | Chennamsetty et al. |
| 2002/0103212 | A1 | 8/2002 | Serizawa et al. |
| 2005/0244403 | A1 | 11/2005 | Lazar et al. |
| 2006/0271306 | A1 | 11/2006 | Dobson et al. |
| 2007/0092940 | A1 | 4/2007 | Eigenbrot et al. |
| 2007/0202098 | A1 | 8/2007 | Lazar et al. |
| 2008/0050310 | A1 | 2/2008 | Ebens |
| 2010/0297103 | A1 | 11/2010 | Murakami |
| 2011/0257104 | A1* | 10/2011 | Chennamsetty ........ G06F 19/16 514/21.2 |
| 2013/0053547 | A1 | 2/2013 | Kai et al. |

FOREIGN PATENT DOCUMENTS

| CN | 1671741 A | 9/2005 |
| CN | 1958615 A | 5/2007 |
| EP | 1810979 A1 | 7/2007 |
| EP | 2006380 A1 | 12/2008 |
| JP | 2003-263465 A | 9/2003 |
| WO | WO 2003/074679 A2 | 9/2003 |
| WO | WO 2004/001007 A2 | 12/2003 |
| WO | WO 2005/045442 A1 | 5/2005 |
| WO | WO 2006/033386 A1 | 3/2006 |
| WO | WO 2006/034488 A2 | 3/2006 |
| WO | WO 2006/119062 A2 | 11/2006 |
| WO | WO 2007/022070 A2 | 2/2007 |
| WO | WO 2007/103288 A2 | 9/2007 |
| WO | WO 2007/109221 A2 | 9/2007 |
| WO | WO 2008/032833 A1 | 3/2008 |
| WO | WO 2008/088983 A1 | 7/2008 |

OTHER PUBLICATIONS

Armon et al. J. Mol. Biol. 307, 447-463, 2001.*
Agrawal et al. (2014). "A computational tool to predict the evolutionarily conserved protein-protein interaction hot-spot residues from the structure of the unbound protein," FEBS Lett, 588(2):326-33.
Chennamsetty et al. (2011). "Prediction of protein binding regions," Proteins, 79(3):888-97.
Cho et al. (2009). "A feature-based approach to modeling protein-protein interaction hot spots," Nucleic Acids Res, 37(8):2672-87.
Hu et al. (2000). "Conservation of polar residues as hot spots at protein interfaces," Proteins, 39(4):331-42.
International Search Report dated Feb. 17, 2014, for International Application No. PCT/US2013/053499, filed Aug. 2, 2013.
Keskin et al. (2008). "Principles of protein-protein interactions: what are the preferred ways for proteins to interact?", Chem Rev, 108(4):1225-44.
Moreira et al. (2007). "Hot spots—a review of the protein-protein interface determinant amino-acid residues," Proteins, 68(4):803-12.
Neuvirth et al. (2004). "ProMate: a structure based prediction program to identify the location of protein-protein binding sites," J Mol Biol, 338(1):181-99.

(Continued)

*Primary Examiner* — Michael L Borin
(74) *Attorney, Agent, or Firm* — Morrison and Foerster LLP

(57) ABSTRACT

The present disclosure relates to methods and computational tools based, at least in part, on computer simulations that identify hot-spot amino acid residues and binding-region amino acid residues of a protein.

17 Claims, 16 Drawing Sheets

(14 of 16 Drawing Sheet(s) Filed in Color)

(56) References Cited

OTHER PUBLICATIONS

Abraham et al. (1987). "Extension of the fragment method to calculate amino acid zwitterion and side chain partition coefficients," Proteins: Structure, function, and genetics 130-152, p. 148.
Black et al. (1991). "Development of hydrophobicity parameters to analyze proteins which bear post- or cotranslational modifications," Anal Biochem 193:72-82.
Brard et al. (Sep. 6, 1999). "Somatic mutation and light chain rearrangement generate autoimmunity in anti-single-stranded DNA transgenic MRUIpr mice" Journal of Experimental Medicine 190(5):691-704.
Burgess et al. (1990). "Possible dissociation of the heparin-binding and mitogenic activities of heparin-binding (acidic fibroblast) growth factor-1 from its receptor-binding activities by site-directed mutagenesis of a single lysine residue," J Cell Biol 111:2129-2138.
Cellmer et al. (May 17, 2007). "Protein aggregation in silico," *Trends in Biotechnology* 25(6):254-257.
Chennamsetty et al. (Aug. 14, 2009). "Aggregation-prone motifs in human immunoglobulin G" J Mol Biol 391(2):404-413.
Chennamsetty, N. et al. (Jul. 2009). "Design of therapeutic proteins with enhanced stability," *Proceedings of the National Academy of Sciences of the United States of America* 106(29):11937-11942.
Connolly (1983). "Solvent-accessible surfaces of proteins and nucleic acids," Science. 221(4612):709-13.
De Groot, N.S. et al. (Sep. 30, 2005). "Prediction of hot spots of aggregation in disease-linked polypeptides," *BMC Structural Biology* 5(1):18.
Gokarn et al. (2008). "Self-buffering antibody formulations," J Pharma Sci 97:3051-3066.
Hou et al. (2005). "An extended aqueous solvation model based on atom-weighted solvent accessible surface areas: SAWSA v2.0 model," J Mol Model 11(1):26-40.
Hsu (1994). "The variation in immunoglobulin heavy chain constant regions in evolution," Semin Immunol. 6(6):383-91.
International Preliminary Report on Patentability dated Feb. 12, 2013, for PCT/US2009/047948, 13 pages.
International Search Report and Written Opinion dated Jan. 25, 2013, for PCT/US2009/047948, 23 pages.
International Search Report and Written Opinion dated Nov. 30, 2009, for PCT Application No. PCT/US2009/047954 filed Jun. 19, 2009, 20 pages.
International search report dated Jan. 12, 2011, for PCT/US2010/037517 filed Jun. 4, 2010, 8 pages.
Ivanov A.S. et al. (2002). "Computer aided drug design based on structure of macromolecular target: I. Search and description of ligand binding sites in target protein," Problems of medical chemistry, 48(3): 304-315 (article in Russian).
Jespers et al. (2004). "Aggregation-resistant domain antibodies selected on phage by heat denaturation," Nature Biotech 22:1161-1165.
Junutula et al. (Aug. 1, 2008). "Site-specific conjugation of a cytotoxic drug to an antibody improves the therapeutic index" Nature Biotechnology 26(8):925-932.
Junutula et al. (Jan. 14, 2008). "Rapid identification of reactive cysteine residues for site-specific labeling of antibody-Fabs" Journal of Immunological Methods, 332(1-2):41-52.
Kellog et al. (1991). "HINT: a new method of empirical hydrophobic field calculation for CoMFA," J Computer-Aided Molec Des 5:545-552.
Lazar et al. (1998). "Transforming growth factor alpha: mutation of aspartic acid 47 and leucine 48 results in different biological activities," Mol Cell Biol 8:1247-1252.
Lee et al. (1971). "The interpretation of protein structures: estimation of static accessibility," J Mol Biol 55:379-400.
Lu et al. (Feb. 2008). "The effect of a point mutation on the stability of IgG4 as monitored by analytical ultracentrifugation," J Pharma Sci 97(2):960-969.
Lyons et al. (Jan. 1, 1990). "Site-specific attachment to recombinant antibodies via introduced surface cysteine residues" Protein Engineering 3(8):703-708.
Nelson et al. (2000). Principles of Biochemistry, p. 1-1152.
Nieba et al. (1997). "Disrupting the hydrophobic patches at the antibody variable/constant domain interface: improved in vivo folding and physical characterization of an engineered scFv fragment," Protein Eng. 10(4):435-44.
Partial European Search Report dated Jun. 11, 2015 for EP15156284. 0, 8 pages.
Patro et al. (1994). "Simulations of kinetically irreversible protein aggregate structure," Biophys J. 66(5):1274-89.
Pawar, A.P. et al. (Jul. 8, 2005). "Prediction of 'Aggregate-prone' and 'Aggregate-susceptible' Regions in Proteins Associated with Neurodegenerative Diseases," *Journal of Molecular Biology* 350(2):379-392.
Putnam et al. (1981). "Amino acid sequence of the first constant region domain and the hinge region of the delta heavy chain of human IgD," Proc Natl Acad Sci U S A. 78(10):6168-72.
Raschke et al. (2001). "Quantification of the hydrophobic interaction by simulations of the aggregation of small hydrophobic solutes in water," Proc Natl Acad Sci U S A. 98(11):5965-9.
Russian Decision to Grant, for Russian Application No. 2011101997/10, filed Jun. 19, 2009, Decision dated Jul. 8, 2015, 20 pages (10 pages translation and 10 pages Russian Decision).
Spassov, V. et al. (1995). "The optimization of protein-solvent interactions: Thermostability and the role of hydrophobic and electrostatic interactions," *Protein Science* 4(8):1516-1527.
Stimmel et al. (Sep. 29, 2000). "Site-specific conjugation on serine-cysteine variant monoclonal antibodies" Journal of Biological Chemistry 275(39):30445-30450.
Thermo Scientific (2003). "Antibody Structure and Classes of Immunoglobulins," 4 pages. Retrieved May 3, 2013 from <http://www.piercenet.com/browse.cfm?fldID=F6556788-5056-8A76-4EAC-3683B8E3197A>.
Voynov et al. (Feb. 17, 2010). "Design and application of antibody cysteine variants." Bioconjugate Chemistry 21(2):385-392.
Wesson et al. (1992). "Atomic solvation parameters applied to molecular dynamics of proteins in solution," Protein Sci 1(2):227-235.

* cited by examiner

100

102
SELECTING FROM A PLURALITY OF AMINO ACID RESIDUES OF A STRUCTURAL MODEL REPRESENTING A PROTIN , A CLUSTER OF HIGHLY HYDROPHOBIC AMINO ACID RESIDUES BY DETERMINING THE EFFECTIVE-HYDROPHOBICITY OF ONE OR MORE RESIDUES TO IDENTIFY TWO OR MORE HIGHLY HYDROPHOBIC RESIDUES HAVING AN EFFECTIVE-HYDROPHOBICITY THAT IS GREATER THAN A CHOSEN THRSHOLD VALUE AND THAT ARE WITHIN A DEFINED DISTANCE OF EACH OTHER

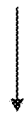

104
SELECTING FROM THE PLURALITY OF AMINO ACID RESIDUES OF THE MODEL OF 102, ONE OR MORE SOLVENT-EXPOSED POLAR AMINO ACID RESIDUES WITHIN A DEFINED DISTANCE OF AT LEAST ONE AMINO ACID RESIDUE IN THE CLUSTER OF HIGHLY HYDROPHOBIC AMINO ACID RESIDUES

106
REMOVING FROM THE CLUSTER OF HIGHLY HYDROPHOBIC AMINO ACID RESIDUES AND THE ONE OR MORE SOLVENT-EXPOSED POLAR AMINO ACID RESIDUES, THOSE AMINO ACID RESIDUES THAT DO NOT MEET A CRITERION FOR EVOLUTIONARY CONSERVATION, TO PRODUCE A SET OF ONE OR MORE PREDICTED HOT-SPOT AMINO ACID RESIDUES

108
STORING THE ONE OR MORE PREDICTED HOT-SPOT AMINO ACID RESIDUES

Figure 1

A
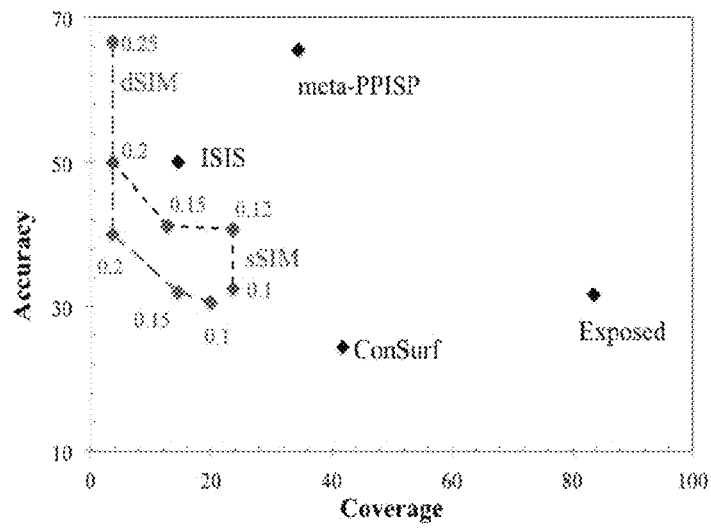
B
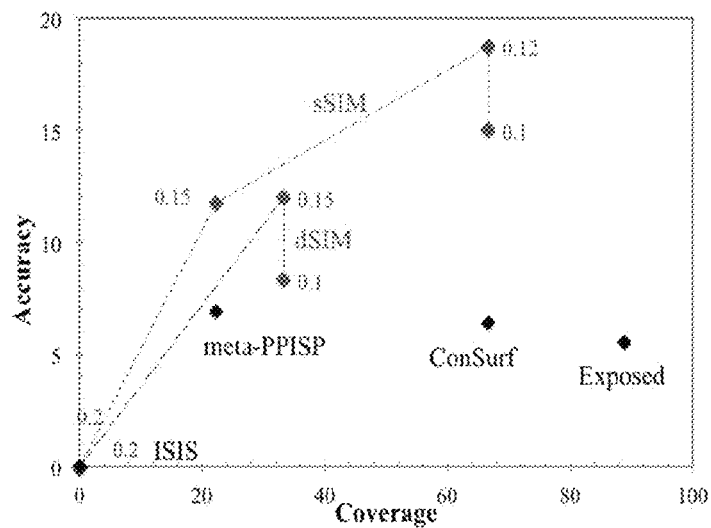
Figure 11

METHODS TO IDENTIFY AMINO ACID RESIDUES INVOLVED IN MACROMOLECULAR BINDING AND USES THEREFOR

CROSS REFERENCE TO RELATED APPLICATIONS

This application is a U.S. National Phase patent application of PCT/US2013/053499, filed Aug. 2, 2013, which claims the benefit of U.S. Provisional Application No. 61/679,645, filed Aug. 3, 2012, all of which are hereby incorporated by reference in the present disclosure in their entirety.

FIELD OF THE INVENTION

The present disclosure relates to computational methods and tools based, at least in part, on computer simulations that identify hot-spot amino acid residues and binding-region amino acid residues of a protein.

BACKGROUND

It is estimated that the human protein-protein interaction (PPI) interactome contains as many as 650,000 different PPIs, and understanding them is expected to lead to new therapeutic targets (Stumpf, M P H et al. *Proc. Natl. Acad. Sci. U.S.A.* 105, 6959-6964, 2008). Proteins are the fundamental functional components of most of the cellular machinery, and formation of specific protein complexes mediated by the respective PPI underpins many cellular processes. Aberrant PPI, either through the loss of function or through formation and/or stabilization of a protein-protein complex at an inappropriate time or location, is implicated in many diseases such as cancer and autoimmune disorders. Identifying and characterizing regions that drive the PPI of proteins involved in such disease will help in understanding the proteins' functions and in designing drugs that target such regions (Thanos et al. *Proc. Natl. Acad. Sci. U.S.A.* 103, 15422-15427, 2006; and Bullock et al. *J. Am. Chem. Soc.* September 14; 133(36):14220-3, 2011).

In the last decade, a large number of protein structures have been solved, and the number of structures of protein-protein complexes is also increasing. These structures of complexes yield information on the residues present in the protein-protein binding region. These residues constitute the PPI structural epitope of the protein. However, not all the residues present in the binding region contribute equally to the binding energy of the complex. For example, work on the binding of human growth hormone (GH) to its receptor identified a region of energetically important residues on the protein surface that were critical to the binding (Cunningham and Wells *Science* 244, 1081-1085, 1989). It has thus become evident that only a few of the binding-region residues contribute a significant fraction of the binding energy. These residues, which constitute the PPI functional epitope, are termed hot-spot residues. One of the rigorous thermodynamic characteristics of a hot-spot residue is that the residue contributes more than 1.3 kcal/mol to the binding energy of the PPI (Ofran and Rost *Plos Computational Biology* 3, 1169-1176, 2007). An operational characteristic of a hot-spot residue is that when the residue is mutated to alanine, the mutation leads to an at least a 10-fold increase in the protein-protein dissociation constant ($K_D$) of the protein.

Experimentally, site-directed mutagenesis has been widely used to analyze how protein-protein interfaces function. In this method, subsets of the protein residues are systematically mutated, typically one at a time, and the effect of mutation on the protein-protein binding energy is analyzed. Preferably, the residue is replaced with alanine, as the alanine amino acid lacks a side chain beyond the β-carbon. Accordingly, binding assays performed in conjunction with alanine mutagenesis can identify hot-spot residues, based on the above operational characteristic. One problem with this technique is that it is tacitly assumed that mutation of a residue to alanine does not lead to structural perturbations of the protein. However, it has been demonstrated that mutating to alanine can in fact result in structural changes to a protein (Rao and Brooks *Biochemistry* 50, 1347-1358, 2011).

One solution to the above problem is to use computational techniques to identify hot spot residues. However, only a few tools have been developed to identify hot spot residues. These tools can be broadly classified into two categories: (1) tools that utilize the structure of the protein-protein complex, and (2) tools that utilize the sequence/structure of the unbound protein.

The first category includes tools that perform in silico alanine scanning mutagenesis of protein-protein interfaces (Kortemme and Baker *Proc. Natl. Acad. Sci. U.S.A.* 99, 14116-14121, 2002; Lise et al. *Plos One* February 28; 6(2):e16774, 2011; Xia et al. *BMC Bioinformatics* April 8; 11:174, 2010; and Tuncbag et al. *Bioinformatics* 25, 1513-1520, 2009). These tools can computationally simulate the effect of mutating an interface residue to alanine on the protein-protein binding free energy (ΔG). Using the structure of the protein-protein complex as an input, these tools can also computationally calculate ΔΔG (change in binding free energy) upon mutation. The parameters of the energy function used to calculate ΔΔG are often obtained by fitting the computational ΔΔG to the experimentally observed ΔΔG for a set of proteins. However, while these tools are able to identify hot spot residues with a reasonable accuracy, the tools require protein-protein complex structures. The requirement for such complex structures is problematic, as it severely limits the application of such tools.

The second category of computational tools overcomes the problem of requiring protein-protein complex structures, by utilizing the sequence or structure of the unbound protein to identify hot spot residues. However, the vast majority of tools appear to only identify binding-region residues using protein structures (Fernandez-Recio *WIREs Comput Mol Sci*, 2011, 1:680-698; and Tuncbag et al. *Briefings in Bioinformatics* 2009, 10, 217-232). To date only the ISIS tool alleges to be able to identify hot spot residues using protein sequences alone (Ofran and Rost *Plos Computational Biology* 2007, 3, 1169-1176; and Ofran and Rost *Bioinformatics* 2007, Jan. 15; 23(2):e13-6).

ISIS is a machine-learning based tool (Ofran and Rost *Plos Computational Biology* 2007, 3, 1169-1176; and Ofran and Rost *Bioinformatics* 2007, Jan. 15; 23(2):e13-6). For each residue in the protein sequence, ISIS bases its predictions on the sequence environment of the residue, its evolutionary profile, its predicted secondary structure, and its solvent accessibility. However, one problem with the ISIS tool is that it does not take into account hydrophobic patches and polar residues within the vicinity of the patches in identifying hot spot residues. It has been shown that the detection of hydrophobic patches on the surfaces of proteins can be used to identify protein binding regions (Lijnzaad, P and Argos, P. *Proteins-Structure Function and Genetics* 28, 333-343, 1997; Chennamsetty et al. *Proc. Natl. Acad. Sci.*

U.S.A. 106, 11937-11942, 2009; Trout et al. *Proteins-Structure Function and Bioinformatics* 79, 888-897, 2011; WO 2009/155518; and U.S. patent application Ser. No. 13/000, 353). Moreover, it has been demonstrated that protein hot spots are characterized by regions patterned with hydrophobic and polar residues (Kozakov, D et al. *Proc. Natl. Acad. Sci. U.S.A.* August 16; 108(33):13528-33, 2011).

Another example of a protein sequence/structure-based tool is meta-PPISP, which identifies binding-region residues from the protein structure (Qin and Zhou *Bioinformatics* 23, 3386-3387, 2007). Meta-PPISP is built on three individual methods: cons-PPISP (Chen and Zhou *Proteins-Structure Function and Bioinformatics* 61, 21-35, 2005), Promate (Neuvirth et al. *J. Mol. Biol.* 338, 181-199, 2004), and PINUP (Zhou et al. *Nucleic Acids Research* 34, 3698-3707, 2006). All three of these methods use sequence conservation along with various different attributes as inputs to predict binding-region residues. Cons-PPISP is based on a neural network and uses evolutionary profiles and solvent accessibility of spatially neighboring residues as inputs. Promate is based on a composite probability calculated from 13 different properties that distinguishes between binding and non-binding region residues. These properties, among others, include evolutionary profile, secondary structure, chemical composition (e.g., amino acid propensities in binding regions), and hydrophobic patch rank. PINUP is based on an empirical energy function, which is a linear sum of three terms: side-chain energy score, residue conservation score and residue interface propensity (it is a function of residue solvent-accessible area). Meta-PPISP combines the raw score of these three methods via a linear equation where the coefficients of the linear equation are obtained by fitting to a database of interacting proteins. However, the meta-PPISP tool is designed to identifying binding-region residues rather than hot-spot residues. Moreover, similar to the problems with ISIS, the meta-PPISP tool does not take into account polar residues within the vicinity of hydrophobic patches.

A further example of a protein sequence/structure-based tool is ConSurf, which maps evolutionarily conserved residues on protein surfaces (Armon, A et al. *J. Mol. Biol.* 307, 447-463, 2001). It is widely accepted that the residues buried in the protein core, which are required for proper folding of the protein, are conserved throughout the evolution. The ConSurf tool is based on the belief that the residues present on the protein surface that are involved in protein-protein interactions are also evolutionarily conserved. However, similar to meta-PPISP, the ConSurf tool identifies residues likely to be at the interface rather than hot-spot residues. Moreover, as ConSurf only utilizes data on evolutionarily conserved resides, it does not take into account hydrophobic patches and polar residues within the vicinity of the patches in identifying hot spot residues.

SUMMARY

Accordingly, a need exists for improved computational tools that utilize multiple protein characteristics, such as patches, or clusters, of hydrophobic residues, polar residues, and evolutionary sequence conservation to more accurately identifying protein hot spot residues.

In order to meet the above needs, the present disclosure provides novel computational methods and tools that identify hot spot amino acid residues of a protein, where the protein is represented in a structural model containing a plurality of amino acid residues from a structural model representing the protein, by identifying and selecting one or more clusters of highly hydrophobic amino acid residues having an effective-hydrophobicity greater than a chosen threshold, selecting one or more solvent-exposed polar amino acid residues within a defined distance of at least one amino acid residue in the selected clusters, identifying and removing from the selected one or more clusters and selected one or more solvent-exposed polar amino acid residues those amino acid residues that do not meet a criterion for evolutionary conservation, to produce a set of one or more predicted hot-spot amino acid residues, and storing the one or more predicted hot-spot amino acid residues.

Additionally, the present disclosure is based, at least in part, on the development of a novel computational tool for accurately predicting hot spot residues using only the structure of an unbound protein. As both hydrophobic and polar (e.g., electrostatic) interactions contribute to the protein-protein binding energy, the disclosed tool was developed to identify clusters of exposed hydrophobic residues along with the exposed polar residues. Moreover and without wishing to be bound by theory, it is believed that evolutionary conservation of residues is an indicator of the relevance of the residue for protein interaction, sequence conservation was used as an additional criterion to improve the quality and accuracy of hot spot residue predictions. Surprisingly, when evaluated against proteins having experimentally determined hot spot residues, the disclosed tool was able to identify hot spot residues with an accuracy that ranged from about 36% to about 57% (see Example and Tables 7 and 8). Advantageously, the disclosed tool, which is a zero-fit model and is not trained on a database, outperformed bioinformatics tools, such as ISIS, meta-PPISP, and ConSurf, which are generally trained on a large database. In particular, the disclosed tool was more accurate than the ISIS tool (2-26%), the meta-PPISP tool (3-26%), and the ConSurf tool (8-26%). Additionally, the disclosed tool can be applied either directly to a static structure of a protein or to multiple conformations generated via molecular simulations, which takes into account the contribution due to protein flexibility and dynamic exposure of the residues. Thus, the inventors have for the first time determined how to combine three distinct sources of information to enable more accurate identification of hot spot residues that has been achieved using only the structure of the unbound protein.

While WO 2009/155518 and U.S. patent application Ser. No. 13/000,353 may disclose methods for identifying macromolecular binding regions; neither of these applications discloses methods for identifying hot spot residues of a protein. Moreover, neither WO 2009/155518 nor U.S. patent application Ser. No. 13/000,353 disclose combining the identification and selection of one or more clusters of highly hydrophobic amino acid residues together with one or more solvent-exposed polar amino acid residues within a defined distance of the cluster with removal of non-evolutionarily conserved amino acid residues to more accurately identify hot spot and binding-region residues of a protein.

Accordingly, one aspect of the present disclosure provides a computer-implemented method for predicting hot-spot amino acid residues of a protein, or portion thereof, where the protein, or portion thereof, is represented in a structural model containing a plurality of amino acid residues, by: (a) selecting from the plurality of amino acid residues of the model, a cluster of highly hydrophobic amino acid residues, where the cluster contains two or more amino acid residues each having an effective-hydrophobicity greater than a chosen threshold, and where each amino acid residue in the cluster is within a first defined distance of at least one other amino acid residue in the cluster; (b) selecting from the plurality of amino acid residues of the model, one or more solvent-exposed polar amino acid residues within a second defined distance of at least one amino acid residue in the cluster of highly hydrophobic amino acid residues; (c) removing from the cluster of highly hydrophobic amino acid residues and from the one or more solvent-exposed polar amino acid residues those amino acid residues that do not meet a criterion for evolutionary conservation, to produce a set of one or more predicted hot-spot amino acid residues; and (d) storing the one or more predicted hot-spot amino acid residues.

In certain embodiments, the method further includes predicting additional hot-spot amino acid residues of the protein, or portion thereof, by repeating steps (a)-(d) for at least two, at least three, at least four, or at least five additional clusters of highly hydrophobic amino acid residues of the protein, or portion thereof. In certain preferred embodiments, the method further includes predicting additional hot-spot amino acid residues of the protein, or portion thereof, by repeating steps (a)-(d) for at least two additional clusters of highly hydrophobic amino acid residues of the protein, or portion thereof. In certain embodiments, the method further includes predicting additional hot-spot amino acid residues of the protein, or portion thereof, for all clusters of highly hydrophobic amino acid residues of the protein, or portion thereof, by performing steps (a)-(d) for each of the clusters, where each step is conducted in parallel for each cluster or each series of steps (a)-(b) is performed serially for each cluster.

In certain embodiments that may be combined with any of the preceding embodiments, the one or more predicted hot-spot amino acid residues are presented to a user. In certain embodiments that may be combined with any of the preceding embodiments, the one or more predicted hot-spot amino acid residues are presented as a contour map visual display. In certain embodiments, the contour map is an electron density map. In certain embodiments that may be combined with any of the preceding embodiments, the contour map is a map of a structural binding pocket.

In certain embodiments, the structural model containing a plurality of amino acid residues is an X-ray crystal structure model of the protein, or portion thereof. In certain embodiments, the structural model containing a plurality of amino acid residues is an NMR structure model of the protein, or portion thereof. In certain embodiments, the structural model containing a plurality of amino acid residues is a theoretical protein structure model of the protein, or portion thereof. In certain embodiments, the structural model containing a plurality of amino acid residues is an ab initio protein structural model of the protein, or portion thereof.

In certain embodiments that may be combined with any of the preceding embodiments, the effective-hydrophobicity threshold is 0.10, 0.15, 0.20, 0.25, 0.30, 0.35, 0.40, 0.45, or 0.50. In certain preferred embodiments, the effective-hydrophobicity threshold is 0.10. In certain embodiments that may be combined with any of the preceding embodiments, the first defined distance between the two or more amino acid residues in the cluster is at most 15 Å, at most 10 Å, at most 5 Å, at most 2 Å, or at most 1 Å. In certain preferred embodiments, the first defined distance between the two or more amino acid residues in the cluster is at most 15 Å. In certain embodiments that may be combined with any of the preceding embodiments, the first defined distance between at least two amino acid residues in the cluster is the shortest distance between any two atoms of the at least two amino acid residues, where each of the two atoms are from separate amino acid residues. In certain embodiments that may be combined with any of the preceding embodiments, the cluster of highly hydrophobic amino acid residues is on the surface of the protein. In certain embodiments that may be combined with any of the preceding embodiments, the cluster was generated by applying the reverse Cuthill-McKee algorithm on pairs of highly hydrophobic amino acid residues that are less than the first defined distance apart.

In certain embodiments that may be combined with any of the preceding embodiments, the polar amino acid residues are charged-amino acid residues. In certain embodiments that may be combined with any of the preceding embodiments, the one or more solvent-exposed polar amino acid residues are identified from the structural model representing the protein, or portion thereof. In certain embodiments that may be combined with any of the preceding embodiments, the one or more solvent-exposed polar-amino acid residues have a solvent accessible area (SAA) greater than 10 Å$^2$, greater than 15 Å$^2$, greater than 20 Å$^2$, greater than 25 Å$^2$, greater than 30 Å$^2$, greater than 35 Å$^2$, greater than 40 Å$^2$, greater than 45 Å$^2$, or greater than 50 Å$^2$. In certain preferred embodiments, the one or more solvent-exposed polar-amino acid residues have a solvent accessible area (SAA) greater than 15 Å$^2$. In certain embodiments that may be combined with any of the preceding embodiments, the one or more solvent-exposed polar amino acid residues are on the surface of the protein. In certain embodiments that may be combined with any of the preceding embodiments, the second defined distance between a solvent-exposed polar-amino acid residue and at least one amino acid residue in the cluster of highly hydrophobic amino acid residues is at most 20 Å, at most 15 Å, at most 10 Å, at most 5 Å, at most 2 Å, or at most 1 Å. In certain preferred embodiments, the second defined distance between a solvent-exposed polar-amino acid residue and at least one amino acid residue in the cluster of highly hydrophobic amino acid residues is at most 20 Å. In certain embodiments that may be combined with any of the preceding embodiments, the method further includes selecting one or more of the solvent-exposed polar amino acid residues to be with within the cluster when the solvent-exposed charged-amino acid residues are within a distance of at most 10 Å, at most 9 Å, at most 8 Å, at most 7 Å, at most 6 Å, or at most 5 Å from a highly hydrophobic amino acid residue in the cluster. In certain preferred embodiments, the method further includes selecting one or more of the solvent-exposed polar amino acid residues to be with within the cluster when the solvent-exposed charged-amino acid residues are within a distance of at most 10 Å from a highly hydrophobic amino acid residue in the cluster.

In certain embodiments that may be combined with any of the preceding embodiments, the criterion for evolutionary conservation is a sequence-conservation threshold. In certain embodiments, the sequence-conservation threshold is a ConSurf score, a Jensen-Shannon divergence score, a BLAST score, or an AL2CO score. In certain embodiments, the sequence-conservation threshold is a ConSurf score. In certain embodiments, the ConSurf score is 0.3, 0.4, 0.5, 0.6, 0.7, 0.8, or 0.9. In certain embodiments, the sequence-conservation threshold is a ConSurf score that is 0.3. In certain embodiments, amino acid residues having a ConSurf score greater than 0.3, greater than 0.4, greater than 0.5, greater than 0.6, greater than 0.7, greater than 0.8, or greater than 0.9 do not meet the criterion for evolutionary conservation. In certain preferred embodiments, amino acid residues having a ConSurf score greater than 0.3 do not meet the criterion for evolutionary conservation.

In certain embodiments that may be combined with any of the preceding embodiments, where the effective-hydrophobicity was calculated by: (a) selecting an amino acid residue from the plurality of amino acid residues of the model; (b) calculating, for all side-chain atoms of the residue, a ratio of the solvent accessible area (SAA) of the atoms to the SAA of atoms in an identical residue which is fully exposed; and (c) multiplying each ratio by the hydrophobicity of the amino acid as determined by an amino acid hydrophobicity scale, whereby the product of step (c) is the effective-hydrophobicity of the amino acid residue. In certain embodiments, the effective-hydrophobicity was calculated for at least two, at least three, at least four, or at least five adjacent amino acid residues of the protein. In certain embodiments that may be combined with any of the preceding embodiments, the method further includes calculating SAAs on main chain atoms. In certain embodiments that may be combined with any of the preceding embodiments, attached hydrogen atoms are excluded from the SAA calculation. In certain embodiments that may be combined with any of the preceding embodiments, the model is processed prior to step (a) by performing a molecular dynamics simulation which optionally includes a solvent. In certain embodiments, the solvent is water. In certain embodiments that may be combined with any of the preceding embodiments, the molecular dynamics simulation is performed using a simulation package selected from ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD. In certain embodiments, the molecular dynamics simulation is performed using the CHARMM simulation package. In certain embodiments, the molecular dynamics simulation is performed using the NAMD simulation package. In certain embodiments that may be combined with any of the preceding embodiments, the effective-hydrophobicity is calculated by conducting a molecular dynamics simulation prior to step (a) and repeating steps (a)-(c), each time conducting a further molecular dynamics simulation at a plurality of time steps, thereby producing multiple sums as in step (c), and calculating the average of the sums, whereby the calculated average is the effective-hydrophobicity for the amino acid residue. In certain embodiments, the molecular dynamics simulation is performed using a simulation package selected from ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD. In certain embodiments, the molecular dynamics simulation is performed using the CHARMM simulation package. In certain embodiments, the molecular dynamics simulation is performed using the NAMD simulation package. In certain embodiments that may be combined with any of the preceding embodiments, the amino acid hydrophobicity scale is the Black and Mould hydrophobicity scale. In certain embodiments, the amino acid hydrophobicity scale is normalized such that glycine has a hydrophobicity of zero. In certain embodiments that may be combined with any of the preceding embodiments, the amino acid hydrophobicity scale is normalized such that phenylalanine has a hydrophobicity of 0.5. In certain embodiments that may be combined with any of the preceding embodiments, the amino acid hydrophobicity scale is normalized such that arginine has a hydrophobicity of −0.5.

Other aspects of the present disclosure provide a method to identify amino acid residues involved in macromolecule binding to a protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify hot-spot amino acid residues involved in macromolecule binding to the protein; and (c) outputting the hot-spot amino acid residues involved in macromolecule binding to the protein.

Other aspects of the present disclosure provide a method to identify a binding-region amino acid residues on the surface of a protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify binding-region amino acid residues on the surface of the protein; and (c) outputting the identified binding-region amino acid residues on the surface of the protein.

Other aspects of the present disclosure provide a method to identify hot-spot amino acid residues on the surface of a protein involved in macromolecule binding to the protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify hot-spot amino acid residues on the surface of the protein; and (c) outputting the identified hot-spot amino acid residues on the surface of the protein.

In certain embodiments that may be combined with any of the preceding embodiments, increasing the effective-hydrophobicity threshold increases identification accuracy. In certain embodiments that may be combined with any of the preceding embodiments, increasing the effective-hydrophobicity threshold reduces protein coverage.

Other aspects of the present disclosure provide a computer-readable storage medium containing computer-executable instructions for predicting hot-spot amino acid residues of a protein, or portion thereof, where the protein, or portion thereof, is represented in a structural model containing a plurality of amino acid residues, the instructions including the steps set forth in the method of any of the preceding embodiments.

Other aspects of the present disclosure provide a computer-readable storage medium containing computer-executable instructions to identify amino acid residues involved in macromolecule binding to a protein, the instructions including: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify binding-region amino acid residues on the surface of the protein; and (c) outputting the identified binding-region amino acid residues on the surface of the protein.

Other aspects of the present disclosure provide a computer-readable storage medium containing computer-executable instructions to identify a binding-region amino acid residues on the surface of a protein, the instructions including: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify binding-region amino acid residues on the surface of the protein; and (c) outputting the identified binding-region amino acid residues on the surface of the protein.

Other aspects of the present disclosure provide a computer-readable storage medium containing computer-executable instructions to identify hot-spot amino acid residues on the surface of a protein involved in macromolecule binding to the protein, the instructions including: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify hot-spot amino acid residues on the surface of the protein; and (c) outputting the identified hot-spot amino acid residues on the surface of the protein.

In certain embodiments that may be combined with any of the preceding embodiments, increasing the effective-hydrophobicity threshold increases identification accuracy. In certain embodiments that may be combined with any of the preceding embodiments, increasing the effective-hydrophobicity threshold reduces protein coverage.

Other aspects of the present disclosure provide a system for predicting hot-spot amino acid residues of a protein, or portion thereof, where the protein, or portion thereof, is represented in structural model containing a plurality of amino acid residues, the system including: (a) a memory configured to store computer-executable instructions for predicting at least one hot-spot amino acid residue; and (b) a processor configured to execute the computer-executable instructions, the instructions including: (i) selecting from the plurality of amino acid residues of the model, a cluster of highly hydrophobic amino acid residues, where the cluster contains two or more amino acid residues each having an effective-hydrophobicity greater than a chosen threshold, and where each amino acid residue in the cluster is within a first defined distance of at least one other amino acid residue in the cluster; (ii) selecting from the plurality of amino acid residues of the model, one or more solvent-exposed polar amino acid residues within a second defined distance of at least one amino acid residue in the cluster of highly hydrophobic amino acid residues; (iii) removing from the cluster of highly hydrophobic amino acid residues and from the one or more solvent-exposed polar amino acid residues those amino acid residues that do not meet a criterion for evolutionary conservation, to produce a set of one or more predicted hot-spot amino acid residues; and (iv) storing the one or more predicted hot-spot amino acid residues.

Other aspects of the present disclosure provide a method for modulating binding of a protein to a macromolecule, by: (a) using the method of any of the preceding embodiments to identify one or more hot-spot amino acid residues on the protein involved in macromolecular binding that can be modified to modulate binding of the protein to the macromolecule; and (b) modifying the identified one or more hot-spot amino acid residues on the protein to modulate binding of the protein to the macromolecule, as compared to a corresponding protein lacking the modified one or more hot-spot amino acid residues.

Other aspects of the present disclosure provide a modified protein having modulated binding to a macromolecule compared to a corresponding non-modified protein, where the protein was produced by modifying one or more hot-spot amino acid residues on the protein involved in macromolecular binding, where the one or more hot-spot amino acid residues were identified using the method of any of the preceding embodiments.

Other aspects of the present disclosure provide a method for producing a therapeutic molecule that inhibits macromolecular binding to a target protein, by: (a) using the method of any of the preceding embodiments to identify one or more hot-spot amino acid residues on the target protein involved in macromolecular binding that can be used to design the therapeutic molecule that inhibits macromolecular binding to the target protein; (b) designing the therapeutic molecule to bind to the one or more hot-spot amino acid residues on the target protein; and (c) producing the therapeutic molecule that inhibits macromolecular binding to the target protein.

Other aspects of the present disclosure provide a therapeutic molecule that inhibits macromolecular binding to a target protein, where the therapeutic molecule was designed to bind one or more hot-spot amino acid residues on the target protein involved in macromolecular binding identified using the method of any of the preceding embodiments.

Other aspects of the present disclosure provide a method for altering at least one function of a protein having at least two functions associated with separate macromolecular binding sites on the protein, by: (a) using the method of any of the preceding embodiments to identify one or more hot-spot amino acid residues on the protein that can be modified to modulate at least one function of the protein; (b) assigning the one or more hot-spot amino acid residues to the respective macromolecular binding site; and (c) modifying the identified one or more hot-spot amino acid residues assigned to the macromolecular binding site associated with the at least one function to alter the at least one function as compared to the at least one function in a corresponding bifunctional protein lacking the modified one or more hot-spot amino acid residues.

Other aspects of the present disclosure provide a modified protein having at least two functions associated with separate macromolecular binding sites on the protein and having at least one of the at least two functions altered as compared to a corresponding non-modified bifunctional protein, where the protein was produced by modifying one or more hot-spot amino acid residues on the protein identified using the method of any of the preceding embodiments and assigned to the macromolecular binding site associated with the at least one function that was to be altered.

Other aspects of the present disclosure provide a method for reducing binding of a first ligand to a receptor protein having at least two ligand binding sites, by: (a) using the method of any of the preceding embodiments to identify one or more hot-spot amino acid residues on the receptor protein; (b) assigning the one or more hot-spot amino acid residues to the respective ligand binding site; and (c) modifying the identified one or more hot-spot amino acid residues assigned to the first ligand binding site to reduce binding of the first ligand to the modified receptor protein as compared to the binding of the first ligand to a corresponding unmodified receptor protein.

Other aspects of the present disclosure provide a modified receptor protein having at least two ligand binding sites and having reduced binding of a first ligand compared to a corresponding non-modified receptor protein, where the bifunctional receptor protein was produced by modifying one or more hot-spot amino acid residues on the receptor protein identified using the method of any of the preceding embodiments and assigned to the first ligand binding site.

Other aspects of the present disclosure provide a method for reducing protein aggregation of a protein without affecting binding, by: (a) using the method of any of the preceding embodiments to identify the predicted hot-spot amino acid residues in a cluster of highly hydrophobic amino acid residues; and (b) replacing at least one residue in the cluster of highly hydrophobic amino acid residues that is not a predicted hot-spot amino acid residues with a less hydrophobic amino acid residue to reduce protein aggregation of the protein without affecting binding, compared to a corresponding protein lacking the replaced at least one amino acid residue.

Other aspects of the present disclosure provide a method for screening one or more small molecules for binding to a target protein, by: (a) using the method of any of the preceding embodiments to identify one or more hot-spot amino acid residues on the target protein involved in binding a first small molecule; and (b) screening a plurality of small molecules related to the first small molecule for binding to the one or more hot-spot amino acid residues on the target protein to identify one or more small molecules that bind the target protein. Other aspects of the present disclosure provide a small molecule that binds a target protein, where the small molecule was identified according to the screening step (b) of the preceding method for screening one or more small molecules for binding to a target protein.

Other aspects of the present disclosure provide a method for improving purification of a target protein from an affinity column, by: (a) using the method of any of the preceding embodiments to identify one or more hot-spot amino acid residues on the target protein involved in protein binding that can be used to synthesize one or more artificial binding sites specific for the target protein in an affinity column; (b) synthesizing the one or more artificial binding sites specific for the target protein in an affinity column; and (c) using the affinity column having the one or more artificial binding sites to purify the target protein, where the affinity column displays improved protein purification for the target protein, compared to protein purification of the target protein using a corresponding affinity column lacking the one or more artificial binding sites.

Other aspects of the present disclosure provide a method for producing a binding partner that specifically interacts with a target protein, by: (a) using the method of any of the preceding embodiments to identify one or more hot-spot amino acid residues on the target protein involved in protein binding that can be used to design the binding partner that specifically interacts with the target protein; (b) designing the binding partner to bind to the one more hot-spot amino acid residues on the target protein; and (c) producing the binding partner that specifically interacts with the target protein. In certain embodiments, the binding partner is a probe, synthetic surface, bead, synthetic peptide, or biologic. Other aspects of the present disclosure provide a binding partner that specifically interacts with a target protein produced by the method for producing a binding partner that specifically interacts with a target protein of any of the preceding embodiments, where the binding partner is a probe, synthetic surface, bead, synthetic peptide, or biologic.

Other aspects of the present disclosure provide a method for producing an epitope that binds a target protein, by: (a) using the method of any of the preceding embodiments to identify one or more hot-spot amino acid residues on the target protein involved in protein binding that can be used to identify the epitope that binds the target protein; (b) identifying the epitope that binds to the one or more hot-spot amino acid residues on the target protein; and (b) producing the epitope that binds the target protein. Other aspects of the present disclosure provide an epitope produced by the preceding method for producing an epitope that binds a target protein.

Other aspects of the present disclosure provide a method for predicting hot-spot amino acid residues of a protein, or portion thereof, where the protein, or portion thereof, is represented in a structural model containing a plurality of amino acid residues, by: (a) selecting from the plurality of amino acid residues of the model, a cluster of highly hydrophobic amino acid residues, where the cluster contains two or more amino acid residues each having an effective-hydrophobicity greater than a chosen threshold, and where each amino acid residue in the cluster is within a first defined distance of at least one other amino acid residue in the cluster; (b) selecting from the plurality of amino acid residues of the model, one or more solvent-exposed polar amino acid residues within a second defined distance of at least one amino acid residue in the cluster of highly hydrophobic amino acid residues; (c) removing from the cluster of highly hydrophobic amino acid residues and from the one or more solvent-exposed polar amino acid residues those amino acid residues that do not meet a criterion for evolutionary conservation, to produce a set of one or more predicted hot-spot amino acid residues; and (d) storing the one or more predicted hot-spot amino acid residues.

In certain embodiments, the method further includes predicting additional hot-spot amino acid residues of the protein, or portion thereof, by repeating steps (a)-(d) for at least two, at least three, at least four, or at least five additional clusters of highly hydrophobic amino acid residues of the protein, or portion thereof. In certain embodiments, the method further includes predicting additional hot-spot amino acid residues of the protein, or portion thereof, for all clusters of highly hydrophobic amino acid residues of the protein, or portion thereof, by performing steps (a)-(d) for each of the clusters, where each step is conducted in parallel for each cluster or each series of steps (a)-(b) is performed serially for each cluster.

In certain embodiments that may be combined with any of the preceding embodiments, the one or more predicted hot-spot amino acid residues are presented to a user. In certain embodiments that may be combined with any of the preceding embodiments, the one or more predicted hot-spot amino acid residues are presented as a contour map. In certain embodiments, the contour map is an electron density map. In certain embodiments that may be combined with any of the preceding embodiments, the contour map is a map of a structural binding pocket.

In certain embodiments, the structural model containing a plurality of amino acid residues is an X-ray crystal structure model of the protein, or portion thereof. In certain embodiments, the structural model containing a plurality of amino acid residues is an NMR structure model of the protein, or portion thereof. In certain embodiments, the structural model containing a plurality of amino acid residues is a theoretical protein structure model of the protein, or portion thereof. In certain embodiments, the structural model containing a plurality of amino acid residues is an ab initio protein structural model of the protein, or portion thereof.

In certain embodiments that may be combined with any of the preceding embodiments, the effective-hydrophobicity threshold is 0.10, 0.15, 0.20, 0.25, 0.30, 0.35, 0.40, 0.45, or 0.50. In certain embodiments that may be combined with any of the preceding embodiments, the first defined distance between the two or more amino acid residues in the cluster is at most 15 Å, at most 10 Å, at most 5 Å, at most 2 Å, or at most 1 Å. In certain embodiments that may be combined with any of the preceding embodiments, the first defined distance between at least two amino acid residues in the cluster is the shortest distance between any two atoms of the at least two amino acid residues, where each of the two atoms are from separate amino acid residues. In certain embodiments that may be combined with any of the preceding embodiments, the cluster of highly hydrophobic amino acid residues is on the surface of the protein. In certain embodiments that may be combined with any of the preceding embodiments, the cluster was generated by applying the reverse Cuthill-McKee algorithm on pairs of highly hydrophobic amino acid residues that are less than the first defined distance apart.

In certain embodiments that may be combined with any of the preceding embodiments, the polar amino acid residues are charged-amino acid residues. In certain embodiments that may be combined with any of the preceding embodiments, the one or more solvent-exposed polar amino acid residues are identified from the structural model representing the protein, or portion thereof. In certain embodiments that may be combined with any of the preceding embodiments, the one or more solvent-exposed polar-amino acid residues have a solvent accessible area (SAA) greater than 50 $Å^2$, greater than 15 $Å^2$, greater than 20 $Å^2$, greater than 25 $Å^2$, greater than 30 $Å^2$, greater than 35 $Å^2$, greater than 40 $Å^2$, greater than 45 $Å^2$, or greater than 50 $Å^2$. In certain embodiments that may be combined with any of the preceding embodiments, the one or more solvent-exposed polar amino acid residues are on the surface of the protein. In certain embodiments that may be combined with any of the preceding embodiments, the second defined distance between a solvent-exposed polar-amino acid residue and at least one amino acid residue in the cluster of highly hydrophobic amino acid residues is at most 20 Å, at most 15 Å, at most 10 Å, at most 5 Å, at most 2 Å, or at most 1 Å. In certain embodiments that may be combined with any of the preceding embodiments, the method further includes selecting one or more of the solvent-exposed polar amino acid residues to be with within the cluster when the solvent-exposed charged-amino acid residues are within a distance of at most 10 Å, at most 9 Å, at most 8 Å, at most 7 Å, at most 6 Å, or at most 5 Å from a highly hydrophobic amino acid residue in the cluster.

In certain embodiments that may be combined with any of the preceding embodiments, the criterion for evolutionary conservation is a sequence-conservation threshold. In certain embodiments, the sequence-conservation threshold is a ConSurf score, a Jensen-Shannon divergence score, a BLAST score, or an AL2CO score. In certain embodiments, the sequence-conservation threshold is a ConSurf score. In certain embodiments, the ConSurf score is 0.3, 0.4, 0.5, 0.6, 0.7, 0.8, or 0.9. In certain embodiments, amino acid residues having a ConSurf score greater than 0.3, greater than 0.4, greater than 0.5, greater than 0.6, greater than 0.7, greater than 0.8, or greater than 0.9 do not meet the criterion for evolutionary conservation.

In certain embodiments that may be combined with any of the preceding embodiments, where the effective-hydrophobicity was calculated by: (a) electing an amino acid residue from the plurality of amino acid residues of the model; (b) calculating, for all side-chain atoms of the residue, a ratio of the solvent accessible area (SAA) of the atoms to the SAA of atoms in an identical residue which is fully exposed; and (c) multiplying each ratio by the hydrophobicity of the amino acid as determined by an amino acid hydrophobicity scale, whereby the product of step (c) is the effective-hydrophobicity of the amino acid residue. In certain embodiments, the effective-hydrophobicity was calculated for at least two, at least three, at least four, or at least five adjacent amino acid residues of the protein. In certain embodiments that may be combined with any of the preceding embodiments, the method further includes calculating SAAs on main chain atoms. In certain embodiments that may be combined with any of the preceding embodiments, attached hydrogen atoms are excluded from the SAA calculation. In certain embodiments that may be combined with any of the preceding embodiments, the structural model is processed prior to step (a) by performing a molecular dynamics simulation which optionally includes a solvent. In certain embodiments, the solvent is water. In certain embodiments that may be combined with any of the preceding embodiments, the molecular dynamics simulation is performed using a simulation package selected from ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD. In certain embodiments, the molecular dynamics simulation is performed using the CHARMM simulation package. In certain embodiments, the molecular dynamics simulation is performed using the NAMD simulation package. In certain embodiments that may be combined with any of the preceding embodiments, the effective-hydrophobicity is calculated by conducting a molecular dynamics simulation prior to step (a) and repeating steps (a)-(c), each time conducting a further molecular dynamics simulation at a plurality of time steps, thereby producing multiple sums as in step (c), and calculating the average of the sums, whereby the calculated average is the effective-hydrophobicity for the amino acid residue. In certain embodiments, the molecular dynamics simulation is performed using a simulation package selected from ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, and XMD. In certain embodiments, the molecular dynamics simulation is performed using the CHARMM simulation package. In certain embodiments, the molecular dynamics simulation is performed using the NAMD simulation package. In certain embodiments that may be combined with any of the preceding embodiments, the amino acid hydrophobicity scale is the Black and Mould hydrophobicity scale. In certain embodiments, the amino acid hydrophobicity scale is normalized such that glycine has a hydrophobicity of zero. In certain embodiments that may be combined with any of the preceding embodiments, the amino acid hydrophobicity scale is normalized such that phenylalanine has a hydrophobicity of 0.5. In certain embodiments that may be combined with any of the preceding embodiments, the amino acid hydrophobicity scale is normalized such that arginine has a hydrophobicity of −0.5.

Other aspects of the present disclosure provide a method to identify amino acid residues involved in macromolecule binding to a protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify hot-spot amino acid residues involved in macromolecule binding to the protein; and (c) outputting the hot-spot amino acid residues involved in macromolecule binding to the protein.

Other aspects of the present disclosure provide a method to identify a binding-region amino acid residues on the surface of a protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify binding-region amino acid residues on the surface of the protein; and (c) outputting the identified binding-region amino acid residues on the surface of the protein.

Other aspects of the present disclosure provide a method to identify hot-spot amino acid residues on the surface of a protein involved in macromolecule binding to the protein, by: (a) selecting an effective-hydrophobicity threshold; and (b) mapping onto a structural model representing the protein and containing a plurality of amino acid residues, the hot-spot amino acid residues of the protein predicted using the method of any of the preceding embodiments to identify hot-spot amino acid residues on the surface of the protein; and (c) outputting the identified hot-spot amino acid residues on the surface of the protein.

In certain embodiments that may be combined with any of the preceding embodiments, increasing the effective-hydrophobicity threshold increases identification accuracy. In certain embodiments that may be combined with any of the preceding embodiments, increasing the effective-hydrophobicity threshold reduces protein coverage.

DESCRIPTION OF THE FIGURES

The patent or application file contains at least one drawing executed in color. Copies of this patent or patent application publication with color drawings will be provided by the office upon request and payment of the necessary fee.

FIG. 1 depicts a method for predicting hot spot amino acid residues of a protein, or portion thereof.

FIG. 11A depicts accuracy and coverage of various methods for prediction of binding-region residues of GHR. Results for sSIM (green) and dSIM (red) are also shown for various values of $\Phi_{eff}$. Note that y-axis scale is 0-70%. FIG. 11B depicts accuracy and coverage of various methods for prediction of hot-spot residues of GHR. Results for sSIM (green) and dSIM (red) are also shown for various values of $\Phi_{eff}$. The values of theoretical maximum accuracy are given section S5. Note that y-axis scale is 0-20%.

Figure 2:
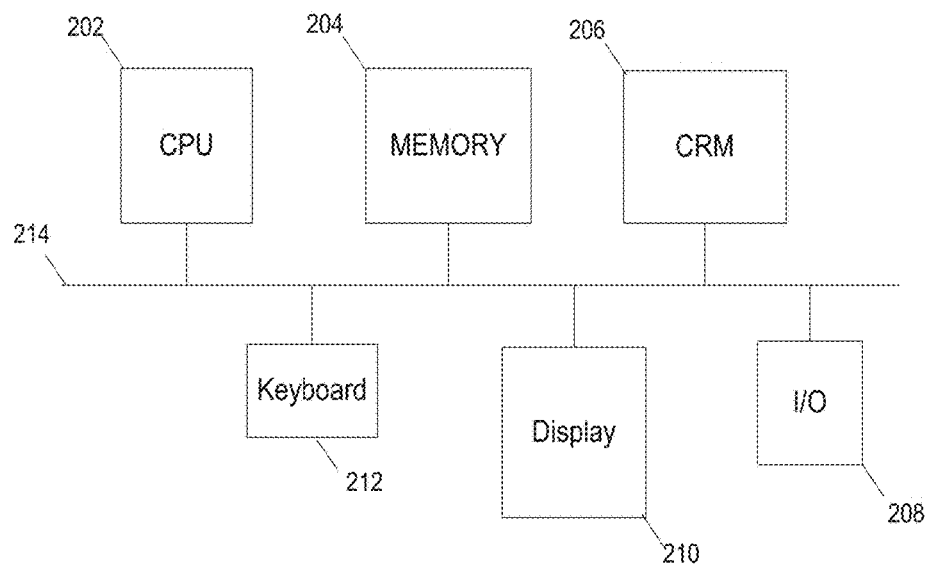
FIG. 2 depicts a block diagram of an exemplary computer system.

Results for sSIM (green) are also shown for various values of $\Phi_{eff}$. Binding-region residues for EGFR-EGF complex were identified using the structure PDB ID: 1IVO. Experimental data on determination of hot-spot residues for EGFR is not available.

DETAILED DESCRIPTION

Overview

The present disclosure relates to methods, such as computer-implemented methods, computer-readable storage media containing computer-executable instructions, and systems for predicting hot spot amino acid residues of a protein, or portion thereof, that utilize a structural model representing the protein, or portion thereof, to identify and select one or more clusters of highly hydrophobic amino acid residues having an effective-hydrophobicity greater than a chosen threshold, to identify and select one or more solvent-exposed polar amino acid residues within a defined distance of the one or more clusters, removing those amino acid residues that do not meet a criterion for evolutionary conservation from the selected one or more clusters and one or more solvent-exposed polar amino acid residues to produce a set of one or more predicted hot-spot amino acid residues, and storing the one or more predicted hot-spot amino acid residues. Moreover, the present disclosure is based, at least in part, on the development of a novel computational tool for accurately predicting hot spot residues using the structure of an unbound protein. Moreover, this novel computational tool identified hot spot residues with an accuracy that ranged from about 36% to about 57% (Tables 7 and 8). Advantageously, the accuracy of the disclosed tool was higher than existing computational tools including ISIS (2-26%), meta-PPISP (3-26%), and ConSurf (8-26%). This result is surprising, as this increase in accuracy is much higher than a mere incremental improvement over existing computational tools. Indeed, the lower end of the range of accuracy obtained by the disclosed tool (36%) is 10% higher than the highest percent accuracy obtained with ISIS, meta-PPISP, or ConSurf.

The present disclosure also addresses the unmet need to accurately identify hot-spot residues of a protein involved in binding with other macromolecules (e.g., protein-protein interactions), which binding is often mediated, at least in part, through clusters of hydrophobic residues and solvent-exposed polar amino acids within the vicinity of the clusters that can be readily identified using the methods disclosed herein.

Accordingly, one aspect of the present disclosure provide a computer-implemented method for predicting hot-spot amino acid residues of a protein, or portion thereof, where the protein, or portion thereof, is represented in a structural model containing a plurality of amino acid residues, by: (a) selecting from the plurality of amino acid residues of the model, a cluster of highly hydrophobic amino acid residues, where the cluster contains two or more amino acid residues each having an effective-hydrophobicity greater than a chosen threshold, and where each amino acid residue in the cluster is within a first defined distance of at least one other amino acid residue in the cluster; (b) selecting from the plurality of amino acid residues of the model, one or more solvent-exposed polar amino acid residues within a second defined distance of at least one amino acid residue in the cluster of highly hydrophobic amino acid residues; (c) removing from the cluster of highly hydrophobic amino acid residues and from the one or more solvent-exposed polar amino acid residues those amino acid residues that do not meet a criterion for evolutionary conservation, to produce a set of one or more predicted hot-spot amino acid residues; and (d) storing the one or more predicted hot-spot amino acid residues.

As used herein, a "hot spot amino acid residue" or "hot spot residue" refers to a binding-region amino acid residue of a protein, or portion thereof, that is a major contributor to the binding energy of the protein. For example, a hot-spot residue of a protein may contribute at least 1.3 kcal/mol to the binding energy of a binding interaction. Alternatively, mutating a hot spot residue to an alanine can result in at least 10-fold increase in the protein-protein dissociation constant ($K_D$).

FIG. 1 depicts a flow chart outline of an exemplary method 100 for predicting hot-spot amino acid residues of a protein.

In step 102, a cluster of highly hydrophobic amino acid residues is selected from a plurality of amino acid residues of a structural model representing a protein. Examples of such structural models are discussed below in the section "Protein Structural Model." Moreover, the cluster contains two or more amino acid residues each having an effective-hydrophobicity greater than a chosen threshold, and where each amino acid residue in the cluster is within a first defined distance of at least one other amino acid residue in the cluster. As disclosed herein, highly hydrophobic amino acid residues can be identified from the model by setting an effective-hydrophobicity threshold, calculating the effective-hydrophobicity of the amino acid residues of the protein, and identifying which residues have an effective-hydrophobicity that is greater than the threshold. Any disclosed algorithm for determining the effective-hydrophobicity may be used. This step and examples of such algorithms are discussed below in the section "Highly Hydrophobic Amino Acid Residues."

In step 104, one or more solvent-exposed polar amino acid residues within a defined distance of the cluster of highly hydrophobic amino acid residues are selected from the plurality of amino acid residues of the model. Any disclosed algorithm for identifying solvent-exposed polar amino acid residues may be used. This step and examples of such algorithms are discussed below in the section "Solvent-Exposed Polar Amino Acid Residues."

In step 106, amino acid residues that are not evolutionarily conserved are removed from the selected cluster of highly hydrophobic amino acid residues and from the selected one or more solvent-exposed polar amino acid residues to produce a set of one or more predicted hot-spot amino acid residues. In certain embodiments, removing the amino acid residues that do not meet a criterion for evolutionary conservation first involves identifying the amino acid residues of the protein that meet a criterion for evolutionary conservation. Any criterion known in the art for identifying amino acid residues having evolutionary conservation may be used. Preferably, a sequence conservation threshold is used to identify amino acid residues having evolutionary conservation. Any known sequence conservation threshold may be used. Preferably, the sequence conservation threshold is a ConSurf score. In further embodiments, amino acid residues within the selected cluster of highly hydrophobic amino acid residues and within the selected solvent-exposed polar amino acid residues that have evolutionary conservation are identified. This step and examples of sequence conservation thresholds are discussed below in the section "Evolutionary Amino Acid Residues."

In step 108, the one or more predicted hot-spot amino acid residue is stored. In certain embodiments, the predicted hot spot amino acid residues are presented to a user. In other embodiments, the predicted hot spot amino acid residues are presented as a contour map. In further embodiments, the contour map is a map of a structural binding pocket of the protein showing the location of the predicted hot spot amino acid residues.

Protein Structural Models

Certain aspects of the present disclosure relate to methods, such as computer-implemented methods, computer-readable storage media containing computer-executable instructions, and systems for predicting hot-spot amino acid residues by utilizing a structural model representing a protein, or portion thereof, for predicting hot-spot amino acid residues of the protein.

Suitable Proteins

By "protein" is meant any sequence of two or more amino acids, (also referred to herein as "amino acid residues" or "residues") joined together by peptide bonds between carboxyl and amino groups of adjacent amino acids, regardless of length, post-translation modification, chemical modification, or function. The terms "polypeptide," "peptide," and "protein" are used interchangeably herein. In preferred embodiments, the methods of the present disclosure are applied to a protein which is of sufficient length to fold into a three-dimensional structure. In some embodiments, the protein is a naturally occurring protein. In some embodiments, the protein is chemically synthesized. In some embodiments the protein is a recombinant protein, for example, a hybrid or chimeric protein. In some embodiments the protein is a complexed protein (e.g., complexed interacting proteins). Proteins can be isolated (e.g., from a natural source or chemical milieu). In some embodiments the protein may be a modified protein or a peptidomimetic. In some embodiments the protein may be a derivatized protein, for example, a chemically conjugated protein (including but not limited to polymer conjugated proteins (e.g., pegylated proteins). As used herein, the term "protein" also is intended to include protein fragments.

Indeed, it is envisioned that that the methods of the present disclosure may be applied to any amino acid based molecule for which a structural model is available or may be generated. For example, the methods described herein may be applied to modified proteins, or proteins which incorporate unusual or unnatural amino acids as described herein. In some embodiments, the structures of unusual, unnatural, or modified amino acids may be computationally substituted or inserted into a structural model for application of the methods described herein. Methods of experimentally designing peptide analogs, derivatives and mimetics are known in the art. For example, see Farmer, P. S. in Drug Design (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113-11123; Smith, A. B. 3rd, et al. (1994) *J. Am. Chem. Soc.* 116:9947-9962; and Hirschman, R., et al. (1993) *J. Am. Chem. Soc.* 115:12550-12568.

A great number and variety of peptide, polypeptide, and protein therapeutic agents are known in the art, and are expected to benefit from the methods of the present invention. These therapeutic agents contain several very broad classes, including, without limitation, hormones, proteins, bait peptides, antigens, immunoglobulins, repressors/activators, targets of small molecules, enzymes, cytokines, chemokines, myokines, lipokines, growth factors, receptors, receptor domains, neurotransmitters, neurotrophins, interleukins, and interferons among others.

Protein Structural Models

As used herein a protein "structural model" is a representation of a protein's three-dimensional secondary, tertiary, and/or quaternary amino acid residue structure. A structural model encompasses X-Ray crystal structures, NMR structures, theoretical protein structures, structures created from homology modeling, Protein Tomography models, and atomistic models built from electron microscopic studies.

Typically, a "structural model" will not merely encompass the primary amino acid sequence of a protein, but will provide coordinates for the atoms in a protein in three-dimensional space, thus showing the protein folds and amino acid residue positions. In some embodiments, the structural model analyzed is an X-Ray crystal structure, e.g., a structure obtained from the Protein Data Bank (PDB, rcsb.org/pdb/home/home.do) or a homology model built upon a known structure of a similar protein.

A "theoretical protein structure" is a three-dimensional protein structural model that is created using computational methods often without any direct experimental measurements of the protein's native structure. A "theoretical protein structure" encompasses structural models created by ab-initio methods and homology modeling. A "homology model" is a three-dimensional protein structural model which is created by homology modeling, which typically involves comparing a protein's primary sequence to the known three dimensional structure of a similar protein. Homology modeling is well known in the art and is described in Kolinski et al., *Proteins* 1999; 37(4):592-610; Rost et al., *Protein Sci.* 1996; 5(8):1704-1718, and U.S. Pat. Nos. 7,212,924; 6,256,647; and 6,125,331. In particular, Xiang (*Curr Protein Pept Sci.* 2006 June; 7(3):217-27) provides an excellent description and review of homology modeling techniques which may be used to generate structures useful for the methods of the present invention.

Indeed, any homology modeling algorithms known in the art may be used according to the present methods, e.g., MODELLER (Eswar, et al., Comparative Protein Structure Modeling With MODELLER. *Current Protocols in Bioinformatics*, John Wiley & Sons, Inc., Supplement 15, 5.6.1-5.6.30, 200.), SEGMOD/ENCAD (Levitt M. J Mol Biol 1992; 226:507-533), SWISS-MODEL (Schwede T, Kopp J, Guex N, Peitsch M C. *Nucleic Acids Research* 2003; 31:3381-3385.), 3D-JIGSAW (Bates et al., *Proteins: Structure, Function and Genetics*, Suppl 2001; 5:39-46), NEST (Xiang. *Curr Protein Pept Sci.* 2006 June; 7(3): 217-227), VMD (Humphrey et al., *Journal of Molecular Graphics* 1996, February; 14(1):33-8, 27-8), and BUILDER (Koehl and Delarue. *Curr Opin Struct Biol* 1996; 6(2):222-226.). For antibodies in particular, the structure of antibody variable regions can be obtained accurately using the canonical structures method (Chothia C and Lesk A M, *J. Mol. Biol.* 1987, 196, 901; Chothia C et al., Nature 1989, 342, 877).

In particular embodiments, homology modeling may be used to assemble full proteins from known structure fragments, such as when an antibody Fab fragment is modeled onto an Fc fragment, or when a Fab fragment is created as a theoretical protein structure and modeled onto a Fc fragment crystal structure. A skilled artisan will understand that various possibilities exist. In one particular embodiment a Fab fragment may be modeled onto various antibody Fc structures of different classes or isotypes.

Ab initio models may also be employed in the methods of the present invention. An "ab initio protein structural model" is a protein structural model which is created directly from the protein primary sequence by simulating the protein folding process using the equations known in physical chemistry (Bonneau and Baker. *Annual Review of Biophysics and Biomolecular Structure.* 2001, Vol. 30, Pages 173-189; Lesk Proteins 1997; 1:151-166. Suppl; Zemla, et al., *Proteins* 1997; 1:140-150. Suppl; Ingwall et al., *Biopolymers* 1968; 6:331-368; U.S. Pat. Nos. 6,832,162, 5,878,373, 5,436,850, 6,512,981, 7,158,891, and 6,377,893; and U.S. patent application Ser. Nos. 9/788,006; 11/890,863; and 10/113,219, which are all incorporated herein by reference). Typically, experimentally determined structures (e.g., X-Ray crystal structures) and homology models are preferable to ab initio models, since the difficulty in simulating de novo protein folding may, in some cases, lead to imprecise protein structural models.

It is understood that any method known in the art to generate a theoretical protein structure may be useful in accordance with the methods, such as computer-implemented methods, computer-readable storage media containing computer-executable instructions, and systems of the present disclosure. In addition to the methods described above, methods such as those described in the meeting, Critical Assessment of Techniques for Protein Structure Prediction (CASP) may be used in accordance with the present disclosure. Various examples are described in proceedings to CASP, e.g., in the publications related to the 7th Community Wide Experiment on the Critical Assessment of Techniques for Protein Structure Prediction Asilomar Conference Center, Pacific Grove, Calif. Nov. 26-30, 2006 and also in CASP6 proceedings. Proteins: Structure, Function, and Bioinformatics. 2005. 61(57):1-236; CASP5 proceedings. Proteins: Structure, Function, and Genetics. 2003, 53(56):333-595; CASP4 proceedings. Proteins: Structure, Function, and Genetics. 2001, 45(55):1-199; CASP3 proceedings Proteins: Structure, Function, and Genetics, 1999, 37(53):1-237 (1999).

Additional examples of protein structure modeling algorithms that may be used with the methods of the present disclosure include, without limitation, SwissModel, ModWeb, I-Tasser, Robetta, HHPred, Modeller, SCWRL3, WhatIf, and Rosetta. Further non-limiting examples of suitable protein structure modeling algorithms include those described in Battey J N, et al., *Proteins* 69(S8): 68-82, 2007.

Structural Model Pre-processing

In some embodiments, the structural model may be pre-processed before applying the methods of the present disclosure. For example, molecular dynamics simulation technology may be utilized with the structural model to allow the protein side chains to reach a more natural conformation, or the structural model may be allowed to interact with solvent, e.g., water, in a molecular dynamics simulation.

In practice, any simulation technique/package that samples conformational space may be used according to the methods described herein. The preferred mode of molecular simulation is a molecular dynamics simulation (MDS). An MDS is a mathematical simulation where the atoms in a molecular structure are allowed to move and interact according to the laws of physics, e.g., the chemical bonds within proteins may be allowed to flex, rotate, bend, or vibrate as allowed by the laws of chemistry and physics. Interactions such as electrostatic forces, hydrophobic forces, van der Waals interactions, interactions with solvent and others may also be modeled in MDS simulations. Such simulations allow one of skill in the art to observe the protein structure as it might appear when solvated, or take more accurate measurements on the protein structure by averaging multiple measurements at various points during the simulation. In a preferred embodiment, the molecular simulation is conducted using the CHARMM simulation package (Brooks et al. *J. Comput. Chem.* 1983, 4, 187). In another preferred embodiment the molecular simulation is conducted using the NAMD package (Phillips et al. *Journal of Computational Chemistry* 2005, 26, 1781). One of skill in the art will understand that multiple packages may be used, e.g., the CHARMM package may be employed for setting up or preprocessing a protein structural model, solvating the structure, etc, and the NAMD package may be employed for the simulations which become part of the hot-spot amino acid residue calculations. Any of the numerous methodologies known in the art to conduct MDS simulations may be used in accordance with the methods of the present disclosure. The following publications describe multiple methodologies which may be employed: Guvench and MacKerell. *Methods Mol Biol.* 2008; 443:63-88; Norberg and Nilsson. *Q Rev Biophys.* 2003 August; 36(3):257-306; U.S. Pat. Nos. 5,424, 963; 7,096,167; and U.S. patent application Ser. Nos. 11/520,588; and 10/723,594.

In particular, the following software packages may be employed for molecular dynamics simulations: ABINIT (Gonze et al. *Comput. Mat. Science.* 2002, 25, 478; Gonze et al. *Kristallogr.* 2005, 220, 558; abinit.orgf); AMBER (Duan et al. *Journal of Computational Chemistry.* 2003, 24(16):1999-2012; amber.scripps.edu); Ascalaph (agilemolecule.com/Products.html, Jun. 19, 2008); CASTEP (Segall, et al. *J. Phys.: Cond. Matt.* 2002, 14(11):2717-2743; Clark et al. *Zeitschrift für Kristallographie.* 2005, 220(5-6) pp. 567-570; castep.org); CPMD (CMPD manual for CMPD version 3.11.0, Mar. 29, 2006; cpmd.org/manual.pdf); CHARMM (Brooks et al. *J Comp Chem.* 1983, 4:187-217; charmm.org); DL_POLY (Todorov & Smith, THE DL POLY 3 USER MANUAL. STFC Daresbury Laboratory. Version 3.09.3, February 2008; cse.scitech.ac.uk/ccg/software/DL_POLY/MANUALS/USRMAN3.09.pdf); FIREBALL (fireball.phys.wvu.edu/LewisGroup/fireball-Home.html); GROMACS (Van Der Spoel, et al., *J Comput Chem.* 2005, 26(16): 1701-18; Hess, et al, *J Chem Theory Comput.* 2008, 4(2): 435; gromacs.org); GROMOS (Schuler, Daura, van Gunsteren. *Journal of Computational Chemistry.* 2001, 22(11):1205-1218; igc.ethz.ch/GROMOS/index); LAMMPS (Plimpton, J Comp Phys. 1995, 117, 1-19; lammps.sandia.gov); MDynaMix (Lyubartsev and Laaksonen. *Computer Physics Communications.* 2000, 128, 565-589); MOLDY (Moldy: a portable molecular dynamics simulation program for serial and parallel computers., *Computer Physics Communications.* 2000, 126(3):309-328; earth.ox.ac.uk/~keithr/moldy.html); MOSCITO (Dietmar Paschek and Alfons Geiger. User's Guide and Manual, MOSCITO 4, Performing Molecular Dynamics Simulations, Apr. 7, 2003, ganter.chemie.uni-dortmund.de/MOSCITO/manual4.pdf); NAMD (Kumar, et al. *IBM Journal of Research and Development.* 2007, Volume 52, No. 1/2; Phillips et al., *Proceedings of SC* 2002; charm.cs.uiuc.edu/research/moldyn/); Newton-X (M. Barbatti, G. Granucci, M. Ruckenbauer, M. Persico, H. Lischka, Newton-X: a package for Newtonian dynamics close to the crossing seam, version 0.15b, 2007; univie.ac.at/newtonx; Barbatti, et al., *J. Photochem. Photobio. A* 190, 228 (2007)); ProtoMol (Matthey, et al. *ACM Trans. Math. Softw.,* 2004, 30(3):237-265; protomol.sourceforge.netf); PWscf (User's Guide for Quantum- ESPRESSO version 3.2, pwscf.org/guide/3.2.3/users-guide-3.2.3.pdf); SIESTA (Soler, et al. *Journal of Physics: Condensed Matter.* 2002, 14: 2745-2779); VASP (Georg Kresse and Jürgen Furthmüller, VASP the GUIDE, Institut für Materialphysik, Universität Wien, Sensengasse 8, A-1130 Austria, Vienna, Mar. 1, 2007; cms.mpi.univie.ac.at/vasp/); TINKER (Ren and Ponder. *J. Phys. Chem. B.* 2003, 107, 5933-5947; dasher.wustl.edukinker/); YASARA (Krieger, et al., *Proteins.* 2002 47(3):393-402.); ORAC (Procacci, et al., *Phys. Chem.* 1996, 100 10464-10469; chim.unifi.it/orac/); XMD (XMD online manual, XMD—Molecular Dynamics Program Jon Rifkin, v2.5.30 20 Jan. 2002); VMD (Humphrey et al., *Journal of Molecular Graphics* 1996, February; 14(1):33-8, 27-8); and CHARM22 (McKerell et al., *J. Phys. Chem. B* 1998, 102, 3586-3616).

The pre-processing is not limited to molecular dynamics simulation and can be accomplished using any art-recognized means to determine movement of a protein in solution. An exemplary alternative simulation technique is Monte Carlo simulation. Simulations can be performed using simulation packages or any other acceptable computing means. In certain embodiments, simulations to search, probe, or sample protein conformational space can be performed on a structural model to determine movement of the protein.

Highly Hydrophobic Amino Acid Residues

Other aspects of the present disclosure relate to methods, such as computer-implemented methods, computer-readable storage media containing computer-executable instructions, and systems for predicting hot-spot amino acid residues by utilizing a protein structural model of the present disclosure to identify and select one or more clusters of highly hydrophobic amino acid residues, where the clusters each contain two or more amino acid residues each having an effective-hydrophobicity greater than a chosen threshold, and where each amino acid residue in the cluster is within a first defined distance of at least one other amino acid residue in the cluster.

In certain embodiments, the two or more highly hydrophobic amino acid residues are three or more highly hydrophobic amino acid residues, four or more highly hydrophobic amino acid residues, five or more highly hydrophobic amino acid residues, six or more highly hydrophobic amino acid residues, seven or more highly hydrophobic amino acid residues, eight or more highly hydrophobic amino acid residues, nine or more highly hydrophobic amino acid residues, 10 or more highly hydrophobic amino acid residues, 11 or more highly hydrophobic amino acid residues, 12 or more highly hydrophobic amino acid residues, 13 or more highly hydrophobic amino acid residues, 14 or more highly hydrophobic amino acid residues, 15 or more highly hydrophobic amino acid residues, 20 or more highly hydrophobic amino acid residues, or 25 or more highly hydrophobic amino acids.

In other embodiments, the selected one or more clusters of highly hydrophobic amino acid residues are on the surface of the protein.

Effective-hydrophobicity of Amino Acid Residues

As used herein, selecting one or more clusters of highly hydrophobic amino acid residues of a protein, or portion thereof, involves identifying one or more highly hydrophobic amino acid residues from a protein structural model of the protein. Preferably, one or more highly hydrophobic amino acid residues are identified on the surface of the protein. Any method known in the art for identify highly hydrophobic amino acid residues may be used.

In certain preferred embodiments, highly hydrophobic amino acid residues of a protein, or portion thereof, are identified by assigning an effective hydrophobicity value for each of one or more amino acid residues of the protein. Preferably, effective hydrophobicity values are assigned for every amino acid residue of the protein. As disclosed herein, if the effective hydrophobicity value of a given amino acid residue is greater than a chosen threshold value, the amino acid residue is identified as being a highly hydrophobic amino acid residue.

As used herein, the "effective-hydrophobicity" of an amino acid residue refers to the hydrophobicity value for an amino acid residue of a protein, or portion thereof, which has been normalized to account for its fractional solvent-accessible-area (SAA). As such, any buried amino acid residue of the protein would have an effective hydrophobicity of zero.

Amino Acid Residue Hydrophobicity

Any method known in the art for calculating amino acid residue hydrophobicity may be utilized with the methods of the present disclosure. For example a hydrophobicity scale may be used to determine the hydrophobicity of an amino acid residue. Additionally, partitioning methods, accessible surface area methods, chromatographic methods, and physical property methods may be used to determine amino acid residue hydrophobicity.

Accordingly, in certain embodiments, amino acid residue hydrophobicity is calculated, in part, using an amino acid hydrophobicity scale known in the art. In a preferred embodiment, the amino acid hydrophobicity scale is the scale set forth in Black and Mould, *Anal. Biochem.* 1991, 193, 72-82. In general, according to the Black and Mould, amino acid hydrophobicity progresses as follows (beginning with the most hydrophobic residues): Phe>Leu=Ile>Tyr≈Trp>Val>Met>Pro>Cys>Ala>Gly>Thr>Ser>Lys>Gln>Asn>His>Glu>Asp>Arg. The scaled values for hydrophobicity, as reported by Black and Mould are shown in Table 1 below.

TABLE 1

| AA Residue | Hydrophobicity |
|---|---|
| Ala | 0.616 |
| Cys | 0.68 |
| Asp | 0.028 |
| Glu | 0.043 |
| Phe | 1 |
| Gly | 0.501 |
| His | 0.165 |
| Ile | 0.943 |
| Lys | 0.283 |
| Leu | 0.943 |
| Met | 0.738 |
| Asn | 0.236 |
| Pro | 0.711 |
| Gln | 0.251 |
| Arg | 0 |
| Ser | 0.359 |
| Thr | 0.45 |
| Val | 0.825 |
| Trp | 0.878 |
| Tyr | 0.88 |
| Asx | 0.132 |
| Glx | 0.147 |

In practice, any art recognized scale of amino acid hydrophobicity may be employed by the methods of the present disclosure to determine the hydrophobicity of an amino acid residue. Thus, although the scale described in Table 1 may be used during the calculation of the effective-hydrophobicity, other scales known in the art may be substituted. The recent review by Biswas et al. (*J. Chromatogr. A* 1000

(2003) 637-655) describes a variety of hydrophobicity scales which may be used in accordance with the present disclosure.

In addition to amino acid residue hydrophobicity, the methods, such as computer-implemented methods, computer-readable storage media containing computer-executable instructions, and systems described herein may also assign a hydrophobicity value to an atom within a protein or protein structural model. In one embodiment, the "atom hydrophobicity" is a ratio of the hydrophobicity of the amino acid which contains the atom and the number of atoms in the amino acid, or more preferably, the number of atoms in the amino acid side chain. In a similar embodiment, the "atom hydrophobicity" may be a fraction of the residue hydrophobicity which is proportional to the size, surface area, or volume of the atom in question. For example, if an oxygen atom composes 5% of the volume of an amino acid residue, the atom hydrophobicity of the oxygen atom will be 5% of the hydrophobicity of the amino acid residue. In another embodiment the atom hydrophobicity may be a fraction of the residue hydrophobicity equivalent to or proportional to the fraction of the surface area that the atom contributes to the amino acid residue. In related embodiments, the hydrophobicity weight (i.e., the fraction of residue hydrophobicity) assigned to an atom may reflect the fraction of volume the atom takes up in the residue, the mass weight of the atom in the residue, the contribution of the atom to hydrophobicity, etc. As described above, the amino acid hydrophobicity is determined according to a hydrophobicity scale known in the art.

Effective-hydrophobicity Threshold Values

As used herein, a "highly hydrophobic amino acid residue" refers to an amino acid residue having an effective-hydrophobicity value that is greater than a chosen threshold value. The threshold value may be varied to control the hot-spot amino acid residue prediction accuracy for a protein, or portion thereof, and hot-spot amino acid residue prediction coverage for a protein. As used herein, the prediction accuracy increases as the threshold value increases, while prediction coverage decreases as the threshold value increases. Any methods known in the art for calculating accuracy and coverage may be used. In one non-limiting example, accuracy may be calculated as the ratio of the number of the correctly predicted residues to the total number of predicted hot-spot residues, and the coverage may be calculated as the ratio of the number of correctly predicted residues to the number of experimentally observed residues.

In certain embodiments, the threshold value can be varied to control the number of predicted hot-spot amino acid residues of a protein, or portion thereof. For example, when the threshold value is very large, only a small number of residues are predicted. However, at moderate threshold values, a large number of residues are predicted. In certain embodiments, when the threshold value is set to zero, even fully buried amino acid residues are predicted to be hot-spot amino acid residues. Moreover, when the threshold value is below zero, e.g., −0.5, all the conserved amino acid residues in the protein are predicted to be hot-spot amino acid residues.

Accordingly, in certain embodiments, the threshold value ranges from about 0.1 to about 0.50, from about 0.1 to about 0.40, from about 0.1 to about 0.30, or from about 0.1 to about 0.20. In other preferred embodiments, the threshold value is about 0.10, 0.15, 0.20, 0.25, 0.30, 0.35, 0.40, 0.45, or 0.50.

In certain embodiments, the accuracy of the methods, such as computer-implemented methods, computer-readable storage media containing computer-executable instructions, and systems of the present disclosure for predicting hot-spot amino acid residue may include repeating the step of selecting a cluster of highly hydrophobic amino acid residues utilizing increasingly higher threshold values.

Calculating Effective-hydrophobicity

Any method known in the art for normalizing the hydrophobicity value of an amino acid residue to account for its fractional solvent-accessible-area (SAA) may be utilized to determine the effective-hydrophobicity of the amino acid residue.

For example, the method described in Chennamsetty et al. (*Proc. Natl. Acad. Sci. U.S.A.* 106, 11937-11942) can be used to calculate the effective-hydrophobicty. In particular the effective-hydrophobicity ($\Phi_{eff}$) of an amino acid residue of a protein, or portion thereof, can be determined by calculating the hydrophobicity of the fraction of the amino acid which is exposed according to the formula below:

$$\Phi_{eff} = \left( \frac{SAA \text{ of side chain atoms of residue}}{SAA \text{ of side chain atoms of fully exposed residue}} \right) \times \text{Residue Hydrophobicity}$$

The above formula is based, at least in part, on the calculation of the Effective-SAA (Solvent Accessible Area), which is a ratio of the SAA of the side chain atoms of an amino acid residue to the SAA of side chain atom in an identical amino acid residue that is fully exposed. The SAA is known in the art for characterizing the surface of a protein. SAA gives the surface area of each amino acid or protein structure that is in contact with the solvent. SAA may be typically calculated by computing the locus of the center of a probe sphere as it rolls over the protein surface, i.e., the surface of a protein structural model. The probe sphere has the same radius as that of a water molecule, R=1.4 Å. Alternative methods of calculating SAA, are known in the art and are compatible with the methods described herein.

A residue which is "fully exposed" is a residue, X, in the fully extended conformation of the tripeptide Ala-X-Ala. One of skill in the art will appreciate that this arrangement is designed such that a calculation of SAA on such a residue, X, will yield the maximum solvent accessible area available. Accordingly, it is contemplated that other residues besides alanine may be used in the calculation without wholly disrupting or altering the results. In certain embodiments, the SAA of side chain atoms of a fully exposed residue (e.g., for amino acid X) is obtained by calculating the SAA of side-chain atoms of the middle residue in the fully extended conformation of the tripeptide Ala-X-Ala.

Moreover, the hydrophobicity of the amino acid residue can be obtained by any of the methods for determining amino acid residue hydrophobicity disclosed herein. In certain preferred embodiments, the hydrophobicity of the amino acid is obtained from the hydrophobicity scale of Black and Mould. In certain embodiments, the Black and Mould hydrophobicity scale is normalized such that glycine has a hydrophobicity of zero. Thus, amino acid residues more hydrophobic than glycine (e.g., Ala, Cys, Pro, Met, Val, Trp, Tyr, Ile, Leu, Phe) have a positive effective-hydrophobicity value, and residues less hydrophobic than glycine (e.g., Thr, Ser, Lys, Gln, Asn, His, Glu, Asp, Arg) have a negative effective-hydrophobicity value. In other embodiments, the hydrophobicity scale is further normalized such that the most hydrophobic residue (i.e., Phe) has a value of 0.5, and the least hydrophobic residue (i.e., Arg) has a value of −0.5.

Accordingly, the effective-hydrophobicity of an amino acid residue can be calculated by: (a) selecting an amino acid residue from the plurality of amino acid residues of a structural model representing the protein, or portion thereof; (b) calculating, for all side-chain atoms of the residue, a ratio of the solvent accessible area (SAA) of the atoms to the SAA of atoms in an identical residue which is fully exposed; and (c) multiplying each ratio by the hydrophobicity of the amino acid as determined by an amino acid hydrophobicity scale, whereby the product of step (c) is the effective-hydrophobicity of the amino acid residue. Additionally, the effective-hydrophobicity can be calculated for at least two, at least three, at least four, at least five, or more (e.g., two, three, four, five, etc.) amino acid residues that are adjacent to one another within the primary amino acid sequence of a protein. In certain embodiments, calculating the effective-hydrophobicity may further include optionally calculating SAAs on main chain atoms (i.e., those atoms of the peptide backbone and associated hydrogens). Preferably, hydrogen atoms are excluded from the SAA calculation. In other embodiments, calculating the effective-hydrophobicity may further include optionally conducting a molecular dynamics simulation prior to step (a) and repeating steps (a)-(c), each time conducting a further molecular dynamics simulation at a plurality of time steps, thereby producing multiple sums as in step (c), and calculating the average of the sums; whereby the calculated average is the effective-hydrophobicity for the amino acid residue.

In certain embodiments, the structural model can be processed prior to calculating the effective-hydrophobicity. Any of the methods for processing a structural model described above in the section entitled "Structural model pre-processing" may be used. For example the structural model may be processed by performing a molecular dynamics simulation which optionally includes a solvent, such as water. The molecular dynamics simulation may be performed using a simulation software package, such as ABINIT, AMBER, Ascalaph, CASTEP, CPMD, CHARMM, DL_POLY, FIREBALL, GROMACS, GROMOS, LAMMPS, MDynaMix, MOLDY, MOSCITO, NAMD, Newton-X, ProtoMol, PWscf, SIESTA, VASP, TINKER, YASARA, ORAC, or XMD. Preferably, the simulation software package is the CHARMM simulation package. In other preferred embodiments, the simulation software package is the NAMD simulation package.

Defined Distance between Highly Hydrophobic Amino Acid Residues

As disclosed herein, a cluster of highly hydrophobic amino acid residues of a protein, or portion thereof, refers to two or more highly hydrophobic amino acid residues of the protein that are each within a defined distance of at least one other highly hydrophobic amino acid residue in the cluster, where the defined distance determines the boundary of the cluster.

Any method known in the art for determining the distance between amino acid residues may be used to determine the distance between each amino acid residue in a cluster. For example, the distance between two amino acid residues may be determined to be the least distance between any two atoms of the two residues. Accordingly, in certain embodiments the defined distance between two or more amino acid residues in a cluster ranges from about 1 Å to about 15 Å. In other embodiments, the defined distance between two or more amino acid residues in a cluster is at most 15 Å, at most 14 Å, at most 13 Å, at most 12 Å, at most 11 Å, at most 10 Å, at most 9 Å, at most 8 Å, at most 7 Å, at most 6 Å, at most 5 Å, at most 4 Å, at most 3 Å, at most 2 Å, or at most 1 Å. Preferably, the defined distance between two or more amino acid residues in a cluster is at most 10 Å.

Generally, a distance of 10 Å between two highly amino acid residues corresponds approximately to the lower limit of the size of a protein-protein interface. Thus, in certain preferred embodiments, a distance of 10 Å is used as a cutoff value for determining whether a highly hydrophobic amino acid residue is within a cluster.

Alternatively, smoothing functions may be used to determine the boundary of a cluster of highly hydrophobic amino acid residues. Any smoothing function known in the art may be used. For example suitable smoothing functions include, without limitation, exponential functions and hyperbolic tangent functions. In one non-limiting example, the function $(0.5+0.5 \tan h(10 k)$, where $k>0)$ or $(0.5+0.5 \operatorname{erf}(10 k)$, where $k>0)$ may be used to define a smoother boundary at $R=10$ Å.

Selecting Clusters of Highly Hydrophobic Amino Acid Residues

Clusters of highly hydrophobic amino residue clusters may be selected using any clustering algorithm known in the art. For example any of the clustering algorithms disclosed in Xu and Wunsch, 2010 may be used (Xu and Wunsch, Clustering algorithms in biomedical research: a review, *IEEE Reviews in Biomedical Research*, 2010, vol 3, 120-154). Other examples of suitable clustering algorithms include, without limitation, the reverse Cuthill-McKee algorithm, the k-means algorithm, the DBSCAN algorithm, the Canopy algorithm, and the CLIQUE algorithm. Preferably, the reverse Cuthill-McKee algorithm is used to select one or more clusters of highly hydrophobic amino acid residues.

Solvent-Exposed Polar Amino Acid Residues

Other aspects of the present disclosure relate to methods, such as computer-implemented methods, computer-readable storage media containing computer-executable instructions, and systems for predicting hot-spot amino acid residues that utilize a protein structural model of the present disclosure to identify and select one or more solvent-exposed polar amino acid residues that are within a second defined distance of at least one amino acid residue in a selected cluster of highly hydrophobic amino acid residues. In certain embodiments, the one or more solvent-exposed polar amino acid residues are on the surface of the protein, or portion thereof.

As used herein, a "solvent-exposed polar amino acid residue" refers to a polar amino acid residue of a protein, or portion thereof, that is accessible to a solvent (i.e., is not buried). Any method for distinguishing a buried amino acid residue from a solvent-exposed polar amino acid residue known in the may be used. For example, a solvent accessible area (SAA) cutoff value of 10 Å$^2$ may be used to distinguish between solvent-exposed residues and buried residues.

Accordingly, the one or more solvent-exposed polar amino acid residues may each have a solvent accessible area (SAA) that ranges from about 10 Å$^2$ to about 50 Å$^2$. In certain embodiments, the one or more solvent-exposed polar amino acid residues each have a solvent accessible area (SAA) that is greater than 10 Å$^2$, greater than 11 Å$^2$, greater than 12 Å$^2$, greater than 13 Å$^2$, greater than 14 Å$^2$, greater than 15 Å$^2$, greater than 16 Å$^2$, greater than 17 Å$^2$, greater than 18 Å$^2$, greater than 19 Å$^2$, greater than 20 Å$^2$, greater than 25 Å$^2$, greater than 30 Å$^2$, greater than 35 Å$^2$, greater than 40 Å$^2$, greater than 45 Å$^2$, greater than 50 Å$^2$, or more.

Examples of suitable solvent-exposed polar amino acid residues include, without limitation, polar amino acid residues that are uncharged and polar amino acid residues having a net charge (i.e., charged amino acid residues).

Polar uncharged amino acid residues include, without limitation, asparagine (Asn), cysteine (Cys), glutamine (Gln), serine (Ser), threonine (Thr), and tyrosine (Tyr). Polar uncharged amino acid residues may also include, without limitation, modified amino acid residues, unusual amino acid residues, and unnatural amino acid residues. Additionally, under extreme conditions, such as extreme pH, charged amino acid residues of the present disclosure may become uncharged. The pH at which a given uncharged amino acid residue will become charged will depend on the isoelectric point (pI) of the amino acid. For example the pI of Tyr is 5.66. Thus, at a pH value of less than 5.66, Tyr will have a net charge. Methods of determining the pI of an amino acid are well known in the art.

Charged amino acid residues include, without limitation, arginine (Arg), aspartic acid (Asp), glutamic acid (Glu), histidine (His), and lysine (Lys). Charged amino acid residues may also include, without limitation, modified amino acid residues, unusual amino acid residues, and unnatural amino acid residues. Additionally, under extreme conditions, such as extreme pH, polar uncharged amino acid residues of the present disclosure may become charged. The pH at which a given charged amino acid residue will become uncharged will depend on the isoelectric point (pI) of the amino acid. For example the pI of Lys is 10. Thus, at a pH value 10 or more, Lys will not have a net charge.

Amino acid residue net charge under various conditions may be calculated using any algorithm for determining net charge known in the art. In one non-limiting example, the PROPKA algorithm can be used to compute the net charge (i.e., pKa) of each amino acid residue of a protein, or fragment thereof, when the protein is present at a non-neutral pH (Bas et al., *Proteins* 73: 765-783, 2008). Additional known methods for calculating the pKa of amino acid residues include, without limitation, those listed in Sham Y Y, et al. *J Phys Chem B* 1997; 101:4458-4472; Warshel A. *Accounts Chem Res* 1981; 14:284-290; Demchuk E, and Wade R C. *J Phys Chem* 1996; 100:17373-17387; Nielsen J E, and Vriend G. *Proteins* 2001; 43:403-412; Karshikoff A. *Protein Eng* 1995; 8:243-248; Antosiewicz J, et al. *Biochemistry* 1996; 35:7819-7833; Antosiewicz J, et al. *J Comput Chem* 1996; 17:1633-1644; Antosiewicz J, et al. *J Mol Biol* 1994; 238:415-436; Bashford D, and Karplus M. *Biochemistry* 1990; 29:10219-10225; Mehler E L, and Guarnieri F. *Biophys J* 1999; 77:3-22; Ullmann G M, and Knapp E W. *Eur Biophys J Biophys Lett* 1999; 28:533-551; Wisz M S, and Hellinga H W. *Proteins* 2003; 51:360-377; Yang A S, at al. *Proteins* 1993; 15:252-265; Havranek J J, and Harbury P B. *Proc Natl Acad Sci USA* 1999; 96:11145-11150; Nielsen J. *Protein Sci* 2003; 12:1894-1901; Barth P, et al. *Proc Natl Acad Sci USA* 2007; 104:4898-4903; Godoy-Ruiz R, et al. *Biophys Chem* 2005; 115:263-266; He Y, et al. *Proteins Struct Funct Bioinf* 2007; 69: 75-82; Khandogin J, and Brooks C L. *Biochemistry* 2006; 45: 9363-9373; Nielsen J E. *J Mol Graphics Model* 2007; 25:691-699; Simonson T, et al. *J Am Chem Soc* 2004; 126:4167-4180; Tynan-Connolly B M, and Nielsen J E. *Protein Sci* 2007; 16:239-249; Del Buono G S, et al. *Proteins Struct Funct Genet* 1994; 20:85-97; and Warshel A, et al. *Biochemistry* 1986; 25:8368-8372.

Alternatively, solvent-exposed amino acid residues within a defined distance of at least one amino acid residue in a cluster of highly hydrophobic amino acid residues of a protein, or portion thereof, can be identified and selected by calculating the solvent-accessible area from the structure of the protein. Any protein structural model software package of the present disclosure may be used to calculate the solvent-accessible area of the protein, or portion thereof. In certain embodiments, VMD (visual molecular dynamics) is used to calculate the solvent-accessible area of the protein.

Defined Distances of Solvent-exposed Polar Amino Acid Residues

As disclosed herein, selecting one or more solvent-exposed polar amino acid residues involves determining whether the one or more solvent-exposed polar amino acid residues are within a defined distance of at least one amino acid residue in a selected cluster of highly hydrophobic amino acid residues. In certain embodiments, the defined distance serves as a cutoff value for selecting the one or more solvent-exposed polar amino acid residues.

In certain embodiments, the one or more solvent-exposed polar amino acid residues are two or more solvent-exposed polar amino acid residues, three or more solvent-exposed polar amino acid residues, four or more solvent-exposed polar amino acid residues, five or more solvent-exposed polar amino acid residues, six or more solvent-exposed polar amino acid residues, seven or more solvent-exposed polar amino acid residues, eight or more solvent-exposed polar amino acid residues, nine or more solvent-exposed polar amino acid residues, 10 or more solvent-exposed polar amino acid residues, 11 or more solvent-exposed polar amino acid residues, 12 or more solvent-exposed polar amino acid residues, 13 or more solvent-exposed polar amino acid residues, 14 or more solvent-exposed polar amino acid residues, 15 or more solvent-exposed polar amino acid residues, 20 or more solvent-exposed polar amino acid residues, or 25 or more solvent-exposed polar amino acids.

Any method known in the art for determining the distance between amino acid residues may be used to determine the distance between a solvent-exposed polar amino acid residue and a highly hydrophobic amino acid residue in a cluster of highly hydrophobic amino acid residues. For example, the distance may be determined to be the least distance between any two atoms of the two residues. Accordingly, in certain embodiments the defined distance between a solvent-exposed polar amino acid residue and a highly hydrophobic amino acid residue in a selected cluster of highly hydrophobic amino acid residues ranges from about 1 Å to about 20 Å. In other embodiments, the defined distance between a solvent-exposed polar amino acid residue and a highly hydrophobic amino acid residue in a selected cluster of highly hydrophobic amino acid residues is at most 20 Å, at most 19 Å, at most 18 Å, at most 17 Å, at most 16 Å, at most 15 Å, at most 14 Å, at most 13 Å, at most 12 Å, at most 11 Å, at most 10 Å, at most 9 Å, at most 8 Å, at most 7 Å, at most 6 Å, at most 5 Å, at most 4 Å, at most 3 Å, at most 2 Å, or at most 1 Å.

Additionally, a solvent-exposed polar amino acid residue is considered to be within the cluster of highly hydrophobic amino acid residues when the distance between the solvent-exposed polar amino acid residue and any one of the highly hydrophobic amino acid residues in the cluster is at most 10 Å, at most 9 Å, at most 8 Å, at most 7 Å, at most 6 Å, or at most 5 Å. Preferably, a solvent-exposed polar amino acid residue is considered to be within the cluster of highly hydrophobic amino acid residues when the distance between the solvent-exposed polar amino acid residue and any one of the highly hydrophobic amino acid residues in the cluster is at most 5 Å.

Alternatively, smoothing functions may also be used to select one or more polar amino acid residues that are within a defined distance of a cluster of highly hydrophobic amino acid residues.

Evolutionarily Conserved Amino Acid Residues

Other aspects of the present disclosure relate to methods, such as computer-implemented methods, computer-readable storage media containing computer-executable instructions, and systems for predicting hot-spot amino acid residues by utilizing a protein structural model of the present disclosure to identify evolutionarily conserved amino acid residues within the selected one or more clusters of highly hydrophobic amino acid residues and the selected one or more solvent-exposed polar amino acid residues of a protein, or portion thereof, and to remove those amino acid residues that do not meet a criterion for evolutionary conservation from the selected one or more clusters of highly hydrophobic amino acid residues and from the selected one or more solvent-exposed polar amino acid residues.

Any criteria known in the art for determining amino acid residue evolutionary conservation may be used. In one non-limiting example, the criterion for evolutionary conservation is a sequence conservation threshold. Sequence conservation thresholds can be selected using a sequence-conservation algorithm. Any sequence-conservation algorithm known in the art may be used to choose a sequence conservation threshold for identifying evolutionarily conserved amino acid residues within the selected one or more clusters of highly amino acid residues and within the selected one or more solvent-exposed polar amino acid residues. Examples of sequence-conservation algorithms include, without limitation, ConSurf, Jensen-Shannon divergence, BLAST, and AL2CO. Additionally, any of the sequence-conservation algorithms disclosed in Capra and Singh, 2007 may be used (Capra and Singh, Predicting functionally important residues from sequence conservation, *Bioinformatics* 2007, 23(15), 1875-1882).

The ConSurf algorithm estimates the degree of evolutionary conservation of amino acid residues of a protein from among its close sequence homologues (Glaser et al., *Bioinformatics* 2003, 19, 163-164). By utilizing the default parameters of ConSurf, the algorithm generates a conservation score for each amino acid residue of a protein. A lower conservation score indicates a higher degree of evolutionary conservation. Accordingly, in certain preferred embodiments, the ConSurf algorithm is used to identify evolutionarily conserved amino acid residues within the selected one or more clusters of highly amino acid residues and within the selected one or more solvent-exposed polar amino acid residues.

As disclosed herein, a cutoff value or score can be used as a criterion for distinguishing between amino acid residues having evolutionary conservation and amino acid residues that do not have evolutionary conservation.

For example, in embodiments where the ConSurf algorithm is used, a score of 0.3, 0.4, 0.5, 0.6, 0.7, 0.8, or 0.9 may be used to distinguish between amino acid residues having evolutionary conservation and those that do not have evolutionary conservation. Accordingly, in certain embodiments, amino acid residues having a ConSurf score that is greater than 0.3, greater than 0.4, greater than 0.5, greater than 0.6, greater than 0.7, greater than 0.8, or greater than 0.9 do not meet the criterion for evolutionary conservation, and are thus removed from the selected one or more cluster of highly hydrophobic amino acid residues and from the selected one or more solvent-exposed polar amino acid residues.

Predicted Hot-Spot Amino Acid Residues

Other aspects of the present disclosure relate to methods, such as computer-implemented methods, computer-readable storage media containing computer-executable instructions, and systems for predicting hot-spot amino acid residues by utilizing a protein structural model of the present disclosure, selecting one or more clusters of highly hydrophobic amino acid residues, selecting one or more solve solvent-exposed polar amino acid residues that are within a defined distance of the cluster, removing those amino acid residues that do not meet a criterion for evolutionary conservation from the selected one or more clusters and from the selected one or more solve solvent-exposed polar amino acid residues to produce a set of one or more predicted hot-spot amino acid residues, and storing the one or more predicted hot-spot amino acid residues.

Accordingly, certain embodiments of the present disclosure provide methods, such as computer-implemented methods, computer-readable storage media containing computer-executable instructions, and systems for predicting hot-spot amino acid residues of a protein. In certain embodiments, the methods, computer-executable instructions, and systems containing a processor configured to execute the computer-executable instructions include the steps of: (a) selecting from the plurality of amino acid residues of the model, a cluster of highly hydrophobic amino acid residues, where the cluster contains two or more amino acid residues each having an effective-hydrophobicity greater than a chosen threshold, and where each amino acid residue in the cluster is within a first defined distance of at least one other amino acid residue in the cluster; (b) selecting from the plurality of amino acid residues of the model, one or more solvent-exposed polar amino acid residues within a second defined distance of at least one amino acid residue in the cluster of highly hydrophobic amino acid residues; (c) removing from the cluster of highly hydrophobic amino acid residues and from the one or more solvent-exposed polar amino acid residues those amino acid residues that do not meet a criterion for evolutionary conservation, to produce a set of one or more predicted hot-spot amino acid residues; and (d) storing the one or more predicted hot-spot amino acid residues.

In additional embodiments, the method and/or instructions may further include predicting additional hot-spot amino acid residues of the protein, or portion thereof, by repeating steps (a)-(d) for at least two, at least three, at least four, at least five, or more additional clusters of highly hydrophobic amino acid residues of the protein, or portion thereof. Alternatively, the method and/or instructions may further include predicting additional hot-spot amino acid residues of the protein, or portion thereof, for all clusters of highly hydrophobic amino acid residues of the protein, or portion thereof, by performing steps (a)-(d) for each of the clusters, where each step is conducted in parallel for each cluster or each series of steps (a)-(b) is performed serially for each cluster.

The stored one or more predicted hot-spot amino acid residues may be presented to a user. The stored one or more predicted hot-spot amino acid residues may be presented by various types of displays, including without limitation, a coordinate map display (e.g., coordinates for locating each of the one or more predicted hot-spot amino acid residues on the protein), a graphical display, a two-dimensional (2D) display, a three-dimensional (3D) display, and a holographic display. The one or more predicted hot-spot amino acid residues may also be presented as a list of predicted hot-spot amino acid residues, or as a contour map visual display of the protein, or portion thereof, indicating the location of the predicted hot-spot amino acid residues. In certain embodiments, the one or more predicted hot-spot amino acid residues may be mapped onto a structural model of the protein. In other embodiments, the one or more predicted hot-spot amino acid residues may be presented as a contour map display of the predicted hot-spot residues. The contour map may be any type of protein contour map known in the art. Examples of suitable contour maps include, without limitation, electron density maps, surface maps, van der Waals maps, and MSMS surface maps.

In certain preferred embodiments, the contour map is a map of a structural binding pocket of the protein, or portion thereof.

The one or more predicted hot-spot amino acid residues may be further utilized to identify amino acid residues involved in macromolecule binding to a protein, to identify a binding-region amino acid residues on the surface of a protein, or to identify hot-spot amino acid residues on the surface of a protein involved in macromolecule binding to the protein.

Accordingly, certain embodiments of the present disclosure provide methods, such as computer-implemented methods, computer-readable storage media containing computer-executable instructions, and systems containing a processor configured to execute the computer-executable instructions to identify amino acid residues involved in macromolecule binding to a protein, by: (a) selecting an effective-hydrophobicity threshold; (b) mapping onto a structural model representing the protein and containing a plurality of amino acid residues, the hot-spot amino acid residues of the protein predicted using any method and/or instructions for predicting hot-spot amino acid residues of the present disclosure to identify hot-spot amino acid residues involved in macromolecule binding to the protein; and (c) outputting the hot-spot amino acid residues involved in macromolecule binding to the protein. Examples of macromolecules that bind to proteins include, without limitation, proteins, antigens, epitopes, ligands, peptides, carbohydrates, chemicals, small molecules, and inhibitors.

Other embodiments of the present disclosure provide methods, such as computer-implemented methods, computer-readable storage media containing computer-executable instructions, and systems containing a processor configured to execute the computer-executable instructions to identify a binding-region amino acid residues on the surface of a protein, by: (a) selecting an effective-hydrophobicity threshold; and (b) mapping onto a structural model representing the protein and containing a plurality of amino acid residues, the hot-spot amino acid residues of the protein predicted using any method and/or instructions for predicting hot-spot amino acid residues of the present disclosure to identify binding-region amino acid residues on the surface of the protein; and (c) outputting the identified binding-region amino acid residues on the surface of the protein.

Other embodiments of the present disclosure provide methods, such as computer-implemented methods, computer-readable storage media containing computer-executable instructions, and systems containing a processor configured to execute the computer-executable instructions to identify hot-spot amino acid residues on the surface of a protein involved in macromolecule binding to the protein, by: (a) selecting an effective-hydrophobicity threshold; and (b) mapping onto a structural model representing the protein and containing a plurality of amino acid residues, the hot-spot amino acid residues of the protein predicted using any method and/or instructions for predicting hot-spot amino acid residues of the present disclosure to identify hot-spot amino acid residues on the surface of the protein; and (c) outputting the identified hot-spot amino acid residues on the surface of the protein.

The effective-hydrophobicity threshold may be varied as described above in the section entitled "Effective-hydrophobicity threshold values." For example, increasing the effective-hydrophobicity threshold increases identification accuracy, while reducing protein coverage.

Applications

The methods, such as computer-implemented methods, computer-readable storage media containing computer-executable instructions, and systems of the present disclosure for predicting hot-spot amino acid residues of a protein, for identifying amino acid residues involved in macromolecule binding to a protein, for identifying a binding-region amino acid residues on the surface of a protein, and for identifying hot-spot amino acid residues on the surface of a protein involved in macromolecule binding to the protein find several uses.

Macromolecular Binding

For example, the methods, such as computer-implemented methods, computer-readable storage media containing computer-executable instructions, and systems of the present disclosure may be used to identify hot spot amino acid residues on a protein involved in binding small molecule inhibitors. In particular, the methods, such as computer-implemented methods, computer-readable storage media containing computer-executable instructions, and systems may be used to identify protein binding sites and/or binding pockets that bind small molecule inhibitors. In certain preferred embodiments, the methods, such as computer-implemented methods, computer-readable storage media containing computer-executable instructions, and systems of the present disclosure may be used to identify small molecule binding sites or binding pockets that inhibit protein-protein interactions (e.g., protein-protein complexes). The methods, such as computer-implemented methods, computer-readable storage media containing computer-executable instructions, and systems of the present disclosure may also be used to identify hot spot amino acid residues on an immunoglobulin or antibody involved in epitope binding. In particular, the methods, such as computer-implemented methods, computer-readable storage media containing computer-executable instructions, and systems may be used to identify epitope binding sites or binding pockets.

Additionally, the methods, such as computer-implemented methods, computer-readable storage media containing computer-executable instructions, and systems of the present disclosure may be used to identify one or more hot spot amino acid residues on a protein that can be modified (e.g., mutated) to modulate macromolecule binding to the protein. The macromolecule that binds to the protein can be, without limitation, a protein binding partner, an antigen, an epitope, a peptide, a ligand, a receptor, a carbohydrate, a chemical, a small molecule, or an inhibitor. In certain embodiments, the one or more modified hot spot amino acid residues may result in increased protein binding to the macromolecule. Alternatively, the one or more modified hot spot amino acid residues may result in decreased protein binding to the macromolecule. In some embodiments, the modified protein having increased binding to the macromolecule can be used to inhibit the macromolecule from binding the wild-type protein.

Accordingly, certain aspects of the present disclosure relate to methods for modulating binding of a protein to a macromolecule including, without limitation, increasing binding, reducing binding, and changing the conditions under which the protein binds to a macromolecule. In certain embodiments, methods for modulating binding of a protein to a macromolecule include: (a) using any of the methods of the present disclosure for predicting hot-spot amino acid residues of a protein, or portion thereof, to identify one or more hot-spot amino acid residues on the protein involved in macromolecular binding that can be modified to modulate binding of the protein to the macromolecule; and (b) modifying the identified one or more hot-spot amino acid residues on the protein to modulate binding of the protein to the macromolecule, as compared to a corresponding protein lacking the modified one or more hot-spot amino acid residues. Methods for modifying amino acid residues, such as mutating amino acid residues, are well known in the art.

The macromolecular binding ability of the modified protein can then be tested in vitro, and compared to the macromolecular binding ability of a corresponding unmodified protein. Additionally, the modified protein can also be tested in vitro to determine whether the modification has changed the macromolecular binding ability of the modified protein, as compared to that of a corresponding unmodified protein.

Other aspects of the present disclosure relate to modified proteins having modulated binding to a macromolecule compared to a corresponding non-modified protein, where the protein was produced by modifying one or more hot-spot amino acid residues on the protein involved in macromolecular binding, where the one or more hot-spot amino acid residues were identified using any of the methods of the present disclosure for predicting hot-spot amino acid residues of a protein, or portion thereof.

Bifunctional Binding

The methods, such as computer-implemented methods, computer-readable storage media containing computer-executable instructions, and systems of the present disclosure may also be used to identify one or more hot spot amino acid residues on a bifunctional protein that can be modified (e.g., mutated) to reduce or inhibit one of the functions of the bifunctional protein. For example, in the case of bifunctional receptors that bind two different ligands, the methods, such as computer-implemented methods, computer-readable storage media containing computer-executable instructions, and systems of the present disclosure can be used to identify one or more hot spot amino acid residues on the bifunctional receptor that can be modified so as to allow preferential binding to one of the two ligands. Preferably, the modification eliminates binding to one of the two ligands.

Accordingly, certain aspects of the present disclosure relate to methods for altering at least one function of a protein having at least two functions associated with separate macromolecular binding sites on the protein, by: (a) using any of the methods of the present disclosure for predicting hot-spot amino acid residues of a protein, or portion thereof, to identify one or more hot-spot amino acid residues on the protein that can be modified to modulate at least one function of the protein; (b) assigning the one or more hot-spot amino acid residues to the respective macromolecular binding site; and (c) modifying the identified one or more hot-spot amino acid residues assigned to the macromolecular binding site associated with the at least one function to alter the at least one function as compared to the at least one function in a corresponding bifunctional protein lacking the modified one or more hot-spot amino acid residues. Methods for modifying amino acid residues, such as mutating amino acid residues, are well known in the art. Other aspects of the present disclosure relate to modified proteins having at least two functions associated with separate macromolecular binding sites on the protein and having at least one of the at least two functions altered as compared to a corresponding non-modified bifunctional protein, where the protein was produced by modifying one or more hot-spot amino acid residues on the protein identified using any of the methods of the present disclosure for predicting hot-spot amino acid residues of a protein, or portion thereof, and assigned to the macromolecular binding site associated with the at least one function that was to be altered.

Yet other aspects of the present disclosure relate to methods for reducing binding of a first ligand to a receptor protein having at least two ligand binding sites, by: (a) using any of the methods of the present disclosure for predicting hot-spot amino acid residues of a protein, or portion thereof, to identify one or more hot-spot amino acid residues on the receptor protein; (b) assigning the one or more hot-spot amino acid residues to the respective ligand binding site; and (c) modifying the identified one or more hot-spot amino acid residues assigned to the first ligand binding site to reduce binding of the first ligand to the modified receptor protein as compared to the binding of the first ligand to a corresponding unmodified receptor protein. Further aspects of the present disclosure relate to modified receptor proteins having at least two ligand binding sites and having reduced binding of a first ligand compared to a corresponding non-modified receptor protein, where the bifunctional receptor protein was produced by modifying one or more hot-spot amino acid residues on the receptor protein identified using any of the methods of the present disclosure for predicting hot-spot amino acid residues of a protein, or portion thereof, and assigned to the first ligand binding site.

Modulation of Protein Properties

The methods, such as computer-implemented methods, computer-readable storage media containing computer-executable instructions, and systems of the present disclosure may also be modified to identify clusters of amino acid residues having desired properties (e.g., physical properties or chemical properties). For example, the methods, such as computer-implemented methods, computer-readable storage media containing computer-executable instructions, and systems of the present disclosure may be used to identify clusters of amino acid residues that aid in protein crystallization. For example, in the case of antibodies, the methods, such as computer-implemented methods, computer-readable storage media containing computer-executable instructions, and systems of present disclosure may be used to identify one or more residues on the antibody that are likely to be present in the crystal interface. These residues can then be modified (e.g., made more hydrophobic or less hydrophobic) so as to allow for easier antibody crystallization.

Additionally, the methods, such as computer-implemented methods, computer-readable storage media containing computer-executable instructions, and systems of the present disclosure may be used to identify protein regions involved in aggregation. In particular, the methods, such as computer-implemented methods, computer-readable storage media containing computer-executable instructions, and systems of the present disclosure may be used to improve the stability of therapeutic proteins against aggregation by modifying the identified amino acid residues involved in protein aggregation (e.g., WO 2009/155518 and U.S. patent application Ser. No. 13/000,353).

Accordingly, certain aspects of the present disclosure relate to methods for reducing protein aggregation of a protein without affecting binding, by: (a) using any of the methods of the present disclosure for predicting hot-spot amino acid residues of a protein, or portion thereof, to identify the predicted hot-spot amino acid residues in a cluster of highly hydrophobic amino acid residues; and (b) replacing at least one residue in the cluster of highly hydrophobic amino acid residues that is not a predicted hot-spot amino acid residues with a less hydrophobic amino acid residue to reduce protein aggregation of the protein without affecting binding, compared to a corresponding protein lacking the replaced at least one amino acid residue.

Small Molecule Binding

Further uses of the methods, such as computer-implemented methods, computer-readable storage media containing computer-executable instructions, and systems of the present disclosure include determining the pharmaceutical effect of small molecules. For example, the methods, such as computer-implemented methods, computer-readable storage media containing computer-executable instructions, and systems of the present disclosure may be used to identify the hot spot amino acid residues on a target protein involved in binding a given small molecule. The identified hot spot amino acid residues can then be screened to identify families of related small molecules that also bind to the identified hot spot amino acid residues to determine how the family of small molecules elicits its pharmaceutical effect through binding of the target protein.

The methods, such as computer-implemented methods, computer-readable storage media containing computer-executable instructions, and systems of the present disclosure may also be used to improve the binding of a therapeutic molecule to its target protein. For example, in the case of a therapeutic molecule having a known protein target, the methods, such as computer-implemented methods, computer-readable storage media containing computer-executable instructions, and systems of the present disclosure may be used to identify one or more hot spot amino acid residues that can be used to design a second generation therapeutic molecule with improved binding to the protein target. Suitable methods for designing small molecules, such as therapeutic molecules, are compatible with the methods, computer-readable storage media containing computer-executable instructions, and systems of the present disclosure. Any method of designing molecules known in the art that is compatible with the methods, computer-readable storage media containing computer-executable instructions, and systems of the present disclosure may be used. A non-limiting example of a suitable method for designing therapeutic molecules includes utilizing a molecular docking algorithm to determine predicting binding strength of therapeutic molecule to protein target. Examples of molecular docking algorithms include, without limitation, AutoDock, eHiTs, FlexX, FRED, GLIDE, LibDock, MOE, CombiBUILD, DockVision, FlexiDock, FlexX, GOLD, HINT!, LIGPLOT, SITUS, VEGA, DOCK, GRAMM, ICM-Dock, 3D-Dock Suite BiGGER, ClusPro, DOT, ESCHER NG, HADDOCK, HEX, ZDOCK, CDOCKER, MCSS, and chemistry module from Molsoft LLC, Monte Carlo docking.

In particular, the methods, such as computer-implemented methods, computer-readable storage media containing computer-executable instructions, and systems of the present disclosure may be used to identify the binding pocket of the therapeutic molecule to its target protein in cases where the structure of the therapeutic molecule (e.g., protein) in unavailable. The therapeutic molecule can then be docked (e.g., using any docking algorithm) to determine the exact mechanism of action of the therapeutic molecule. The docked structure of molecule to the protein can then be used to design second generation therapeutic molecules with improved binding.

Accordingly, certain aspects of the present disclosure relate to methods for producing a therapeutic molecule that inhibits macromolecular binding to a target protein, by: (a) using any of the methods of the present disclosure for predicting hot-spot amino acid residues of a protein, or portion thereof, to identify one or more hot-spot amino acid residues on the target protein involved in macromolecular binding that can be used to design the therapeutic molecule that inhibits macromolecular binding to the target protein; (b) designing the therapeutic molecule to bind to the one or more hot-spot amino acid residues on the target protein; and (c) producing the therapeutic molecule that inhibits macromolecular binding to the target protein. Other aspects of the present disclosure relate to therapeutic molecules that inhibit macromolecular binding to a target protein, where the therapeutic molecule was designed to bind one or more hot-spot amino acid residues on the target protein involved in macromolecular binding identified using any of the methods of the present disclosure for predicting hot-spot amino acid residues of a protein, or portion thereof.

The methods, such as computer-implemented methods, computer-readable storage media containing computer-executable instructions, and systems of the present disclosure may also be used to screen proteomes to identify protein-protein interaction sites. In certain embodiments in silco protein structures based on genomic data can be used.

Accordingly, certain aspects of the present disclosure relate to methods for screening one or more small molecules for binding to a target protein, by: (a) using any of the methods of the present disclosure for predicting hot-spot amino acid residues of a protein, or portion thereof, to identify one or more hot-spot amino acid residues on the target protein involved in binding a first small molecule; and (b) screening a plurality of small molecules related to the first small molecule for binding to the one or more hot-spot amino acid residues on the target protein to identify one or more small molecules that bind the target protein. The screening step may be performed in vitro. Alternatively, the screening step may be performed in silico. In vitro and in silico methods of screening small molecules are well known in the art.

Other aspects of the present disclosure relate to small molecules that bind a target protein, where the small molecules were identified according to the screening methods of the present disclosure.

Hot Spot Amino Acid Residues

Hot spot amino acid residues identified by the methods, such as computer-implemented methods, computer-readable storage media containing computer-executable instructions, and systems of the present disclosure also find various uses. For example, hot spot amino acid residues identified by the methods, such as computer-implemented methods, computer-readable storage media containing computer-executable instructions, and systems of the present disclosure may be used to synthesize artificial binding sites in affinity columns to improve protein isolation and purification; to synthesize binding sites on probes, as well as to produce synthetic surfaces, such as microchips, that serve as protein interaction sites; and to synthesize beads for capturing proteins; to generate synthetic peptides. Hot spot amino acid residues identified by the methods, such as computer-implemented methods, computer-readable storage media containing computer-executable instructions, and systems of the present disclosure may also be used for in silico epitope mapping, in silico mapping of the surface of target macromolecules; or for synthesizing biologics that mimic protein-protein interaction sites. For example, hot spot residues identified on a protein can be mimicked on a stable scaffold protein to yield novel biologics. These novel biologics display the hot spot residues in a configuration that is identical to the original protein.

Accordingly, certain aspects of the present disclosure relate to methods for improving purification of a target protein from an affinity column, by: (a) using any of the methods of the present disclosure for predicting hot-spot amino acid residues of a protein, or portion thereof, to identify one or more hot-spot amino acid residues on the target protein involved in protein binding that can be used to synthesize one or more artificial binding sites specific for the target protein in an affinity column; (b) synthesizing the one or more artificial binding sites specific for the target protein in an affinity column; and (c) using the affinity column having the one or more artificial binding sites to purify the target protein, where the affinity column displays improved protein purification for the target protein, compared to protein purification of the target protein using a corresponding affinity column lacking the one or more artificial binding sites.

Other aspects of the present disclosure relate to methods for producing a binding partner that specifically interacts with a target protein, by: (a) using any of the methods of the present disclosure for predicting hot-spot amino acid residues of a protein, or portion thereof, to identify one or more hot-spot amino acid residues on the target protein involved in protein binding that can be used to design the binding partner that specifically interacts with the target protein; (b) designing the binding partner to bind to the one more hot-spot amino acid residues on the target protein; and (c) producing the binding partner that specifically interacts with the target protein. In certain embodiments, the binding partner is a probe, synthetic surface, bead, synthetic peptide, or biologic. Still other aspects of the present disclosure relate to binding partners that specifically interacts with a target protein produced by the method for producing a binding partner that specifically interacts with a target protein of any of the preceding embodiments, where the binding partner is a probe, synthetic surface, bead, synthetic peptide, or biologic.

Further aspects of the present disclosure relate to methods for producing an epitope that binds a target protein, by: (a) using any of the methods of the present disclosure for predicting hot-spot amino acid residues of a protein, or portion thereof, to identify one or more hot-spot amino acid residues on the target protein involved in protein binding that can be used to identify the epitope that binds the target protein; (b) identifying the epitope that binds to the one or more hot-spot amino acid residues on the target protein; and (b) producing the epitope that binds the target protein. Other aspects of the present disclosure relate to epitopes produced by the preceding method for producing an epitope that binds a target protein.

Computer Implementation

The various aspects and embodiments of the present disclosure are particularly amenable to implementation in computer applications and therefore the present disclosure includes all such aspects and embodiments in the form of computer systems and computer-readable media that has computer-executable instructions for performing any of the methods of the present disclosure including, without limitation, predicting hot-spot amino acid residues of a protein, identifying amino acid residues involved in macromolecule binding to a protein, identifying a binding-region amino acid residues on the surface of a protein, and identifying hot-spot amino acid residues on the surface of a protein involved in macromolecule binding to the protein. Examples of suitable computer systems include, without limitation, a general purpose computer, a supercomputer, a cluster computer, and a single workstation or server.

FIG. 2 depicts an exemplary computer system 200 configured to perform any one of the methods of the present disclosure. The computer system 200 may be a general-purpose computer that includes, without limitation, at least one processor, memory, storage, one or more input/output (I/O) devices (e.g., keyboard, mouse, monitor, disk drive, Internet connection, etc.), and a bus connecting the components to one another. The computer system 200 may also include circuitry or other specialized hardware for carrying out some or all aspects of the methods of the present disclosure. In certain operational settings, computer system 200 can be configured as a system that includes one or more units, each of which is configured to carry out some aspects of the methods in software, hardware, or a combination thereof. In some embodiments, the method for predicting hot spot amino acid residues of a protein described in FIG. 1 may be computed on a computer processor or performed on a computer system.

The computer system 200 shown in FIG. 2 includes multiple standard components that can be used to perform the methods of the present disclosure. Such components include one or more central processing units ("CPU") 202, memory 204, one or more non-transitory computer-readable media drive units (CRM) 206, one or more I/O devices 208, a display 210, and a keyboard 212 connected to a bus 214. Moreover, the one more CPU 202 may include, without limitation, a graphics processing unit ("GPU"). The memory 204 may include, without limitation, Random Access Memory (RAM). The one or more non-transitory CRM units 206 can include, without limitation, one or more media drive units, one or more hard disk drives, one or more floppy disk drives, one or more optical disk drives (e.g., Ds, DVDs, HD-DVDs, Blu-Ray discs, etc.), one or more flash drives, and specially configured hardware devices such as application-specific integrated circuits (ASICs) or programmable logic devices (PLDs). The CRM units 206 can read a computer-readable medium, which typically contains programs and data. The one or more I/O devices 208 may include, without limitation, a mouse, a track ball, a track pad, a touch display, an Internet connection, a printer, and a disk storage unit.

The methods, such as computer-implemented methods, computer-readable storage media containing computer-executable instructions, and systems of the present disclosure may be used to store and/or display a list of one or more predicted hot spot amino acid residues of a protein or to generate a digital image of predicted hot spot amino acid residues of a protein in three-dimensional space. The list or image may be stored in memory 204, a CRM unit 206, an I/O device 208, or viewed on a display 210. The display can include, without limitation, a computer screen display, a touch screen display, a monitor display, a television display, an LED display, and LCD display, a multi-touch display, a projector, and a holographic display.

In some embodiments, the present disclosure relates to computer code for predicting hot spot amino acid residues of a protein according to the methods of the present disclosure. The computer code may be written in a general-purpose programming language, including without limitation Pascal, C, and C++; or in a specialized application-specific language. In other embodiments, the present disclosure provides a web-based, server based, or internet based service for predicting hot-spot amino acid residues of a protein, for identifying amino acid residues involved in macromolecule binding to a protein, for identifying a binding-region amino acid residues on the surface of a protein, and for identifying hot-spot amino acid residues on the surface of a protein involved in macromolecule binding, the service including accepting data about a protein (e.g., a protein structural model) from a user (e.g., over the internet) or retrieving such data from a database such that the service provider can generate, retrieve, or access a static structure of the protein, optionally including molecular dynamics modeling of the protein to provide a dynamic structure of the protein, selecting from the model, a cluster of highly hydrophobic amino acid residues, selecting from the model, one or more solvent-exposed polar amino acid residues within a defined distance of at least one amino acid residue in a selected cluster of highly hydrophobic amino acid residues, removing from the selected cluster and one or more solvent-exposed polar amino acid residues, those amino acid residues that do not meet a criterion for evolutionary conservation, to produce a set of one or more predicted hot-spot amino acid residues, and storing the one or more predicted hot-spot amino acid residues. In some embodiments, the one or more predicted hot-spot amino acid residues are displayed to a user as a structural model mapped with the predicted hot spot amino acid residues by the service provider. In certain embodiments, the user is a person. In other embodiments the user is a computer system or automated computer algorithm.

In some embodiments the present disclosure provides a system for predicting hot spot amino acid residues of a protein, including: a web server for providing a web service for predicting hot spot amino acid residues of a protein to a user terminal through the Internet; a database for storing general information on the prediction method, amino acid effective-hydrophobicity, etc., and a calculation server for performing the hot spot amino acid residue prediction based on information in the database and information provided or transmitted through the internet by the user. In some embodiments, the web server and the calculation server are the same computer system. In some embodiments the computer system is a supercomputer, a cluster computer, or a single workstation or server. In a related embodiment the web server of the hot spot amino acid residue calculation system further includes a controller for controlling the entire operation, a network connection unit for connection to the Internet, and a web service unit for providing a web service for predicting hot spot amino acid residues of a protein to the user terminal connected through the Internet.

In addition, embodiments of the present disclosure further relate to computer storage products with a computer readable medium that contains program code for performing various computer-implemented operations, e.g., predicting hot spot amino acid residues for a structural model, calculating effective-effective hydrophobicity, selecting clusters of highly hydrophobic amino acid residues, selecting solvent-exposed polar amino acid residues within a defined distance of at least one amino acid residue in the selected cluster of highly hydrophobic amino acid residues, identifying the evolutionarily conserved amino acid residues within the selected cluster and selected solvent-exposed polar amino acid residues, removing those amino acid residues that do not meet a criterion for evolutionary conservation, manipulating structural models, implementing molecular dynamics simulations, organizing and storing relevant data, or performing other operations described herein. The computer-readable medium can be any data storage device that can store data which can thereafter be read by a computer system. Examples of computer-readable media include, without limitation, hard disks, floppy disks, flash drives, optical discs (e.g., CDs, DVDs, HD-DVDs, Blu-Ray discs, etc.) and specially configured hardware devices such as application-specific integrated circuits (ASICs) or programmable logic devices (PLDs). The computer-readable medium can also be distributed as a data signal embodied in a carrier wave over a network of coupled computer systems so that the computer-readable code is stored and executed in a distributed fashion. It will be appreciated by those skilled in the art that the above described hardware and software elements are of standard design and construction.

The following Examples are merely illustrative and are not meant to limit any aspects of the present disclosure in any way.

EXAMPLES

Example 1

The following Example relates to a computational tool for predicting protein-protein interaction amino acid residues from the structure of an unbound protein. The computational tool was evaluated by comparing predicted hot spot residues to experimentally determined hot spot residues. The accuracy of the computational tool was also compared against the accuracy of the ISIS[5; 11], meta-PPISP[14] and ConSurf computational tools for predicting hot spot residues.

Materials and Methods

Protein Structure and Molecular Simulation

Protein structures are obtained from the RCSB PDB.[24] Whenever available, structures of proteins not bound to any other protein are used. In few cases, the coordinates of few of the residues in the protein are not located in the x-ray structure. The coordinates of these residues are built using SWISS-MODEL.[25] Hydrogen atoms are added to each protein structure using the PSFGEN plugin of the VMD.[26] Molecular-dynamics simulations are performed for each of these proteins using all-atom models with an explicit model for water. We use the CHARMM22 force field[27] along with the NAMD package[28] for performing these simulations. The simulations are performed at 298 K and 1 atm in the NPT ensemble. Each protein is solvated in an orthorhombic box with periodic boundary conditions in all the directions. A 12 Å water solvation region is used, and an ionic concentration of 150 mM is used. The system is also charge neutralized, and the Ewald summation technique is used to calculate the electrostatic contribution to the system energy. The system is initially minimized and then equilibrated for 5 ns using a time step of 2 fs. A production run of 15 ns is then performed.

Spatial-Interaction-Map (SIM)

The input to the spatial-interaction-map (SIM) tool is a fully-atomistic three-dimensional structure of the protein. sSIM indicates SIM computed on a single protein structure and dSIM indicates SIM computed over multiple structures of the protein. These multiple protein structures are generated using molecular-dynamics simulations. Calculations to perform SIM analysis can be divided in four steps.

Step I: using the structure of the protein, we assign an effective-hydrophobicity value to each of the residue of the protein. The effective hydrophobicity $\Phi_{eff}$ of the $i^{th}$ residue is defined as:[20]

$$\Phi_{eff,i} = \sum_{Simulation\ Average} \left( \frac{SAA\ of\ side\ chain\ atoms\ of\ residue\ i}{SAA\ of\ side\ chain\ atoms\ of\ fully\ exposed\ residue} \right) \times \Phi_i.$$

SAA, solvent-accessible area, of side chain atoms of residue i is computed at each simulation snapshot (for sSIM, the summation is only over one structure); SAA of side-chain atoms of fully-exposed residue (e.g. for amino acid X) is obtained by calculating the SAA of side-chain atoms of the middle residue in the fully extended conformation of the tripeptide Ala-X-Ala and the hydrophobicity of each residue, is obtained from the hydrophobicity scale of Black and Mould.[29] SAA is the area of the surface obtained from rolling a probe sphere on the surface of the protein. A probe sphere radius of 1.4 Å, which is equivalent to that of water molecule, is used. van der Waals radii of each of the atoms of the protein is taken from the CHARMM22 force-field.[27] We normalize the hydrophobicity scale such that glycine has a hydrophobicity of zero. Thus, residues more hydrophobic than glycine (Ala, Cys, Pro, Met, Val, Trp, Tyr, Ile, Leu, Phe) have a positive value while residues less hydrophobic than glycine (Thr, Ser, Lys, Gln, Asn, His, Glu, Asp, Arg) have a negative value of the $\Phi_i$. Furthermore, we normalize the hydrophobicity scale such that the most hydrophobic residue (Phe) has a value of 0.5 while the least hydrophobic residue (Arg) has a value of −0.5.

Step II: the second step of the SIM tool identifies the clusters of highly hydrophobic residues present on the protein surface. We define a cutoff value for the effective hydrophobicity ($\Phi_{cutoff}$); for each $\Phi_{cutoff}$ value we identify all the residues with $\Phi_{eff,i} > \Phi_{cutoff}$ as highly hydrophobic residues. A cluster of highly hydrophobic residues is defined as two or more highly hydrophobic residues present in the vicinity of each other (also see section S1). In our work, the distance between two residues is defined as the least distance between any two atoms of these residues. We use a (Euclidian) distance of 10 Å between two residues as a cutoff for defining the vicinity. The distance of 10 Å (i.e., patch size~320 Å$^2$) corresponds approximately to the lower limit on the size of the protein-protein interface.[30] We then implement reverse Cuthill-McKee algorithm to identify the clusters of highly hydrophobic residues.[31] For computing the dSIM, SAA is averaged over the simulation while the distances between the residues are computed for a representative frame (in our work, we use the last frame from the MD simulation).

Step III: the third step of SIM identifies solvent-exposed charged-residues (Arg, Lys, Asp, Glu) in the vicinity of these hydrophobic clusters. Any solvent-exposed charged-residue within a (Euclidian) distance of 5 Å from any of the highly hydrophobic residue is selected to belong to the cluster as well. A SAA cutoff of 10 Å$^2$ is used to distinguish between solvent-exposed and buried residue.

Step IV: the fourth step of SIM further narrows down the number of predicted residue by discarding all but highly conserved residues. We use a ConSurf score of less than 0.5 as an indicator of high evolutionary conservation (see section S2). Any other sequence-conservation algorithm can as well be used.

Bioinformatics Tools

Exposed: For each of the protein structure (i.e. protein structure with the hydrogen atoms added to each residue), we use the VMD software to compute the solvent-accessible area of the side-chain atoms of each residue. The van der Waal radius of each atom was assigned using the CHARMM22[27] force field and a probe radius of 1.4 Å was used to represent the water molecule. Any residue with a SAA of its side-chain atoms greater than 10 Å$^2$ is identified as an exposed residue.

ConSurf: ConSurf estimates the degree of conservation of the residues of the protein among their close sequence homologues.[15] We use the webserver http://consurf.tau.ac.il/ with the default parameters to generate a conservation score for each residue. A lower score indicates a higher degree of evolutionary conservation. We use a cutoff value of 0.5 to distinguish between conserved residues and non-conserved residues. All exposed residues (i.e. SAA>10 Å$^2$) with ConSurf score<0.5 are considered to be positive predictions.

ISIS: ISIS is a machine-learning based method that identifies residues involved in protein-protein interaction from protein sequence alone.[5; 11] Given the protein sequence, the webserver http://www.predictprotein.org/ generate a score for each residue; higher scores correspond to high chances of being the residue involved in the protein binding. We identified residues with score>20 (the default score) as the predicted residues involved in the protein binding.

Meta-PPISP: meta-PPISP is a meta method that combines three different methods: cons-PPISP, Promate and PINUP.[14] The meta-PPISP webserver http://pipe.scs.fsu.edu/meta-ppisp.html identifies the residues involved in protein binding using the protein structure as an input. We use the default threshold of 0.34 for positive prediction.

Identification of Binding-region and Hot-spot Residues

From the protein-protein complex structure, residues present in the binding region are identified from their loss of solvent accessibility upon binding using the PDBePISA tool (http://pdbe.org/pisa).[32] If the protein of interest binds to multiple partners, we identify all the residues involved in binding to all its partners as binding-region residues. We also identify all the experimentally known hot-spot residues for each of the protein. We adopt the operational definition of hot-spot residue as the residue that upon mutation to alanine leads to at least 10-fold increase in the dissociation constant, $K_D$ of the protein-protein binding (i.e. $\Delta\Delta G > 1.37$ kcal/mol). To discount the allosteric effect of mutation, only the hot-spot residues in the binding region are considered.

Evaluation of Performance

We evaluate the performance of each method for each protein in terms of its accuracy and coverage. The accuracy is calculated as the ratio of the number of the correctly predicted residues to the total number of the predicted residues whereas the coverage is calculated as the ratio of the number of the correctly predicted residues to the number of the experimentally observed residues. The accuracy and coverage is calculated for both: the binding-region residue prediction and the hot-spot residue predictions. Let P be the set of all the residues predicted by a given method for a given protein. Let B be the set of all experimentally known binding-region residues and H be the set of all experimentally known hot-spot residues for a given protein. For each protein, we also generate the set NH of all experimentally known binding-region residues which are experimentally known not be a hot-spot residue. Then the accuracy, ACC and coverage, COV of a method for a protein are given as:

$ACC_B = |P \cap B|/|P|$ $COV_B = |P \cap B|/|B|$ $ACC_H = |P \cap H|/|P|$ $COV_H = |P \cap H|/|H|$ where |•| represents the cardinality of the set, ∩ represents the intersection of the sets, and superscript c denotes the complement of the set. Subscript B and H indicate performance of a method for predicting binding-region and hot-spot residues respectively. In most of the instances, only few of the residues involved in protein binding have been mutated experimentally to identify their contribution to the protein binding. Hence, we also compute the theoretical maximum accuracy, maxACC of each method for the prediction of hot-spot residue as the ratio of the number of predicted residues that lie in the binding region and are not non-hot-spot residue to the total number of residues predicted. Here we have assumed that whenever experimental information is unavailable for a binding-region residue, we count it as a hot-spot residue.

$$\max ACC_H = |P \cap B \cap NH^c|/|P|$$

Results

Identification of Hot-spot Residues Using SIM

The sSIM tool was applied to the protein structure obtained from either x-ray or NMR studies. Whenever the structure of the protein is not available, the SIM tool could also be applied to protein structures obtained from any other method, such as homology modeling. The dSIM tool was also applied to multiple structures of the protein. These multiple structures were generated by performing fully atomistic molecular-dynamics simulations on these proteins. First, SIM computes the effective hydrophobicity $\Phi_{eff}$ of each residue in the protein. The $\Phi_{eff}$ normalizes the hydrophobicity of each residue by its fractional solvent-accessible-area (SAA); thus all buried (including hydrophobic) residues have $\Phi_{eff}$ equal to zero. It then generates a contact-map matrix C of dimensions N×N, where N is the total number of residues in the protein.

Figure 3:
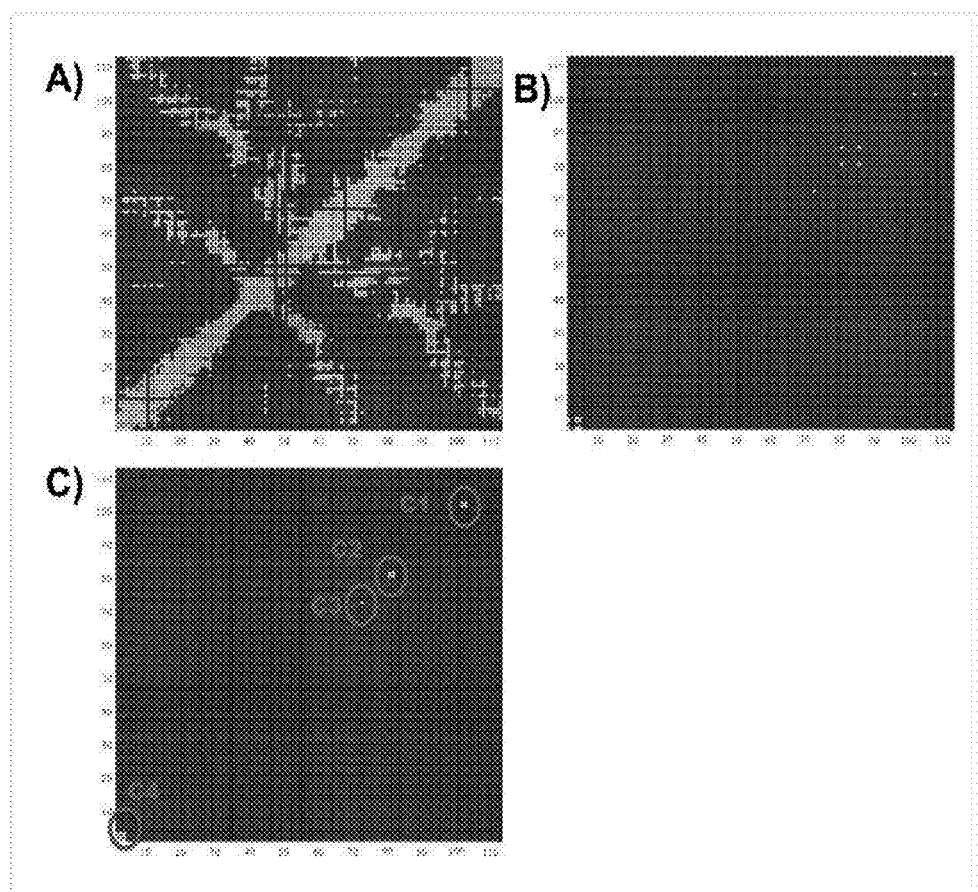
FIG. 3A depicts the contact-map matrix for IL-13 generated using its structure (PDB ID: 1IJZ). The indices represent the residue number. Green indicates 0 while yellow indicates 1.
FIG. 3B depicts the contact-map matrix for IL-13 after the application of high-hydrophobicity filter. A hydrophobicity cutoff of $\Phi_{cutoff}=0.15$ was used.
FIG. 3C shows the contact-map matrix when the highly hydrophobic residues are clustered using the reverse Cuthill-McKee algorithm. Cluster C3 has only one element and hence was discarded. All the residues in cluster C4 are very close to N-terminal and hence C4 was also discarded. The row and column of this matrix do not represent residue number.

FIG. 3A depicts the contact-map matrix for IL-13. An element, $C_{ij}$, of this matrix is one if the residues i and j are within 10 Å of each other, otherwise it is zero. By design, the matrix C is symmetric. SIM then applies a high-hydrophobicity filter to set all the entries of row and column i to zero if the $\Phi_{eff}$ of residue i is less than $\Phi_{cutoff}$. In FIG. 3B, we show the results obtained using $\Phi_{cutoff}$=0.15 to filter out residues with low $\Phi_{eff}$ from the matrix C. The reverse Cuthill-Mckee algorithm (as implemented in MATLAB) is then applied to reorder this sparse matrix so as to identify the clusters of highly hydrophobic residues. FIG. 3C shows that four clusters C1, C2, C3, and C4 of highly hydrophobic residues are present on the surface of IL-13. This procedure selects clusters consisting of exposed hydrophobic residues present in close vicinity of each other. We discarded the clusters (e.g. cluster C3) that had only one highly hydrophobic residue. Furthermore, clusters present very close to the N- and C-termini were also discarded (e.g., cluster C4).

Figure 4:
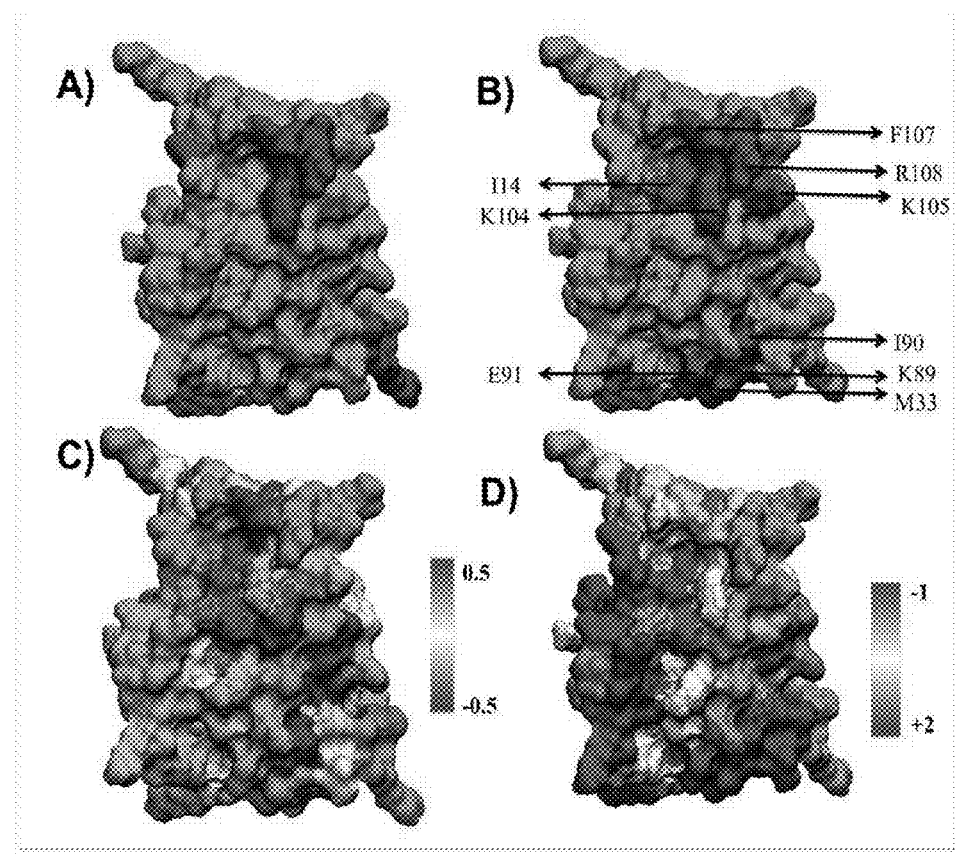
FIG. 4A depicts sSIM map of IL-13 for $\Phi_{eff}=0.15$. Red region indicate residues predicted by sSIM.
FIG. 4B depicts experimental hot spots.
FIG. 4C depicts hydrophobicity scale mapped onto IL-13 structure. Red (value>0) indicates hydrophobic residue.
FIG. 4D depicts ConSurf scores mapped onto IL-13 structure. Red (Value<0.5) indicates conserved residues.

Surface-exposed charged residues in the vicinity of the residues in clusters C1 and C2 were then identified from the protein structure. We further reduced the number of predicted residues by eliminating the residues that were less evolutionarily conserved. FIG. 4A maps these clusters onto the IL-13 surface. Each cluster consisted of exposed conserved charged residues and exposed conserved hydrophobic (i.e. $\Phi_{eff} > \Phi_{cutoff}$) residues. For comparison, we also mapped the hydrophobicity of each residue ($\Phi$) and the ConSurf score of each residue onto the IL-13 surface in FIGS. 4C and 4D, respectively. FIG. 4C shows that the protein studied has many exposed hydrophobic residues and that these regions are distributed over its surface. Thus, it was difficult to pick a certain hydrophobic region that was involved in binding compared to other regions. Similarly, many conserved residues are exposed on the protein surface as seen in FIG. 4D, making the selection of a certain conserved region over other regions difficult.

The number of predicted residues using SIM can be controlled by varying the value of $\Phi_{cutoff}$. At a very large values of $\Phi_{cutoff}$, a small number of residues are predicted, while at moderate values of $\Phi_{cutoff}$, a large number of residues are predicted. For $\Phi_{cutoff}$=0, even the buried (and conserved) residues are predicted. For $\Phi_{cutoff}$=−0.5, all the conserved residues in the protein are predicted. Hence, $\Phi_{cutoff}$ should be set to values greater than 0.1.

Sensitivity of SIM Predictions

Figure 5:
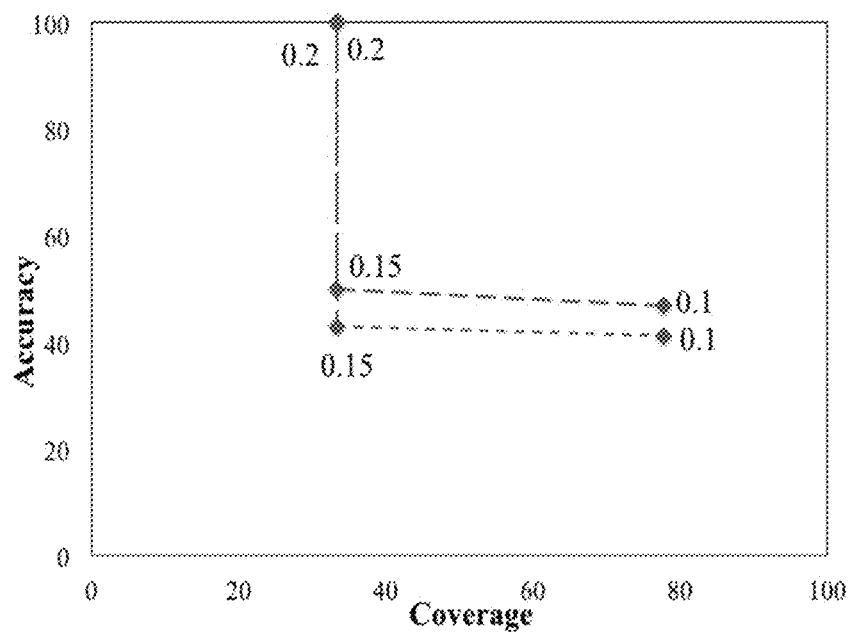
FIG. 5 depicts hot-spot residue predictions for IL-13 using sSIM are shown. Red: predictions when the cluster of highly hydrophobic residues is defined as two or more highly hydrophobic residues present in the vicinity of each other. Blue: predictions when the cluster of highly hydrophobic residues is defined as one or more highly hydrophobic residues present in the vicinity of each other.
Figure 6:
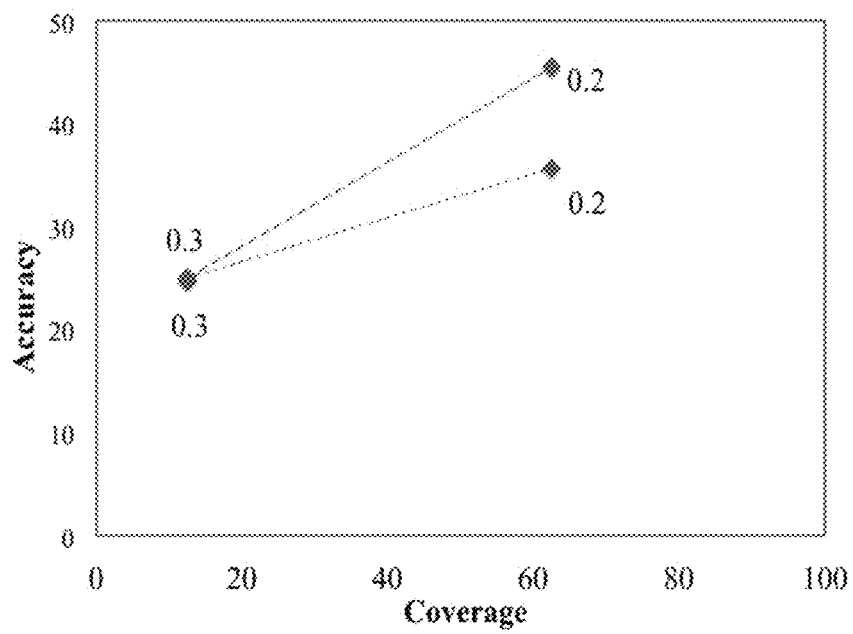
FIG. 6 depicts hot-spot residue predictions for IL-2 using sSIM are shown. Red: predictions when the cluster of highly hydrophobic residues is defined as two or more highly hydrophobic residues present in the vicinity of each other. Blue: predictions when the cluster of highly hydrophobic residues is defined as one or more highly hydrophobic residues present in the vicinity of each other. For clarity, data are shown only for $\Phi_{cutoff}=0.3$ and 0.2.
Figure 7:
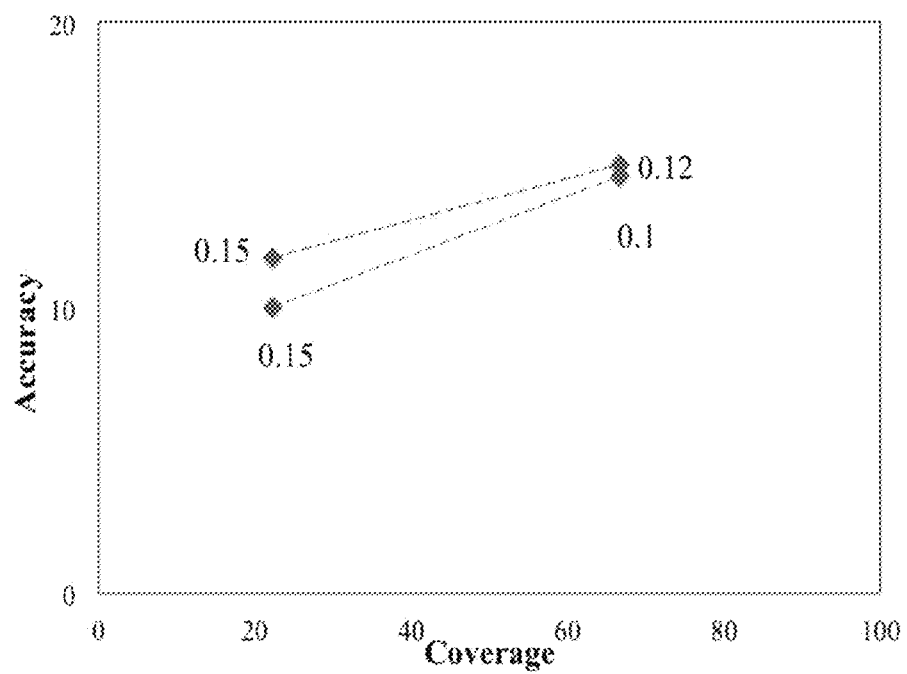
FIG. 7 depicts hot-spot residue predictions for GHR using sSIM are shown. Red: predictions when the cluster of highly hydrophobic residues is defined as two or more highly hydrophobic residues present in the vicinity of each other. Blue: predictions when the cluster of highly hydrophobic residues is defined as one or more highly hydrophobic residues present in the vicinity of each other. For clarity, data are shown only for $\Phi_{cutoff}=0.15$ and 0.1.

For the SIM tool, we identified all clusters of highly hydrophobic residues by applying the reverse Cuthill-Mc-Kee algorithm. We defined a cluster of highly hydrophobic residues as two or more highly hydrophobic residues present in the vicinity of each other. In FIGS. 5-7, we also calculated the accuracy and coverage for the proteins IL-13, IL-2, and GHR when the cluster of highly hydrophobic residues was defined as one or more highly hydrophobic residues present in the vicinity of each other. As seen from these figures, there were no additional advantages to defining a cluster as one or more highly hydrophobic residues present in the vicinity of each other.

Sensitivity Analysis with Respect to ConSurf Score

Figure 8:
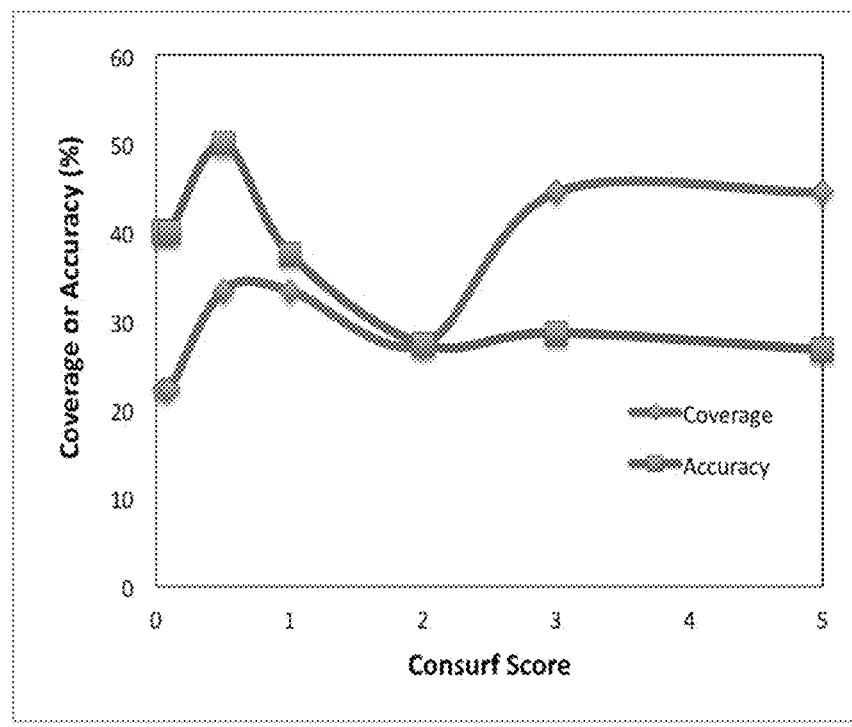
FIG. 8 depicts effect of ConSurf score cutoff on coverage and accuracy for hot-spot residue predictions using sSIM ($\Phi_{cutoff}=0.15$) for IL-13.

For the SIM tool, we used a ConSurf score of 0.5 as a cutoff for defining evolutionarily conserved residue. That is, a ConSurf score of less than 0.5 indicated an evolutionarily conserved residue. In FIG. 8, we show how varying the ConSurf score cutoff affects the coverage and accuracy of sSIM in predicting hot-spot residues. A ConSurf score cutoff of 0.5 resulted in the highest accuracy and coverage (FIG. 8).

Interleukin-13 (IL-13)

Human IL-13 is a ~12 kDa cytokine and is important for the development of the T-helper cell type 2 (Th2) response. Dysregulation of IL-13 mediated response has been linked to asthma and allergic diseases. Structurally, IL-13 belongs to the four helix bundle superfamily. IL-13 mediated heterodimerization of receptors IL-13Rα1 and IL-4Rα initiates the downstream signaling via recruitment and activation of STAT6. IL-13 first binds to IL-13Rα1 (with $K_D$=1.69 nM) followed by the binding of this complex to IL-4Rα receptor. IL-13 can also bind to another receptor IL-13Rα2 with a very high affinity ($K_D$=15.5 fM).[33] Lupardus et al. have characterized the binding energetic of IL-13-IL-13Rα1 and IL-13-IL-13-Rα2 interactions by mutating residues on the surface of IL-13 to alanine.[33] The resulting change in interaction energy upon mutation was measured by isothermal titration calorimetry and surface plasmon resonance. Their experiments identify nine hot-spot residues on IL-13; eight of them are crucial for binding to IL-13Rα1 while three of them are crucial for binding to IL-13Rα2. The residues K104 and F107 are two of the most crucial residues for binding to both the receptors. Indeed mutations K104A or F107A lead to more than a 5000-fold increase in the $K_D$ of IL-13 binding to IL-13Rα2. To identify the binding-region residues of IL-13, we use the available x-ray structures of IL-13 bound to IL-13Rα1 (PDB ID: 3BPO[34]) and IL-13 bound to IL-13Rα2 (PDB ID: 3LB6[33]).

We utilized sSIM, meta-PPISP, and ConSurf to predict IL-13 hot-spot and binding-region residues from the available NMR structure (PDB ID: 1UZ[35]) of unbound IL-13. For ISIS prediction, we used the amino acid sequence of IL-13. We also performed 20 ns MD simulation of IL-13 and applied the dSIM tool to the last 15 ns of the simulation. As we decreased $\Phi_{cutoff}$ from 0.2 to 0.1, we identified more and larger highly hydrophobic clusters by sSIM. A similar trend was observed for dSIM; however no cluster was identified by dSIM when the $\Phi_{cutoff}$ was 0.2.

Figure 9:
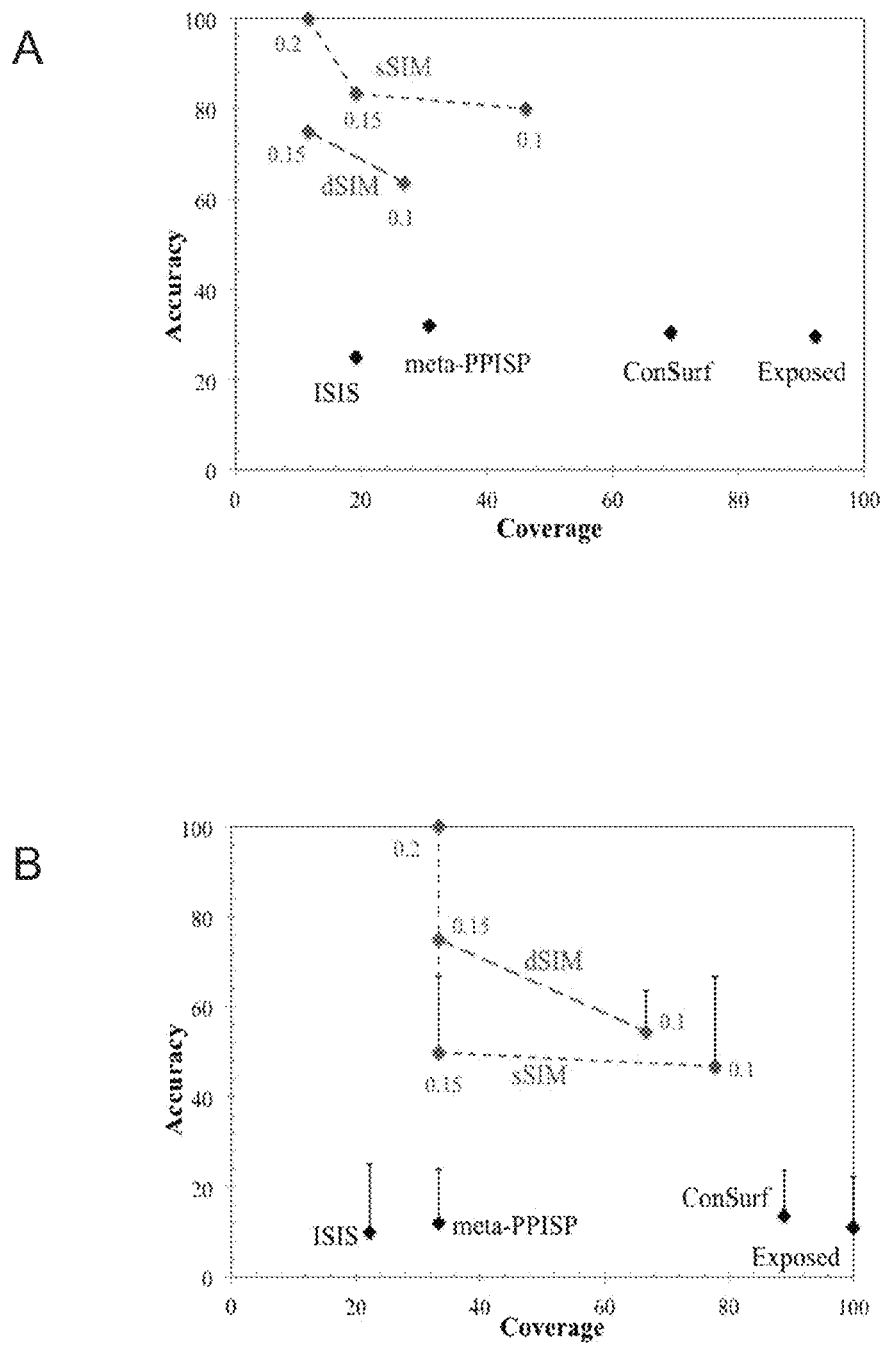
FIG. 9A depicts accuracy and coverage of various methods for predictions of binding-region residues of IL-13. Results for sSIM (green) and dSIM (red) are also shown for various values of $\Phi_{eff}$.
FIG. 9B depicts accuracy and coverage of various methods for predictions of hot-spot residues of IL-13. Results for sSIM (green) and dSIM (red) are also shown for various values of $\Phi_{eff}$. The error bars indicate theoretical maximum accuracy. Since the experimentally known hot spot K105 is not conserved (ConSurf score=2.83), the exposed and the conserved criterion has coverage of less than 100%.

FIG. 9A shows that both meta-PPISP and ISIS fare no better at predicting a binding-region residue than randomly selecting an exposed residue on the surface of IL-13. Likewise, selecting the conserved exposed residues of IL-13 did not have any advantage over random selection of exposed residues. Thus, the structural and sequence-conservation information alone suffers from low accuracy and cannot be used to identify binding-region residues. The SIM tool performed much better in predicting binding-region residues. However, the coverage increased at the cost of accuracy as the value of $\Phi_{cutoff}$ was decreased. The SIM tool, even at a low $\Phi_{cutoff}$, was almost twice as accurate at correctly predicting a residue to be in the binding region as meta-PPISP and ISIS. However, all the prediction methods suffered from low coverage (<50%) for predicting binding-region residues.

Additionally, the SIM tool was able to preferentially predict the hot-spot residues in the binding region (FIG. 9B and Table 2). The SIM tool was able to correctly predict more than ⅓$^{rd}$ of the hot-spot residues with a considerably higher accuracy than meta-PPISP, ISIS, and ConSurf (Table 2). The SIM analysis at a high value of $\Phi_{cutoff}$ correctly predicted the hot-spot residues important for binding to the high-affinity receptor IL-13Rα2, and reducing the value of $\Phi_{cutoff}$ identified hot-spot residues for binding to the low-affinity receptor IL-13Rα1. Importantly, both sSIM and dSIM were able to correctly identify K104 and F105, the two most important hot-spot residues of IL-13. Furthermore, dSIM was able to reduce the number of false positives leading to a better accuracy than sSIM for hot-spot residue predictions. Meta-PPISP and ISIS were also able to identify the hot-spot residues for binding to IL-13Rα1 and IL-13Rα2, albeit with an accuracy that was similar to that of a random selection. Moreover, both these methods failed to predict the K104 and F105 residues. The lack of experimental data on the energetic contribution of all the residues present in the protein-binding interface is highlighted in FIG. 9B by large error bars associated with the accuracy of each method.

Table 2 shows the hot-spot residue predictions for human IL-13 using SIM and a comparison of SIM results with meta-PPISP, ISIS, and ConSurf. Rows with checkmarks indicate the hot-spot residue that a given computational tool predicted.

In Table 2, "Others" corresponds to non-experimentally determined hot-spot residues that were predicted by a given computational tool. In Table 2 values in parenthesis are $K_{D,(Ala)}/K_{D,(WT)}$. K105 is not highly conserved as indicated by a ConSurf score of 2.83. Our ConSurf cutoff score was 0.5. K105 is identified by sSIM(0.2-0.1) and dSIM (0.15-0.1) when we do not include sequence conservation.

Interleukin-2 (IL-2)

Human IL-2 is a ~15 kDa cytokine and belongs to four helix bundle superfamily. It plays an important role in the immune response. The binding of IL-2 to its receptor, IL-2Rα, and followed by sequential recruitment of IL-2Rβ and $γ_c$ leads to the formation of the complex that is able to stimulate signal-transduction pathway. This binding event leads to proliferation of T cell, B cell and natural-killer cells along with clonal expansion.[36] Thanos et al. mutated a few of the residues on the surface of IL-2 to alanine and tested the affinity of each of the variant to IL-2Rα by a competitive ELISA assay.[2] Their experiments identified six hot-spot residues on IL-2 (see section S4). Mutations F42A, Y45A and E62A in IL-2 led to more than 100-fold increase in the $EC_{50}$ value of binding to IL-2Rα compared to the wild-type IL-2. Wang et al. reports that D20 and M88 are critical for IL-2 binding to IL-2Rβ.[37] No hot-spot residues are known for IL-2 binding to its receptor $γ_c$ perhaps because IL-2 alone does not have measurable affinity for $γ_c$.[37] We use the x-ray structure of IL-2 bound to its all three receptors [PDB ID: 2ERJ] to identify the binding-region residues of IL-2.[38]

We applied sSIM, meta-PPISP, and ConSurf to the x-ray structure of the unbound IL-2 (PDB ID: 1M47[39]), while ISIS was applied to the amino acid sequence of IL-2. We also performed 20 ns of MD simulation for IL-2 and applied dSIM to the last 15 ns of the trajectory.

Figure 10:
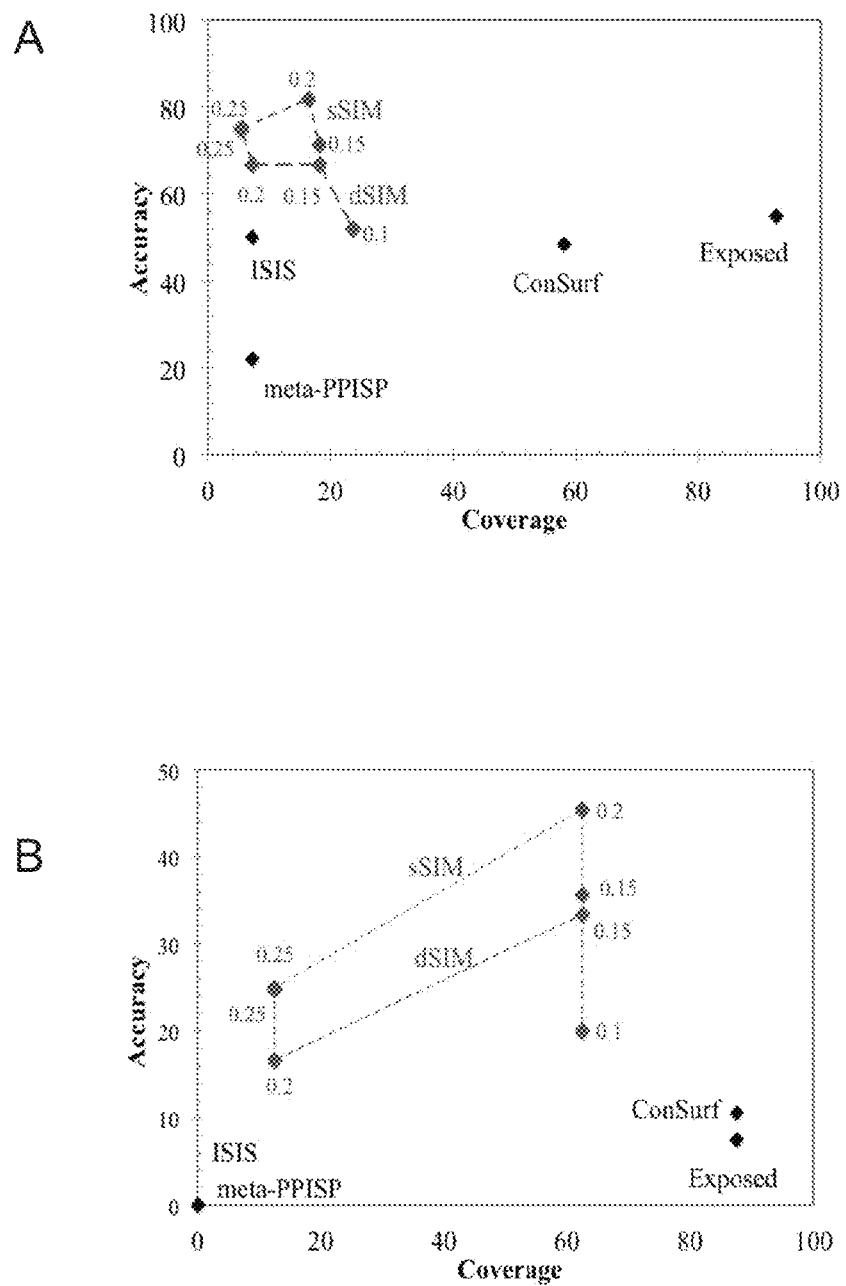
FIG. 10A depicts accuracy and coverage of various methods for prediction of binding-region residues of IL-2. Results for sSIM (green) and dSIM (red) are also shown for various values of $\Phi_{eff}$.
FIG. 10B depicts accuracy and coverage of various methods for predictions of hot-spot residues of IL-2. Results for sSIM (green) and dSIM (red) are also shown for various values of $\Phi_{eff}$. Since the values of theoretical maximum accuracy are very large, instead of being plotted in this figure, the values are given in section S4. Note that y-axis scale is 0-50%.

FIG. 10A and Table 3 show the accuracy and coverage of the different methods for predicting the binding-region residues from the structure of the unbound IL-2 (PDB ID: 1M47[39]). Both sSIM and dSIM performed much better than meta-PPISP and ISIS. Since IL-2 interacts with three receptors simultaneously, almost half of all exposed residues of IL-2 are involved in binding. Surprisingly, meta-PPISP, which is a structure-based method, was less accurate at predicting binding-region residues than randomly selecting an exposed residue from the protein surface. Moreover, the sequence-based ISIS outperformed meta-PPISP (Table 3). As expected, increasing the value of $\Phi_{cutoff}$ lead to more accurate predictions at the cost of reduced coverage.

TABLE 2

| Experiments | | Predictions | | | | | | | |
|---|---|---|---|---|---|---|---|---|---|
| IL-13 + IL-13Rα1[1] | IL-13 + IL-13Rα1[1] | sSIM (0.2) | sSIM (0.15) | sSIM (0.1) | dSIM (0.15) | dSIM (0.1) | meta-PPISP | ISIS | ConSurf |
| I14 (187.6) | I14 | | | | | | | | ✓ |
| M33 (51.2) | | | ✓ | | ✓ | ✓ | | | ✓ |
| K89 (7.6) | | | ✓ | | ✓ | ✓ | | | ✓ |
| I90 (10) | | | ✓ | | | ✓ | | | ✓ |
| E91 (8) | | | ✓ | | | ✓ | | | ✓ |
| K104 (232.5) | K104 (18291) | ✓ | ✓ | ✓ | ✓ | ✓ | | | ✓ |
| | K105 (73.4) | | | | | | | ✓ | |
| F107 (>60) | F107 (5639) | ✓ | ✓ | ✓ | ✓ | ✓ | | | ✓ |
| R108 (124.9) | | ✓ | ✓ | ✓ | ✓ | ✓ | | ✓ | ✓ |
| Others | | +0 | +3 | +8 | +1 | +5 | +22 | +18 | +51 |
| Coverage (%) | | 33.3 | 33.3 | 77.8 | 33.3 | 66.7 | 33.3 | 22.2 | 88.9 |
| Accuracy (%) | | 100 | 50 | 46.7 | 75 | 54.5 | 12 | 10 | 13.6 |
| Max. Acc. (%) | | 100 | 66.7 | 66.7 | 75 | 63.6 | 24 | 25 | 23.7 |

For hot-spot residue predictions, both ISIS and meta-PPISP completely failed to identify any experimentally-defined hot-spot residues (FIG. 10B). The sSIM method achieved a maximum accuracy of around 50%, with a coverage of 60%. When the sSIM $\Phi_{cutoff}$ was set to 0.3 and the dSIM $\Phi_{cutoff}$ was set to 0.25, both methods predicted the D20 residue, which is a hot-spot residue for binding to IL-2Rβ. Reducing the value of $\Phi_{cutoff}$ lead to the prediction of an additional highly hydrophobic cluster containing, among others, the F42, Y45, and E62 hot-spot residues for binding to IL-2Rα. Since SIM can only predict hydrophobic and charged residues, it failed to identify residues T41 and N88. Surprisingly, SIM also failed to identify the hydrophobic residue F44, which is in the vicinity of the cluster identified by SIM. A detailed look at the structure of IL-2 (PDB ID: 1M47) indicated that F44 is barely solvent exposed; the SAA of its side chain atoms was merely 0.37 Å$^2$. We also computed the side-chain SAA of F44 in its bound conformation to IL-2Rα (PDB ID: 2ERJ) to determine whether the binding of IL-2 is accompanied with the exposure of F44. In the bound conformation, the SAA of side chain atoms of F44 was approximately 4 Å$^2$. In light of this low SAA value, it is difficult to ascertain whether the experimentally observed effect of the F44A mutation on binding affinity is due to the critical importance of F44 in binding or due to conformational change of the IL-2 structure upon F44A mutation.

Table 3 shows the hot-spot residue predictions for human IL-2 using SIM and a comparison of SIM results with meta-PPISP, ISIS, and ConSurf. Rows with checkmarks indicate the hot-spot residue that a given computational tool predicted.

W104A and W169A lead to more than 2500-fold increase in the $K_D$ of GHR binding to the growth hormone. The residues of GHR involved in binding to growth hormone (GH) are inferred from the structure of the GHR-GH complex (PDB ID: 1A22[40]).

We utilized sSIM, meta-PPISP, and ConSurf to predict binding-region residues of the extracellular domain of GHR from the available x-ray structure (PDB ID: 1A22). For ISIS prediction, we used the amino acid sequence of GHR. We also performed 20 ns MD simulation of GHR and applied the dSIM tool to the last 15 ns of the simulation.

FIG. 11A and Table 4 show the accuracy and coverage of the different methods for predicting the binding-region residues of GHR. Meta-PPISP was able to predict the binding-region residues with a high accuracy and relatively large coverage. sSIM at $\Phi_{cutoff}$=0.25 also predicted binding-region residues with a comparable accuracy; however sSIM has a much lower coverage. Moreover, meta-PPISP, ISIS, and SIM at $\Phi_{cutoff}$>0.2 performed better in accuracy compared to the selection of all exposed residues. Thus, these methods were able to effectively narrow the search for binding residues by half. Again, with increasing coverage the accuracy of SIM predictions decreased. Since we used a value of 10 Å$^2$ or greater for the SAA of side-chain atoms of the residues to define an exposed residue, a coverage of less than 100% when all exposed residues are included in the predictions indicated that few of the binding-region residues have SAA of their side-chain atoms this is less than 10 Å$^2$.

For hot-spot residue predictions, ISIS completely failed to identify any currently known hot-spot residues (FIG. 11B). However, with increasing experimental data on hot-spot residues, ISIS has the potential to predict GHR hot-spot

TABLE 3

| Experiments | | Predictions | | | | | | | | |
|---|---|---|---|---|---|---|---|---|---|---|
| IL-2 + IL-2Rα² | IL-2 + IL-2Rβ³ | sSIM (0.3) | sSIM (0.2) | sSIM (0.15) | dSIM (0.25) | dSIM (0.15) | dSIM (0.1) | meta-PPISP | ISIS | ConSurf |
| T41 (12) | | | | | | | | | | ✓ |
| F42 (>100) | | | ✓ | ✓ | | ✓ | ✓ | | | ✓ |
| K43 (15) | | | ✓ | ✓ | | ✓ | ✓ | | | ✓ |
| F44 (17) | | | | | | | | | | |
| Y45 (>100) | | | ✓ | ✓ | | ✓ | ✓ | | | ✓ |
| E62 (>100) | | | ✓ | ✓ | | ✓ | ✓ | | | ✓ |
| | D20 | ✓ | ✓ | ✓ | ✓ | ✓ | ✓ | | | ✓ |
| | N88 | | | | | | | | | ✓ |
| Others | | +3 | +6 | +9 | +3 | +10 | +21 | +18 | +8 | +59 |
| Coverage (%) | | 12.5 | 62.5 | 62.5 | 12.5 | 62.5 | 62.5 | 0 | 0 | 87.5 |
| Accuracy (%) | | 25 | 45.5 | 35.7 | 25 | 33.3 | 20 | 0 | 0 | 10.6 |
| Max. Acc. (%) | | 75 | 81.8 | 71.4 | 75 | 66.7 | 52 | 22.2 | 50 | 48.5 |

In Table 3, "Others" corresponds to non-experimentally determined hot-spot residues that were predicted by a given computational tool. In Table 3 values in parenthesis are $EC_{50,(Ala)}/EC_{50,(WT)}$. SAA of side-chain of F44 in the crystal structure (PDB ID: 1M47) is 0.37 Å$^2$, which is less than our cutoff of 10 Å$^2$. In fact, it has been shown that F44A mutation leads to change in IL-2 conformation.[4]

Growth Hormone Receptor (GHR)

Human GHR is a transmembrane receptor with an extracellular domain of more than 28 kDa. Binding of growth hormone (GH) to the first GHR recruits a second GHR to form the active signaling complex. Clackson et al. mutated those GHR residues whose side chains upon binding to growth hormone loose solvent accessibility.[40] They characterized the effect of mutation on binding by radioimmunoassay. Among identified hot-spot residues, mutations residues with an accuracy of up to 50% (Table 4). SIM was able to correctly identify hot-spot residues of GHR with considerably good accuracy and high coverage. Though this trend of increasing accuracy with increasing coverage may be surprising, it should be stressed that this trend was observed primarily because of a huge lack of experimental data on hot-spot residues for this protein. Indeed, this becomes evident when the theoretical maximum accuracy is considered (Table 4). At high value of $\Phi_{cutoff}$, the theoretical maximum accuracy for sSIM is 50% (Table 4). This high value indicates that with additional mutagenesis experiments on the binding-region residues, there is a potential for the accuracy of SIM at $\Phi_{cutoff}$=0.2 to reach 50%. Moreover, as expected, the theoretical maximum accuracy decreases with increasing coverage for both sSIM and dSIM (Table 4). Both sSIM (at $\Phi_{cutoff}$=0.12) and dSIM (at $\Phi_{cutoff}$=0.15) were able to identify residues W104 and W169, the two most crucial hot-spot residues for GHR. However, meta-PPISP and ISIS failed to identify these two hot-spot residues.

Table 4 shows the hot-spot residue predictions for human GHR using SIM and a comparison of SIM results with meta-PPISP, ISIS, and ConSurf. Rows with checkmarks indicate the hot-spot residue that a given computational tool predicted.

In Table 5, "Others" corresponds to non-experimentally determined hot-spot residues that were predicted by a given computational tool. In Table 5, FcRn refers to "neonatal Fc-receptor." Values in parenthesis are the ratio of binding of the Ala-variant to that of native IgG1 at 0.33 or 1 µg/ml. The mutant E233P, L234V, L235A G236Δ has a value of 0.54 for the ratio of binding of the mutant to that of native IgG1.

TABLE 4

| Experiments GHR + GH[5] | Predictions | | | | | | | | | | |
|---|---|---|---|---|---|---|---|---|---|---|---|
| | sSIM (0.2) | sSIM (0.15) | sSIM (0.12) | sSIM (0.1) | dSIM (0.25) | dSIM (0.2) | dSIM (0.15) | dSIM (0.1) | meta-PPISP | ISIS | ConSurf |
| R43 (35.7) | | ✓ | ✓ | ✓ | | | | | | | ✓ |
| E44 (17.4) | | | ✓ | ✓ | | | | | | | ✓ |
| I103 (15.1) | | | | | | | | | | | |
| W104 (>2500) | | ✓ | ✓ | ✓ | | | ✓ | ✓ | | | ✓ |
| I105 (26.5) | | | | | | | | | ✓ | | |
| P106 (265) | | | | | | | | | ✓ | | |
| D164 (12.3) | | | ✓ | ✓ | | | | | | | ✓ |
| I165 (36.5) | | | ✓ | ✓ | | | ✓ | ✓ | | | ✓ |
| W169 (>2500) | | | ✓ | ✓ | | | ✓ | ✓ | | | ✓ |
| Others: | +4 | +15 | +26 | +34 | +3 | +5 | +22 | +33 | +27 | +16 | +88 |
| Coverage (%) | 0 | 22.2 | 66.7 | 66.7 | 0 | 0 | 33.3 | 33.3 | 22.2 | 0 | 66.7 |
| Accuracy (%) | 0 | 11.8 | 18.7 | 15 | 0 | 0 | 12 | 83 | 6.9 | 0 | 6.4 |
| Max. Acc. (%) | 50 | 41.2 | 40.6 | 32.5 | 66.7 | 40 | 32 | 30.6 | 65.5 | 50 | 24.5 |

In Table 4, "Others" corresponds to non-experimentally determined hot-spot residues that were predicted by a given computational tool. In Table 4, GH refers to "growth hormone." Values in parenthesis are $K_{D,(Ala)}/K_{D,(WT)}$. SAA of side-chain of I103 is 7 Å$^2$, which is less than our cutoff of 10 Å$^2$. I105 and P106 are not highly conserved as indicated by their ConSurf score of 0.59 2.43 respectively. Our cutoff for ConSurf score is 0.5. I105 is identified by sSIM (0.1) and dSIM (0.1) when we do not include sequence conservation.

Human Immunoglobulin G1 (IgG1)

We utilized sSIM, meta-PPISP, and ConSurf to predict binding-region residues of IgG1 from the available structure. For ISIS prediction, we used the amino acid sequence of IgG1. We also performed 20 ns MD simulation of IgG1 and applied the dSIM tool to the last 15 ns of the simulation.

Table 5 shows the accuracy and coverage of hot-spot residue predictions for human IgG1 using SIM and a comparison of SIM results with meta-PPISP, ISIS, and ConSurf. Rows with checkmarks indicate the hot-spot residue that a given computational tool predicted.

E233, E234 and Y436 are not highly conserved as indicated by their ConSurf score of 0.81, 1.89 and 2.03 respectively. Our cutoff for ConSurf score is 0.5. E233 and E234 are identified by sSIM (0.3-0.15) and dSIM (0.25-0.15) when we do not include sequence conservation. Y436 is identified by dSIM (0.15) when we do not include sequence conservation.

Human Interleukin-15 (IL-15)

We utilized sSIM, meta-PPISP, and ConSurf to predict binding-region residues of IL-15 from the available structure. For ISIS prediction, we used the amino acid sequence of IL-15. We also performed 20 ns MD simulation of IL-15 and applied the dSIM tool to the last 15 ns of the simulation.

Table 6 shows the accuracy and coverage of hot-spot residue predictions for human IL-15 using SIM and a comparison of SIM results with meta-PPISP, ISIS, and ConSurf. Rows with checkmarks indicate the hot-spot residue that a given computational tool predicted.

TABLE 5

| | Experiments | | Predictions | | | | | | | | | | |
|---|---|---|---|---|---|---|---|---|---|---|---|---|---|
| Fc + FcRn[6] | Fc + FcγRI[6] | sSIM (0.3) | sSIM (0.25) | sSIM (0.2) | sSIM (0.15) | dSIM (0.3) | dSIM (0.25) | dSIM (0.2) | dSIM (0.15) | meta-PPISP | ISIS | ConSurf |
| | E233 | | | | | | | | | | | |
| | L234 | | | | | | | | | | | |
| | L235 | | ✓ | ✓ | ✓ | | ✓ | ✓ | ✓ | | | ✓ |
| I253 (<0.1) | | ✓ | ✓ | ✓ | ✓ | ✓ | ✓ | ✓ | ✓ | | | ✓ |
| S254 (<0.1) | | | | | | | | | | | | ✓ |
| H435 (<0.1) | | | | | | | | | | | | ✓ |
| Y436 (<0.1) | | | | | | | | | | | | |
| Others | | +3 | +9 | +9 | +18 | +3 | +8 | +11 | +17 | +14 | +16 | +89 |
| Coverage (%) | | 14.3 | 28.6 | 28.6 | 28.6 | 14.3 | 28.6 | 28.6 | 28.6 | 0 | 0 | 57.1 |
| Accuracy (%) | | 25 | 18.2 | 18.2 | 10 | 25 | 20 | 15.4 | 10.5 | 0 | 0 | 4.3 |
| Max. Acc. (%) | | 25 | 18.2 | 18.2 | 20 | 25 | 20 | 23.1 | 15.8 | 21.4 | 6.3 | 23.7 |

TABLE 6

| Experiments | Predictions | | | | | |
|---|---|---|---|---|---|---|
| IL-15 + IL-15Rα[7] | sSIM (0.3) | sSIM (0.2) | sSIM (0.15) | meta-PPISP | ISIS | ConSurf |
| D22 (27) | | | | | | ✓ |
| Y26 (85000) | | | | | | ✓ |
| E46 (3800) | ✓ | ✓ | ✓ | | | ✓ |
| L47 (78) | | | | | | |
| E53 (370) | ✓ | ✓ | ✓ | | | ✓ |
| E87 (320) | | | | | | ✓ |
| E90 (3500) | | | | | | ✓ |
| Others | +2 | +2 | +5 | +22 | +4 | +47 |
| Coverage (%) | 28.6 | 28.6 | 28.6 | 0 | 0 | 85.7 |
| Accuracy (%) | 50 | 50 | 28.6 | 0 | 0 | 11.3 |
| Max. Acc. (%) | 75 | 75 | 42.9 | 0 | 0 | 22.6 |

In Table 6, "Others" corresponds to non-experimentally determined hot-spot residues that were predicted by a given computational tool. In Table 6, values in parenthesis are $K_{D,(Ala)}/K_{D,(WT)}$. SAA of side-chain of L47 is 0 Å$^2$, which is less than our cutoff of 10 Å$^2$.

Figure 12:
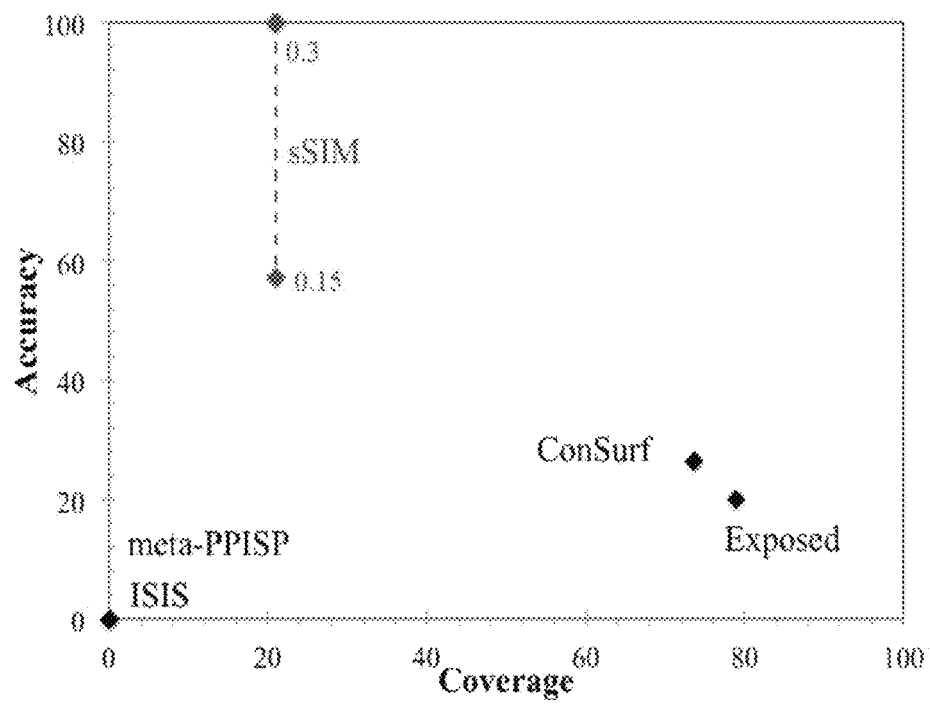
FIG. 12 depicts accuracy and coverage of various methods for prediction of binding-region residues of IL-15. Results for sSIM (green) are also shown for various values of $\Phi_{eff}$. Binding-region residues for IL-15-IL-15Rα complex were identified using the structure PDB ID: 2Z3Q.

FIG. 12 shows the accuracy and coverage of sSIM, dSIM, meta-PPISP, ISIS, and ConSurf for predicting binding-region residues of IL-15.

Human Growth Hormone (GH)

We utilized sSIM, meta-PPISP, and ConSurf to predict binding-region residues of GH from the available structure. For ISIS prediction, we used the amino acid sequence of GH. We also performed 20 ns MD simulation of GH and applied the dSIM tool to the last 15 ns of the simulation.

Table 7 shows the accuracy and coverage of hot-spot residue predictions for human GH using SIM and a comparison of SIM results with meta-PPISP, ISIS, and ConSurf. Rows with checkmarks indicate the hot-spot residue that a given computational tool predicted.

TABLE 7

| Experiments | Predictions | | | | | |
|---|---|---|---|---|---|---|
| GH + GHR[8] | sSIM (0.3) | sSIM (0.2) | sSIM (0.15) | meta-PPISP | ISIS | ConSurf |
| I58 (16.5) | | | | | | ✓ |
| R64 (20.9) | | | | | | ✓ |
| K172 (13.5) | ✓ | ✓ | ✓ | | | ✓ |
| T175 (17.4) | | | | | | |
| F176 (15.9) | ✓ | ✓ | ✓ | | | ✓ |
| Others | +3 | +7 | +13 | +39 | +23 | +91 |
| Coverage (%) | 0 | 0 | 0 | 0 | 0 | 60.0 |
| Accuracy (%) | 0 | 0 | 0 | 0 | 0 | 3.19 |
| Max. Acc. (%) | 25 | 40 | 26.32 | 23.08 | 21.74 | 15.96 |

In Table 7, "Others" corresponds to non-experimentally determined hot-spot residues that were predicted by a given computational tool. In Table 7, GHR refers to "growth hormone receptor." Values in parenthesis are $K_{D,(Ala)}/K_{D,(WT)}$. T175 was mutated to Ser. SAA of side-chains of K172 and F176 are 1.35 and 9 Å$^2$ resp., which is less than our cutoff of 10 Å$^2$. Crystal structure of GH bound to GHR (PDB ID: 3HHR) indicates that I58 of GH is, in fact, not even present in the binding region. Since, I58 is present on a loop, it is highly likely that I58A mutation disrupts the local conformation of the loop resulting in observed decrease in binding. Hence, I58 is important in maintaining the right conformation of the loop; while the energetic contribution of I58 to the binding is negligible. F176A and K172A are highly likely to disrupt the loop (S51-N63) conformation since both F176 and K172 interacts with multiple residues of this loop. Hence, major contribution of reduction in binding to GHR upon mutation in these two residues is more likely to be a result of loop conformational change. Binding-region residues for GH-GHR complex were identified using the structure PDB ID: 3HHR.

Figure 13:
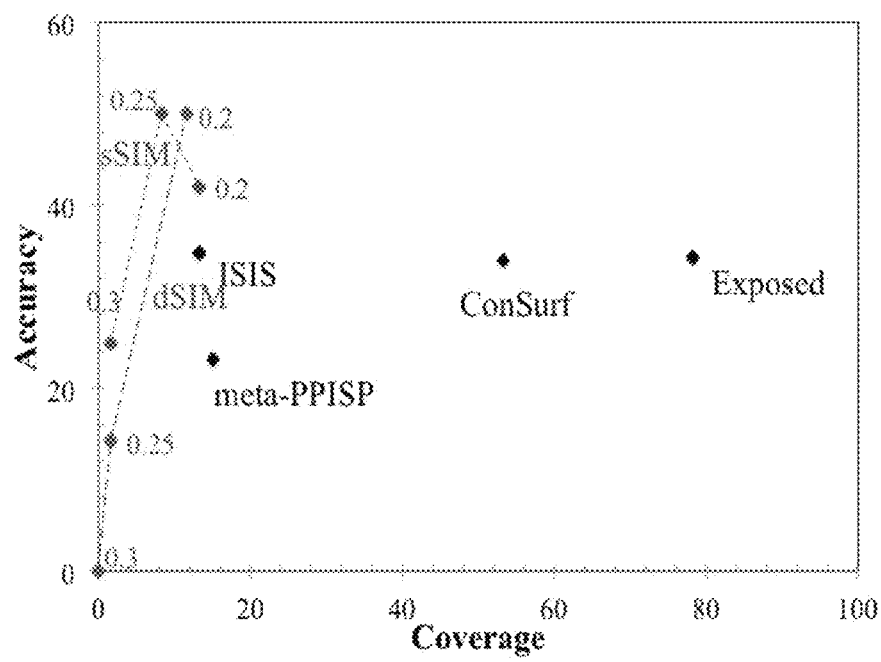
FIG. 13 depicts accuracy and coverage of various methods for prediction of binding-region residues of GH. Results for sSIM (green) and dSIM (red) are also shown for various values of $\Phi_{eff}$. Binding-region residues for GH-GHR complex were identified using the structure PDB ID: 3HHR.

FIG. 13 shows the accuracy and coverage of sSIM, dSIM, meta-PPISP, ISIS, and ConSurf for predicting binding-region residues of GH.

Binding-region Residue Prediction for Additional Human Proteins

We utilized sSIM, meta-PPISP, and ConSurf to predict binding-region residues of human erythropoietin (EPO), human interleukin-13 receptor alpha-1 (IL-13Rα1), and human epidermal growth factor receptor (EGFR) from the available structures of each protein. For ISIS prediction, we used the amino acid sequences of EPO, IL-13Rα1, and EGFR, respectively. We also performed 20 ns MD simulation of each protein and applied the dSIM tool to the last 15 ns of each simulation.

Figure 14:
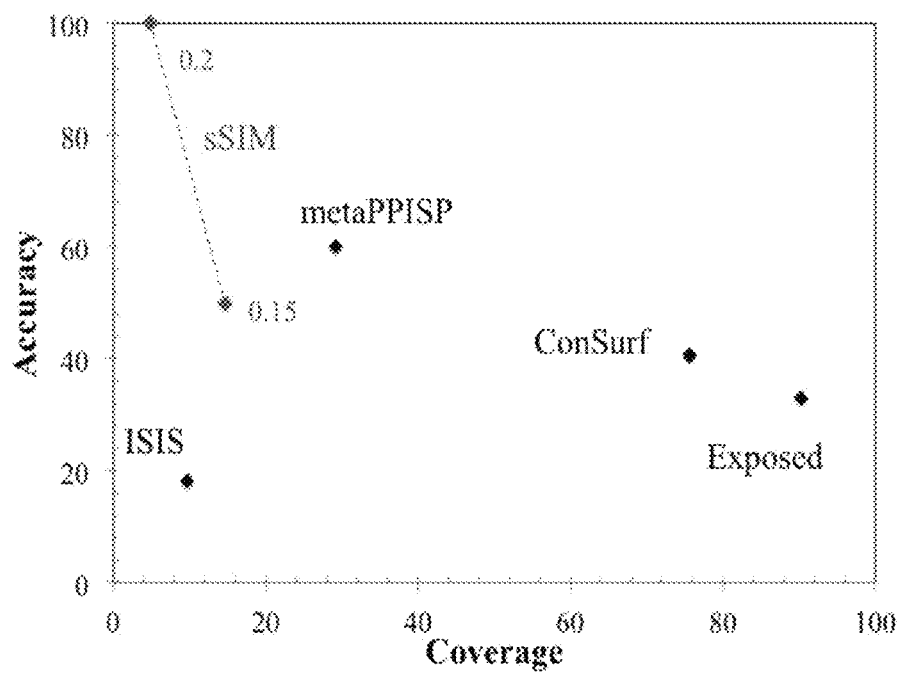
FIG. 14 depicts accuracy and coverage of various methods for prediction of binding-region residues of EPO. Results for sSIM (green) are also shown for various values of $\Phi_{eff}$. Binding-region residues for EPO-EPOR complex were identified using the structure PDB ID: 1EER.

FIG. 14 shows the accuracy and coverage of sSIM, dSIM, meta-PPISP, ISIS, and ConSurf for predicting binding-region residues of EPO.

Figure 15:
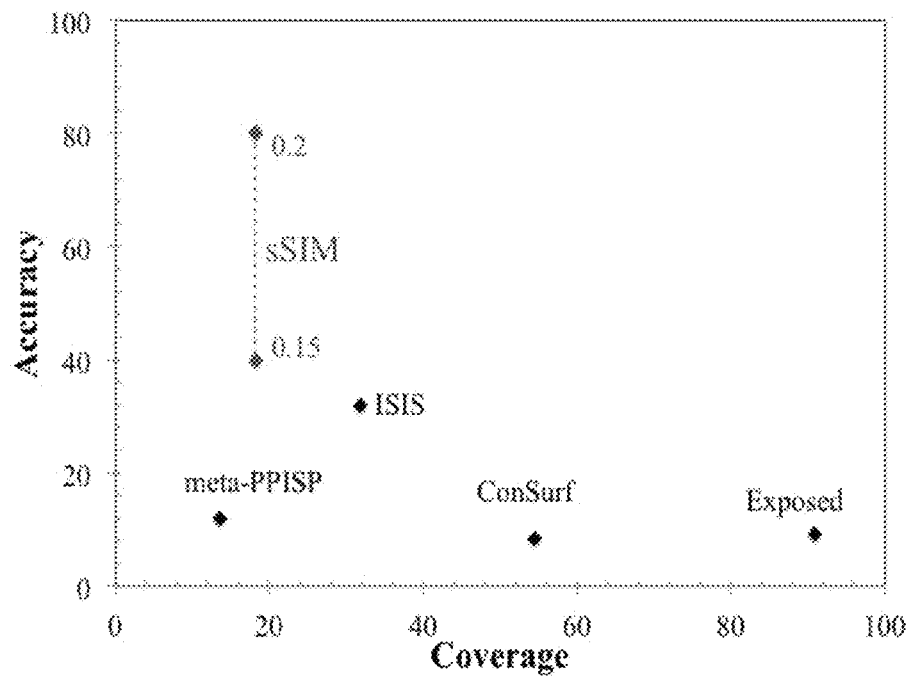
FIG. 15 depicts accuracy and coverage of various methods for prediction of binding-region residues of IL-13Rα1. Results for sSIM (green) are also shown for various values of $\Phi_{eff}$. Binding-region residues for IL-13Rα1-IL-13 complex were identified using the structure PDB ID: 3BPO. Experimental data on determination of hot-spot residues for IL-13Rα1 is not available.

FIG. 15 shows the accuracy and coverage of sSIM, dSIM, meta-PPISP, ISIS, and ConSurf for predicting binding-region residues of IL-13Rα1.

Figure 16:
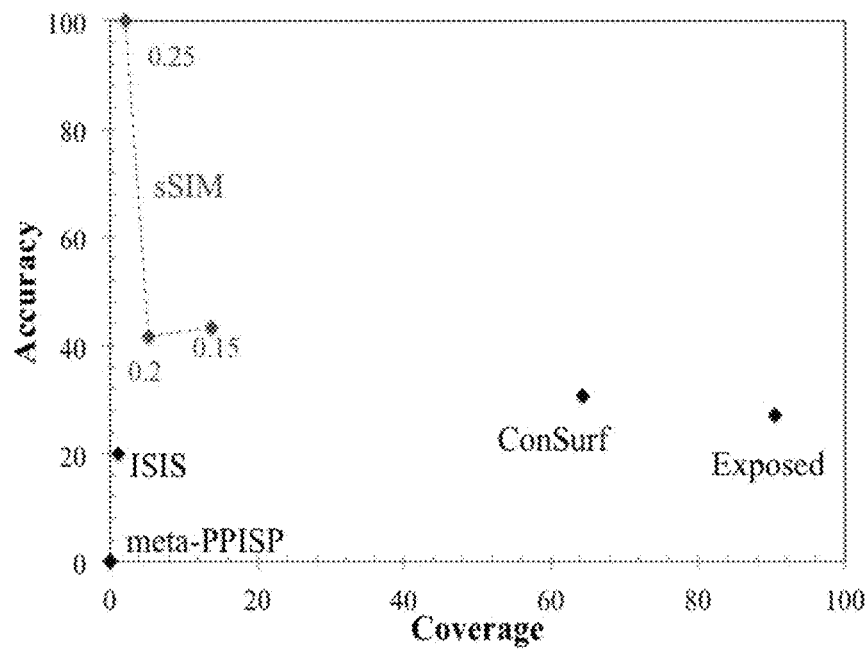
FIG. 16 depicts accuracy and coverage of various methods for prediction of binding-region residues of EGFR.

FIG. 16 shows the accuracy and coverage of sSIM, dSIM, meta-PPISP, ISIS, and ConSurf for predicting binding-region residues of EGFR.

Average Performance of SIM, Meta-PPISP, ISIS, and ConSurf

Tables 8-10 show the average protein-protein interaction residue prediction performance of SIM, meta-PPISP, ISIS, and ConSurf. For SIM, the averages are computed using sSIM at $\Phi_{cutoff}=0.15$ and $\Phi_{cutoff}=0.2$.

Table 8 shows the accuracy of various methods for prediction of hot-spot residues.

TABLE 8

| | sSIM (0.2) | sSIM (0.15) | meta-PPISP | ISIS | ConSurf |
|---|---|---|---|---|---|
| IL-13 | 100 | 50 | 12 | 10 | 13.6 |
| IL-2 | 45.5 | 35.71 | 0 | 0 | 10.6 |
| GHR | 0 | 11.8 | 6.9 | 0 | 6.4 |
| Fc | 18.2 | 10 | 0 | 0 | 4.3 |
| IL-15 | 50 | 28.6 | 0 | 0 | 11.3 |
| GH | 0 | 0 | 0 | 0 | 3.19 |
| Average | 36 | 23 | 3 | 2 | 8 |

Table 9 shows the theoretical maximum accuracy of various methods for prediction of hot-spot residues.

TABLE 9

| | sSIM (0.2) | sSIM (0.15) | meta-PPISP | ISIS | ConSurf |
|---|---|---|---|---|---|
| IL-13 | 100 | 66.7 | 24 | 25 | 23.7 |
| IL-2 | 75 | 71.43 | 22.2 | 50 | 48.5 |
| GHR | 50 | 41.2 | 65.5 | 50 | 24.5 |
| Fc | 18.2 | 20 | 21.4 | 6.3 | 23.7 |
| IL-15 | 75 | 42.9 | 0 | 0 | 22.6 |
| GH | 26.32 | 26.32 | 23 | 21.74 | 15.96 |
| Average | 57 | 45 | 26 | 26 | 26 |

Table 10 shows the accuracy of various methods for prediction of binding-region residues.

TABLE 10

|  | sSIM (0.2) | sSIM (0.15) | meta-PPISP | ISIS | ConSurf |
|---|---|---|---|---|---|
| IL-13 | 100 | 83.33 | 32 | 25 | 30.51 |
| IL-2 | 81.82 | 71.43 | 22.22 | 50 | 48.48 |
| GHR | 50 | 41.18 | 65.52 | 50 | 24.27 |
| Fc | 42.11 | 30 | 50 | 31.25 | 34.41 |
| IL-15 | 100 | 100 | 0 | 0 | 26.42 |
| GH | 42.11 | 42.11 | 23.08 | 34.78 | 34.04 |
| Average | 69 | 61 | 32 | 32 | 33 |

Discussion

A large amount of structural information has been accumulated over the years on proteins and protein-protein complex structures. Whereas protein-protein complex structures yield information on the residues present in the binding interface, additional subsequent experiments or computational studies need to be performed to determine the contribution of each of these residues to the protein-protein binding. Alanine scanning mutagenesis experiments have been the key driver on the experimental front to pin point the role of each of the binding-region residue. On the computational front, application of computational alanine scanning mutagenesis, where the energy functional is parameterized using available experimental alanine-mutagenesis data, on the protein-protein complex structure has shown to be promising in determining the role of these binding-region residues. While, in general, a large number of residues are buried in the protein-protein complex interface, only a fraction of these residues, termed hot-spot residues, are critical to PPI. The presence of these hot-spot residues has been confirmed experimentally by alanine mutagenesis experiments where mutation of only few of the binding-region residues to alanine has abrogated the binding of proteins to a large extent. Though many computational tools are available to determine the protein-protein binding-region residues, there is a general lack of computational tools to identify the hot-spot residues using the sequence/structure of the protein alone.

The above Example demonstrates that the SIM computational tool can be used accurately to predict the hot-spot residues using the structure of the protein alone. Since both hydrophobic and electrostatic interactions contribute greatly to the protein-protein binding energy, the SIM tool is devised to identify clusters of exposed hydrophobic residues along with the exposed charged residues. Moreover, conservation of residues along the evolution is often considered as an indicator of the importance of the residue for either protein structure or protein interaction. Hence, we use sequence conservation as an additional criterion to improve the quality of SIM predictions. The SIM tool can be applied either directly to the static structure of the protein or to the multiple conformations generated via MD simulations. The SIM tool based on molecular simulations takes into account the contribution due to protein flexibility and dynamic exposure of the residues. The performance of SIM tool was compared against bioinformatics tools for six proteins (IL-13, IL-2, GHR, Fc-domain, IL-15 and GH). In general, high accuracy for hot-spot residues can be obtained by using SIM at high value of $\Phi_{cutoff}$ while a high coverage for hot-spot residues can be obtained by using SIM at low value of $\Phi_{cutoff}$. For above-mentioned six proteins, we show that SIM predicts hot-spot residues with an average accuracy of 36-57% for $\Phi_{cutoff}=0.2$ and 23-45% for $\Phi_{cutoff}=0.15$. The hot-spot residue prediction accuracy of the SIM tool is superior compared to bioinformatics tools like meta-PPISP (3-26%), ISIS (2-26%) and ConSurf (8-26%). Moreover, the average accuracy of SIM for prediction of binding-region residues (69% for $\Phi_{cutoff}=0.2$ and 61% for $\Phi_{cutoff}=0.15$) also fares better than the average accuracy of meta-PPISP (32%), ISIS (32%) and ConSurf (33%). Indeed, the SIM tool, which is a zero-fit model and is not trained on a database, outperforms bioinformatics tools, which are generally trained on a large database.

Example 2

The following Example demonstrates that the SIM computational tool is more accurate at predicting hot-spot residues than simple hydrophobic analysis, and the bioinformatics tool PredUs.

Materials and Methods

All materials and methods utilized were as described in Example 1.

The bioinformatics tools Hydrophobic and PredUs are described below.

Simple hydrophobic analysis (Hydrophobic): This analysis is used to identify all the exposed residues on the protein surface. All exposed hydrophobic residues (i.e. TRP, TYR, VAL, MET, PHE, PRO, ILE, LEU, CYS and ALA) are considered as predicted residue using this method.

PredUs: PredUs predicts binding-region residues by mapping contacts from known binding-region interfaces of the query protein's structural neighbors to the surface residues of the query.[44,45] With the static structure of the unbound protein as an input, we use the webserver http://bhapp.c2b2.columbia.edu/PredUs/ with the default parameters to identify binding-region residues. Since we are interested in computational tools that can predict hot-spot residues when the structure of the protein-protein complex is unavailable, we run PredUs in the "Interactive Prediction" mode and exclude all complex structures where the protein of interest is one of the binding partners. Table 11 list the PDB structures excluded for each protein that was evaluated.

TABLE 11

| Protein | Excluded PDB files |
|---|---|
| IL-13 | 3G6D, 3LB6, 3BPO, 3L5W |
| IL-2 | 2B5I, 1M48 |
| GHR | 1AXI, 1A22 |
| Fc | 2VOL, 2GJ7, 1I1A, 1CQK, 3AGV, 2IWG, 1L6X, 1DN2, 1T83, 1IGT |
| IL-15 | 2Z3Q, 2PSM, 2Z3R, 2XQB |
| GH | 1AXI, 1A22, 1BP3 |
| EPO | 1CN4 |
| IL-13Rα1 | 3BPN, 3BPO, 3LB6 |
| EGFR | 1IVO, 3B2U, 1MOX, 3C09, 1YY9, 3NJP, 3LTF |

Results

Interleukin-13 (IL-13)

Human IL-13 is as described in Example 1. We utilized sSIM, PredUs, and simple hydrophobic analysis (Hydrophobic) to predict IL-13 hot-spot and binding-region residues from the available NMR structure (PDB ID: 1UZ[35]) of unbound IL-13. For ISIS prediction, we used the amino acid sequence of IL-13. We also performed 20 ns MD simulation of IL-13 and applied the dSIM tool to the last 15 ns of the simulation. Similar to the results in Example 1, as we decreased $\Phi_{cutoff}$ from 0.2 to 0.1, we identified more and larger highly hydrophobic clusters by sSIM. A similar trend was observed for dSIM; however no cluster was identified by dSIM when the $\Phi_{cutoff}$ was 0.2.

Table 12 shows the accuracy and coverage of hot-spot residue predictions for human IL-3 using SIM and a comparison of SIM results with PredUs and Hydrophobic. As shown in Table 12, SIM was more accurate than PredUs and Hydrophobic at predicting host-spot residues.

In Table 3 values in parenthesis are $EC_{50,(Ala)}/EC_{50,(WT)}$. SAA of side-chain of F44 in the crystal structure (PDB ID: 1M47) is 0.37 Å$^2$, which is less than our cutoff of 10 Å$^2$. In fact, it has been shown that F44A mutation leads to change in IL-2 conformation.[4]

TABLE 12

| Experiments | | Predictions | | | | | | |
|---|---|---|---|---|---|---|---|---|
| IL-13 + IL-13Rα1 [1] | IL-13 + IL-13Rα2 [1] | sSIM (0.2) | sSIM (0.15) | sSIM (0.1) | dSIM (0.15) | dSIM (0.1) | PredUs | Hydrophobic |
| I14 (187.6) | I14 | | | | | | ✓ | ✓ |
| M33 (51.2) | | | ✓ | | ✓ | | | ✓ |
| K89 (7.6) | | | | ✓ | | ✓ | ✓ | |
| I90 (10) | | | | ✓ | | | | ✓ |
| E91 (8) | | | | ✓ | | ✓ | | |
| K104 (232.5) | K104 (18291) | ✓ | ✓ | ✓ | ✓ | ✓ | ✓ | |
| | K105 (73.4) | | | | | ✓ | | |
| F107 (>60) | F107 (5639) | ✓ | ✓ | ✓ | ✓ | ✓ | | ✓ |
| R108 (124.9) | | ✓ | ✓ | ✓ | ✓ | ✓ | ✓ | |
| Others | | +0 | +3 | +8 | +1 | +5 | +27 | +30 |
| Coverage (%) | | 33.3 | 33.3 | 77.8 | 33.3 | 66.7 | 55.6 | 44.4 |
| Accuracy (%) | | 100 | 50 | 46.7 | 75 | 54.5 | 15.6 | 11.8 |
| Max. Acc. (%) | | 100 | 66.7 | 66.7 | 75 | 63.6 | 31.2 | 23.53 |

In Table 12 values in parenthesis are $K_{D,(Ala)}/K_{D,(WT)}$. K105 is not highly conserved as indicated by a ConSurf score of 2.83 (see Example 1). K105 is identified by sSIM (0.2-0.1) and dSIM (0.15-0.1) when we do not include sequence conservation.

Interleukin-2 (IL-2)

Human IL-2 is as described in Example 1. We applied sSIM, PredUs, and Hydrophobic to the x-ray structure of the unbound IL-2 (PDB ID: 1M47[39]). We also performed 20 ns of MD simulation for IL-2 and applied dSIM to the last 15 ns of the trajectory.

Table 13 shows the accuracy and coverage of hot-spot residue predictions for human IL-2 using SIM and a comparison of SIM results with PredUs and Hydrophobic. As shown in Table 13, SIM was more accurate than PredUs and Hydrophobic at predicting host-spot residues.

Growth Hormone Receptor (GHR)

Human GHR is as described in Example 1. We utilized sSIM, PredUs, and Hydrophobic to predict binding-region residues of the extracellular domain of GHR from the available x-ray structure (PDB ID: 1A22). We also performed 20 ns MD simulation of GHR and applied the dSIM tool to the last 15 ns of the simulation.

Table 14 shows the accuracy and coverage of hot-spot residue predictions for human GHR using SIM and a comparison of SIM results with PredUs and Hydrophobic. As shown in Table 14, SIM, PredUs, and Hydrophobic were able to predict host-spot residues.

TABLE 13

| Experiments | | Predictions | | | | | | | |
|---|---|---|---|---|---|---|---|---|---|
| IL-2 + IL-2Rα [2] | IL-2 + IL-2Rβ [3] | sSIM (0.3) | sSIM (0.2) | sSIM (0.15) | dSIM (0.25) | dSIM (0.15) | dSIM (0.1) | PredUs | Hydrophobic |
| T41 (12) | | | | | | | | | |
| F42 (>100) | | | ✓ | ✓ | | ✓ | ✓ | | ✓ |
| K43 (15) | | | ✓ | ✓ | | ✓ | ✓ | | |
| F44 (17) | | | | | | | | | |
| Y45 (>100) | | | ✓ | ✓ | | ✓ | ✓ | | ✓ |
| E62 (>100) | | | ✓ | ✓ | | ✓ | ✓ | | |
| | D20 | ✓ | ✓ | ✓ | ✓ | ✓ | ✓ | | |
| | N88 | | | | | | | | |
| Others | | +3 | +6 | +9 | +3 | +10 | +21 | +27 | +27 |
| Coverage (%) | | 12.5 | 62.5 | 62.5 | 12.5 | 62.5 | 62.5 | 0 | 25 |
| Accuracy (%) | | 25 | 45.5 | 35.7 | 25 | 33.3 | 20 | 0 | 6.90 |
| Max. Acc. (%) | | 75 | 81.8 | 71.4 | 75 | 66.7 | 52 | 66.7 | 58.6 |

TABLE 14

| Experiments GHR + GH [5] | sSIM (0.2) | sSIM (0.15) | sSIM (0.12) | sSIM (0.1) | dSIM (0.2) | dSIM (0.15) | dSIM (0.1) | PredUs | Hydrophobic |
|---|---|---|---|---|---|---|---|---|---|
| R43 (35.7) | | ✓ | ✓ | ✓ | | | | ✓ | |
| E44 (17.4) | | | ✓ | ✓ | | | | ✓ | |
| I103 (15.1) | | | | | | | | ✓ | |
| W104 (>2500) | | ✓ | ✓ | ✓ | | ✓ | ✓ | ✓ | ✓ |
| I105 (26.5) | | | | | | | | ✓ | ✓ |
| P106 (265) | | | | | | | | ✓ | ✓ |
| D164 (12.3) | | | ✓ | ✓ | | | | ✓ | |
| I165 (36.5) | | | ✓ | ✓ | | ✓ | ✓ | ✓ | ✓ |
| W169 (>2500) | | | ✓ | ✓ | | ✓ | ✓ | ✓ | ✓ |
| Others: | +4 | +15 | +26 | +34 | +5 | +22 | +33 | +42 | +43 |
| Coverage (%) | 0 | 22.2 | 66.7 | 66.7 | 0 | 33.3 | 33.3 | 100.0 | 55.6 |
| Accuracy (%) | 0 | 11.8 | 18.7 | 15 | 0 | 12 | 8.3 | 17.6 | 10.4 |
| Max. Acc. (%) | 50 | 41.2 | 40.6 | 32.5 | 40 | 32 | 30.6 | 58.8 | 39.6 |

In Table 14, GH refers to "growth hormone." Values in parenthesis are $K_{D,(Ala)}/K_{D,(WT)}$. SAA of side-chain of I103 is 7 Å$^2$, which is less than our cutoff of 10 Å$^2$. I105 and P106 are not highly conserved as indicated by their ConSurf score of 0.59 2.43 respectively (see Example 1). I105 is identified by sSIM (0.1) and dSIM (0.1) when we do not include sequence conservation.

Human Immunoglobulin G1 (IgG1)

We utilized sSIM, PredUs, and Hydrophobic to predict binding-region residues of IgG1 from the available structure. We also performed 20 ns MD simulation of IgG1 and applied the dSIM tool to the last 15 ns of the simulation.

Table 15 shows the accuracy and coverage of hot-spot residue predictions for human IgG1 using SIM and a comparison of SIM results with PredUs and Hydrophobic. As shown in Table 15, SIM, PredUs, and Hydrophobic were able to predict host-spot residues.

Human Interleukin-15 (IL-15)

We utilized sSIM, PredUs, and Hydrophobic to predict binding-region residues of IL-15 from the available structure. We also performed 20 ns MD simulation of IL-15 and applied the dSIM tool to the last 15 ns of the simulation.

Table 16 shows the accuracy and coverage of hot-spot residue predictions for human IL-15 using SIM and a comparison of SIM results with PredUs and Hydrophobic. As shown in Table 14, SIM and PredUs were able to predict host-spot residues.

TABLE 15

| Experiments | | | | | | Predictions | | | | | |
|---|---|---|---|---|---|---|---|---|---|---|---|
| Fc + FcRn [6] | Fc + FcγRI [6] | sSIM (0.3) | sSIM (0.25) | sSIM (0.2) | sSIM (0.15) | dSIM (0.3) | dSIM (0.25) | dSIM (0.2) | dSIM (0.15) | PredUs | Hydrophobic |
| | E233 | | | | | | | | | ✓ | |
| | L234 | | | | | | | | | | ✓ |
| | L235 | | ✓ | ✓ | ✓ | | ✓ | ✓ | ✓ | ✓ | ✓ |
| I253 (<0.1) | | ✓ | ✓ | ✓ | ✓ | ✓ | ✓ | ✓ | ✓ | ✓ | ✓ |
| S254 (<0.1) | | | | | | | | | | ✓ | |
| H435 (<0.1) | | | | | | | | | | | |
| Y436 (<0.1) | | | | | | | | | | | ✓ |
| Others | | +3 | +9 | +9 | +18 | +3 | +8 | +11 | +17 | +62 | +46 |
| Coverage (%) | | 14.3 | 28.6 | 28.6 | 28.6 | 14.3 | 28.6 | 28.6 | 28.6 | 57.1 | 57.1 |
| Accuracy (%) | | 25 | 18.2 | 18.2 | 10 | 25 | 20 | 15.4 | 10.5 | 6 | 8 |
| Max. Acc. (%) | | 25 | 18.2 | 18.2 | 20 | 25 | 20 | 23.1 | 15.8 | 50 | 30 |

In Table 15, FcRn refers to "neonatal Fc-receptor." Values in parenthesis are the ratio of binding of the Ala-variant to that of native IgG1 at 0.33 or 1 μg/ml. The mutant E233P, L234V, L235A G236Δ has a value of 0.54 for the ratio of binding of the mutant to that of native IgG1. E233, E234 and Y436 are not highly conserved as indicated by their ConSurf score of 0.81, 1.89 and 2.03 respectively (see Example 1). E233 and E234 are identified by sSIM (0.3-0.15) and dSIM (0.25-0.15) when we do not include sequence conservation. Y436 is identified by dSIM (0.15) when we do not include sequence conservation.

TABLE 16

| Experiments | Predictions | | | | |
|---|---|---|---|---|---|
| IL-15 + IL-15Rα [7] | sSIM (0.3) | sSIM (0.2) | sSIM (0.15) | PredUs | Hydrophobic |
| D22 (27) | | | | ✓ | |
| Y26 (85000) | | | | | ✓ |
| E46 (3800) | ✓ | ✓ | ✓ | | |
| L47 (78) | | | | | |
| E53 (370) | ✓ | ✓ | ✓ | | ✓ |
| E87 (320) | | | | | |
| E90 (3500) | | | | | |

TABLE 16-continued

| Experiments | Predictions | | | | |
|---|---|---|---|---|---|
| IL-15 + IL-15Rα [7] | sSIM (0.3) | sSIM (0.2) | sSIM (0.15) | PredUs | Hydrophobic |
| Others | +2 | +2 | +5 | +33 | +21 |
| Coverage (%) | 28.6 | 28.6 | 28.6 | 28.6 | 14.3 |
| Accuracy (%) | 50 | 50 | 28.6 | 5.7 | 4.6 |
| Max. Acc. (%) | 75 | 75 | 42.9 | 17.1 | 18.2 |

In Table 16, values in parenthesis are $K_{D,(Ala)}/K_{D,(WT)}$. SAA of side-chain of L47 is 0 Å$^2$, which is less than our cutoff of 10 Å$^2$.

Human Growth Hormone (GH)

We utilized sSIM, PredUs, and Hydrophobic to predict binding-region residues of GH from the available structure. We also performed 20 ns MD simulation of GH and applied the dSIM tool to the last 15 ns of the simulation.

Table 17 shows the accuracy and coverage of hot-spot residue predictions for human GH using SIM and a comparison of SIM results with PredUs and Hydrophobic.

TABLE 17

| Experiments GH + GHR [8] | Predictions | | | | |
|---|---|---|---|---|---|
| | sSIM (0.3) | sSIM (0.25) | sSIM (0.2) | PredUs | Hydrophobic |
| I58 (16.5) | | | | | ✓ |
| R64 (20.9) | | | | ✓ | |
| K172 (13.5) | | | | | |
| T175 (17.4) | | | | ✓ | |
| F176 (15.9) | | | | ✓ | |
| Others | +3 | +7 | +13 | +58 | +54 |
| Coverage (%) | 0 | 0 | 0 | 60.0 | 20 |
| Accuracy (%) | 0 | 0 | 0 | 4.92 | 1.8 |
| Max. Acc. (%) | 25 | 40 | 26.32 | 32.8 | 16.3 |

In Table 7, GHR refers to "growth hormone receptor." Values in parenthesis are $K_{D,(Ala)}/K_{D,(WT)}$. T175 was mutated to Ser. SAA of side-chains of K172 and F176 are 1.35 and 9 Å$^2$ resp., which is less than our cutoff of 10 Å$^2$. Crystal structure of GH bound to GHR (PDB ID: 3HHR) indicates that I58 of GH is, in fact, not even present in the binding region. Since, I58 is present on a loop, it is highly likely that I58A mutation disrupts the local conformation of the loop resulting in observed decrease in binding. Hence, I58 is important in maintaining the right conformation of the loop; while the energetic contribution of I58 to the binding is negligible. F176A and K172A are highly likely to disrupt the loop (S51-N63) conformation since both F176 and K172 interacts with multiple residues of this loop. Hence, major contribution of reduction in binding to GHR upon mutation in these two residues is more likely to be a result of loop conformational change. Binding-region residues for GH-GHR complex were identified using the structure PDB ID: 3HHR.

Average Performance of SIM, PredUs, and Hydrophobic

Tables 18-20 show the average protein-protein interaction residue prediction performance of SIM, PredUs, and Hydrophobic. For SIM, the averages are computed using sSIM at $\Phi_{cutoff}$=0.15 and $\Phi_{cutoff}$=0.2.

Table 18 shows the accuracy of SIM, PredUs, and Hydrophobic for prediction of hot-spot residues.

TABLE 18

| Protein | sSIM (0.2) | sSIM (0.15) | PredUs | Hydrophobic |
|---|---|---|---|---|
| IL-13 | 100 | 50 | 15.6 | 11.8 |
| IL-2 | 45.5 | 35.71 | 0 | 6.9 |
| GHR | 0 | 11.8 | 17.6 | 10.4 |
| Fc | 18.2 | 10 | 6 | 8 |
| IL-15 | 50 | 28.6 | 5.7 | 4.6 |
| GH | 0 | 0 | 4.92 | 1.8 |
| Average | 36% | 23% | 8% | 7.25% |

Table 19 shows the theoretical maximum accuracy of SIM, PredUs, and Hydrophobic for prediction of hot-spot residues.

TABLE 19

| Protein | sSIM (0.2) | sSIM (0.15) | PredUs | Hydrophobic |
|---|---|---|---|---|
| IL-13 | 100 | 66.7 | 31.2 | 23.5 |
| IL-2 | 75 | 71.43 | 66.7 | 58.6 |
| GHR | 50 | 41.2 | 58.8 | 39.6 |
| Fc | 18.2 | 20 | 50 | 30 |
| IL-15 | 75 | 42.9 | 17.1 | 18.2 |
| GH | 26.32 | 26.32 | 32.8 | 16.3 |
| Average | 57 | 45 | 43% | 31% |

Table 20 shows the accuracy of SIM, PredUs, and Hydrophobic for prediction of binding-region residues.

TABLE 20

| Protein | sSIM (0.2) | sSIM (0.15) | PredUs | Hydrophobic |
|---|---|---|---|---|
| IL-13 | 100 | 83.33 | 50 | 29.41 |
| IL-2 | 81.82 | 71.43 | 66.67 | 58.62 |
| GHR | 50 | 41.18 | 58.82 | 39.58 |
| Fc | 42.11 | 30 | 56.06 | 36 |
| IL-15 | 100 | 100 | 20 | 22.73 |
| GH | 42.11 | 42.11 | 57.38 | 25.45 |
| Average | 69% | 61% | 51% | 35.3% |

REFERENCES

1. Stumpf, M. P. H., Thorne, T., de Silva, E., Stewart, R., An, H. J., Lappe, M. & Wiuf, C. (2008). Estimating the size of the human interactome. *Proc. Natl. Acad. Sci. U.S.A.* 105, 6959-6964.
2. Thanos, C. D., DeLano, W. L. & Wells, J. A. (2006). Hot-spot mimicry of a cytokine receptor by a small molecule. *Proc. Natl. Acad. Sci. U.S.A.* 103, 15422-15427.
3. Bullock, B. N., Jochim, A. L. & Arora, O. S. Assessing helical protein interfaces for inhibitor design. *J. Am. Chem. Soc.* in press.
4. Cunningham, B. C. & Wells, J. A. (1989). High-Resolution Epitope Mapping of Hgh-Receptor Interactions by Alanine-Scanning Mutagenesis. *Science* 244, 1081-1085.
5. Ofran, Y. & Rost, B. (2007). Protein-protein interaction hotspots carved into sequences. *Plos Computational Biology* 3, 1169-1176.
6. Rao, G. V. & Brooks, C. L. (2011). Functional Epitopes for Site 1 of Human Prolactin. *Biochemistry* 50, 1347-1358.
7. Kortemme, T. & Baker, D. (2002). A simple physical model for binding energy hot spots in protein-protein complexes. *Proc. Natl. Acad. Sci. U.S.A.* 99, 14116-14121.

8. Lise, S., Buchan, D., Pontil, M. & Jones, D. T. (2011). Predictions of Hot Spot Residues at Protein-Protein Interfaces Using Support Vector Machines. *Plos One* 6.
9. Xia, J. F., Zhao, X. M., Song, J. N. & Huang, D. S. (2010). APIS: accurate prediction of hot spots in protein interfaces by combining protrusion index with solvent accessibility. *BMC Bioinformatics* 11.
10. Tuncbag, N., Gursoy, A. & Keskin, O. (2009). Identification of computational hot spots in protein interfaces: combining solvent accessibility and inter-residue potentials improves the accuracy. *Bioinformatics* 25, 1513-1520.
11. Ofran, Y. & Rost, B. (2007). ISIS: interaction sites identified from sequence. *Bioinformatics* 23, E13-E16.
12. Fernández-Recio, J. (2011). Prediction of protein binding sites and hot spots. *WIREs Comput Mol Sci,* 1: 680-698. doi: 10.1002/wcms.45.
13. Tuncbag, N., Kar, G., Keskin, O., Gursoy, A. & Nussinov, R. (2009). A survey of available tools and web servers for analysis of protein-protein interactions and interfaces. *Briefings in Bioinformatics* 10, 217-232.
14. Qin, S. & Zhou, H. X. (2007). meta-PPISP: a meta web server for protein-protein interaction site prediction. *Bioinformatics* 23, 3386-3387.
15. Glaser, F., Pupko, T., Paz, I., Bell, R. E., Bechor-Shental, D., Martz, E. & Ben-Tal, N. (2003). ConSurf: Identification of Functional Regions in Proteins by Surface-Mapping of Phylogenetic Information. *Bioinformatics* 19, 163-164.
16. Chen, H. L. & Zhou, H. X. (2005). Prediction of interface residues in protein-protein complexes by a consensus neural network method: Test against NMR data. *Proteins—Structure Function and Bioinformatics* 61, 21-35.
17. Neuvirth, H., Raz, R. & Schreiber, G. (2004). ProMate: A structure based prediction program to identify the location of protein-protein binding sites. *J. Mol. Biol.* 338, 181-199.
18. Zhou, Y. Q., Liang, S. D., Zhang, C. & Liu, S. (2006). Protein binding site prediction using an empirical scoring function. *Nucleic Acids Research* 34, 3698-3707.
19. Armon, A., Graur, D. & Ben-Tal, N. (2001). ConSurf: An algorithmic tool for the identification of functional regions in proteins by surface mapping of phylogenetic information. *J. Mol. Biol.* 307, 447-463.
20. Chennamsetty, N., Voynov, V., Kayser, V., Helk, B. & Trout, B. L. (2009). Design of therapeutic proteins with enhanced stability. *Proc. Natl. Acad. Sci. U.S.A.* 106, 11937-11942.
21. Trout, B. L., Chennamsetty, N., Voynov, V., Kayser, V. & Helk, B. (2011). Prediction of protein binding regions. *Proteins-Structure Function and Bioinformatics* 79, 888-897.
22. Lijnzaad, P. & Argos, P. (1997). Hydrophobic patches on protein subunit interfaces: Characteristics and prediction. *Proteins-Structure Function and Genetics* 28, 333-343.
23. Kozakov, D., Hall, D. R., Chuang, G.-Y., Cencic, R., Brenke, R., Grove, L. E., Beglov, D., Pelletier, J., Whitty, A. & Vajdaa, S. (2011). Structural conservation of druggable hot spots in protein-protein interfaces. *Proc. Natl. Acad. Sci. U.S.A.* 2011 Aug. 16; 108(33):13528-33.
24. Berman, H. M., Westbrook, J., Feng, Z., Gilliland, G., Bhat, T. N., Weissig, H., Shindyalov, I. N. & Bourne, P. E. (2000). The Protein Data Bank. *Nucleic Acids Research* 28, 235-242.
25. Arnold, K., Bordoli, L., Kopp, J. & Schwede, T. (2006). The SWISS-MODEL workspace: a web-based environment for protein structure homology modelling. *Bioinformatics* 22, 195-201.
26. Humphrey, W., Dalke, A. & Schulten, K. (1996). VMD: Visual molecular dynamics. *Journal of Molecular Graphics* 1996 February; 14(1):33-8, 27-8.
27. MacKerell, A. D., Bashford, D., Bellott, M., Dunbrack, R. L., Evanseck, J. D., Field, M. J., Fischer, S., Gao, J., Guo, H., Ha, S., Joseph-McCarthy, D., Kuchnir, L., Kuczera, K., Lau, F. T. K., Mattos, C., Michnick, S., Ngo, T., Nguyen, D. T., Prodhom, B., Reiher, W. E., Roux, B., Schlenkrich, M., Smith, J. C., Stote, R., Straub, J., Watanabe, M., Wiorkiewicz-Kuczera, J., Yin, D. & Karplus, M. (1998). All-atom empirical potential for molecular modeling and dynamics studies of proteins. *J. Phys. Chem. B* 102, 3586-3616.
28. Phillips, J. C., Braun, R., Wang, W., Gumbart, J., Tajkhorshid, E., Villa, E., Chipot, C., Skeel, R. D., Kale, L. & Schulten, K. (2005). Scalable molecular dynamics with NAMD. *Journal of Computational Chemistry* 26, 1781-1802.
29. Black, S. D. & Mould, D. R. (1991). Development of Hydrophobicity Parameters to Analyze Proteins Which Bear Posttranslational or Cotranslational Modifications. *Analytical Biochemistry* 193, 72-82.
30. Fiorucci, S. & Zacharias, M. (2010). Prediction of Protein-Protein Interaction Sites Using Electrostatic Desolvation Profiles. *Biophys. J.* 98, 1921-1930.
31. Cuthill, E. & McKee, J. (1969). Reducing the bandwidth of sparse symmetric matrices. In *Proceedings of the* 1969 24*th national conference*, pp. 157-172.
32. Krissinel, E. & Henrick, K. (2007). Inference of macromolecular assemblies from crystalline state. *J. Mol. Biol.* 372, 774-797.
33. Lupardus, P. J., Birnbaum, M. E. & Garcia, K. C. (2010). Molecular Basis for Shared Cytokine Recognition Revealed in the Structure of an Unusually High Affinity Complex between IL-13 and IL-13R alpha 2. *Structure* 18, 332-342.
34. LaPorte, S. L., Juo, Z. S., Vaclavikova, J., Colf, L. A., Qi, X. L., Heller, N. M., Keegan, A. D. & Garcia, K. C. (2008). Molecular and structural basis of cytokine receptor pleiotropy in the interleukin-4/13 system. *Cell* 132, 259-272.
35. Moy, F. J., Diblasio, E., Wilhelm, J. & Powers, R. (2001). Solution structure of human IL-13 and implication for receptor binding. *J. Mol. Biol.* 310, 219-230.
36. Rickert, M., Wang, X. Q., Boulanger, M. J., Goriatcheva, N. & Garcia, K. C. (2005). The structure of interleukin-2 complexed with its alpha receptor. *Science* 308, 1477-1480.
37. Wang, X. Q., Rickert, M. & Garcia, K. C. (2005). Structure of the quaternary complex of interleukin-2 with its alpha, beta, and gamma(c) receptors. *Science* 310, 1159-1163.
38. Stauber, D. J., Debler, E. W., Horton, P. A., Smith, K. A. & Wilson, I. A. (2006). Crystal structure of the IL-2 signaling complex: Paradigm for a heterotrimeric cytokine receptor. *Proc. Natl. Acad. Sci. U.S.A.* 103, 2788-2793.
39. Arkin, M. R., Randal, M., DeLano, W. L., Hyde, J., Luong, T. N., Oslob, J. D., Raphael, D. R., Taylor, L., Wang, J., McDowell, R. S., Wells, J. A. & Braisted, A. C. (2003). Binding of small molecules to an adaptive protein-protein interface. *Proc. Natl. Acad.* Sci. U.S.A. 100, 1603-1608.

40. Clackson, T., Ultsch, M. H., Wells, J. A. & de Vos, A. M. (1998). Structural and functional analysis of the 1:1 growth hormone:receptor complex reveals the molecular basis for receptor affinity. *J. Mol. Biol.* 277, 1111-1128.
41. Weir M P, Chaplin M A, Wallace D M, Dykes C W, Hobden A N. Structure Activity Relationships of Recombinant Human Interleukin-2. *Biochemistry*. Sep. 6 1988; 27(18):6883-6892.
42. Shields R L, Namenuk A K, Hong K, et al. High resolution mapping of the binding site on human IgG1 for Fc gamma RI, Fc gamma RII, Fc gamma RIII, and FcRn and design of IgG1 variants with improved binding to the Fc gamma R. *J. Biol. Chem.* Mar. 2 2001; 276(9):6591-6604.
43. Sakamoto S, Caaveiro J M M, Sano E, Tanaka Y, Kudou M, Tsumoto K. Contributions of Interfacial Residues of Human Interleukin 15 to the Specificity and Affinity for Its Private alpha-Receptor. *J. Mol. Biol.* Jun. 26 2009; 389(5):880-894.
44. Zhang Q C, Deng L, Fisher M, Guan J H, Honig B, Petrey D. PredUs: a web server for predicting protein interfaces using structural neighbors. *Nucleic Acids Res* 2011; 39:W283-W287.
45. Zhang Q C, Petrey D, Norel R, Honig B H. Protein interface conservation across structure space. *Proc Natl Acad Sci USA* 2010; 107(24):10896-10901.

We claim:

1. An in vitro method of producing a protein variant which exhibits increased binding to a macromolecule, the method comprising
   replacing or deleting one or more hot-spot amino acid residues in the protein by site-directed mutagenesis, wherein binding affinity of the modified protein to a macromolecule is increased, as compared to a corresponding protein lacking the replacement or deletion of one or more hot-spot amino acid residues,
   (i) wherein the one or more hot-spot amino acid residues were identified using a computer-implemented method for predicting hot-spot amino acid residues of the protein, or portion thereof,
   wherein the protein, or portion thereof, was represented in a structural model comprising a plurality of amino acid residues, and wherein
   (i) a cluster of highly hydrophobic amino acid residues was selected from the plurality of amino acid residues of the model, wherein the cluster comprised two or more amino acid residues each having an effective-hydrophobicity greater than a chosen threshold, and wherein each amino acid residue in the cluster was within a first defined distance of at least one other amino acid residue in the cluster;
   (ii) one or more solvent-exposed polar amino acid residues within a second defined distance of at least one amino acid residue in the cluster of highly hydrophobic amino acid residues was selected from the plurality of amino acid residues of the model;
   (iii) amino acid residues that did not meet a criterion for evolutionary conservation were removed from the cluster of highly hydrophobic amino acid residues and from the one or more solvent-exposed polar amino acid residues, to produce a set of one or more predicted hot-spot amino acid residues; and
   (iv) the one or more predicted hot-spot amino acid residues were stored;
   wherein, if the hot-spot amino acid residue is replaced and is in the cluster of highly hydrophobic amino acid residues, it is replaced with an amino acid residue which is more hydrophobic such that the binding affinity is increases, or if the hot-spot amino acid residue is replaced and is from the one or more solvent-exposed polar amino acid residues, it is replaced with an amino acid residue which is more hydrophilic such that the binding affinity is increases.

2. The method of claim 1, wherein additional hot-spot amino acid residues of the protein, or portion thereof, that are replaced or deleted to increase binding affinity of the protein variant to the macromolecule were predicted by repeating steps (i)-(iv) for at least two additional clusters of highly hydrophobic amino acid residues of the protein, or portion thereof.

3. The method of claim 1, wherein additional hot-spot amino acid residues of the protein, or portion thereof, for all clusters of highly hydrophobic amino acid residues of the protein, or portion thereof, that can be replaced or deleted to increase binding affinity of the protein variant to the macromolecule when mutated were predicted by performing steps (i)-(iv) for each of the clusters, wherein each step was conducted in parallel for each cluster, or each series of steps (i)-(ii) was performed serially for each cluster.

4. The method of claim 1, wherein the one or more predicted hot-spot amino acid residues that can be replaced or deleted to increase binding affinity of the protein variant to the macromolecule when mutated were presented as a contour map visual display.

5. The method of claim 4, wherein the contour map was an electron density map.

6. The method of claim 4, wherein the contour map was a map of a structural binding pocket.

7. The method of claim 1, wherein the effective-hydrophobicity threshold was 0.10.

8. The method of claim 1, wherein the first defined distance between at least two amino acid residues in the cluster was at most 15 Å.

9. The method of claim 1, wherein the first defined distance between at least two amino acid residues in the cluster was the shortest distance between any two atoms of the at least two amino acid residues, wherein each of the two atoms were from separate amino acid residues.

10. The method of claim 1, wherein the one or more solvent-exposed polar amino acid residues had a solvent accessible area (SAA) greater than 15 $Å^2$.

11. The method of claim 1, wherein the second defined distance between a solvent-exposed polar amino acid residue and at least one amino acid residue in the cluster of highly hydrophobic amino acid residues was at most 20 Å.

12. The method of claim 1, wherein one or more of the solvent-exposed polar amino acid residues was selected to be within the cluster when the solvent-exposed charged amino acid residues were within a distance of at most 10 Å from a highly hydrophobic amino acid residue in the cluster.

13. The method of claim 1, wherein the criterion for evolutionary conservation was a sequence-conservation threshold.

14. The method of claim 13, wherein the sequence-conservation threshold was a ConSurf score that was 0.3.

15. The method of claim 1, wherein the effective-hydrophobicity was calculated by:

(a) selecting an amino acid residue from the plurality of amino acid residues of the model;

(b) calculating, for all side-chain atoms of the amino acid residue, a ratio of the solvent accessible area (SAA) of the atoms to the SAA of atoms in an identical residue which is fully exposed; and (c) multiplying each ratio by the hydrophobicity of the amino acid as determined by an amino acid hydrophobicity scale, whereby the product of step (c) was the effective-hydrophobicity of the amino acid residue.

16. The method of claim 1, wherein the macromolecule is selected from the group consisting of a protein binding partner, an antigen, an epitope, a peptide, a ligand, a receptor, a carbohydrate, a chemical, a small molecule, and an inhibitor.

17. The method of claim 1, further comprising replacing at least one residue in the cluster of highly hydrophobic amino acid residues identified in step (ii) with at least one less hydrophobic amino acid residues, wherein the at least one residue in the cluster of highly hydrophobic amino acid residues is not a predicted hot-spot amino acid residue, and wherein replacing the at least one amino acid residues in the cluster of highly hydrophobic amino acid residues reduces protein aggregation without affecting macromolecule binding.

* * * * *